(12) United States Patent  
Goldsborough

(10) Patent No.: US 6,867,290 B2  
(45) Date of Patent: Mar. 15, 2005

(54) MODIFIED POLYNUCLEOTIDES AND USES THEREOF

(75) Inventor: Andrew Simon Goldsborough, St. Gely du Fesc (FR)

(73) Assignee: Cyclops Genome Sciences, Ltd. (GB)

( * ) Notice: Subject to any disclaimer, the term of this patent is extended or adjusted under 35 U.S.C. 154(b) by 113 days.

(21) Appl. No.: 10/011,495

(22) Filed: Oct. 26, 2001

(65) Prior Publication Data

US 2003/0039985 A1 Feb. 27, 2003

Related U.S. Application Data

(63) Continuation of application No. PCT/GB00/01670, filed on May 2, 2000, and a continuation of application No. PCT/GB00/01687, filed on May 2, 2000, and a continuation of application No. PCT/GB00/01683, filed on May 2, 2000.

(30) Foreign Application Priority Data

Apr. 30, 1999 (GB) ............................................. 9910154  
Apr. 30, 1999 (GB) ............................................. 9910156  
Apr. 30, 1999 (GB) ............................................. 9910157  
Apr. 30, 1999 (GB) ............................................. 9910158

(51) Int. Cl.$^7$ ........................... C12N 15/11; C12Q 1/68; C07H 21/04

(52) U.S. Cl. ........................ 536/23.1; 435/6; 435/91.1; 536/24.3

(58) Field of Search ..................... 435/6, 7.72, 91.1, 435/91.2, 91.3, 91.32, 307.1; 536/23.1, 24.3

(56) References Cited

U.S. PATENT DOCUMENTS

| | | |
|---|---|---|
| 5,426,180 A | 6/1995 | Kool |
| 5,660,985 A | 8/1997 | Pieken et al. |
| 5,681,726 A | 10/1997 | Huse et al. |
| 5,700,642 A | * 12/1997 | Monforte et al. ............... 435/6 |
| 5,707,796 A | 1/1998 | Gold et al. |
| 5,783,425 A | 7/1998 | Dudycz et al. |
| 5,859,221 A | 1/1999 | Cook et al. |
| 5,872,232 A | 2/1999 | Cook et al. |
| 6,008,334 A | * 12/1999 | Hanna ........................ 536/22.1 |

FOREIGN PATENT DOCUMENTS

| | | |
|---|---|---|
| WO | 92/03568 | 3/1992 |
| WO | WO 94/19012 | 1/1994 |
| WO | 98/13526 | 4/1998 |
| WO | 99/14346 | 3/1999 |
| WO | 99/36517 | 7/1999 |
| WO | 99/55857 | 11/1999 |
| WO | WO 00/75302 | 12/2000 |

OTHER PUBLICATIONS

Yu et al., "mRNA acetylated at 2'–OH group of ribose residues is functionally active in the cell–free translation system from whe embryos," FEBS, Sep. 1990, vol. 270, p. 111–114.*

Lewis, R. "Kits take the trickiness out of RNA isolation, purification", The Scientist 11(7):16–20 (1997).

Pagratis, N.C. et al. "Potent 2'–amino–, and 2'–flouro–2'–deoxyribonucleotide RNA inhibitors of keratinocyte growth factor", Nature Biotechnology 15(1): 68–73 (1997).

Sproat, B.S., "Chemistry and applications of oligonucleotide analogues", Journal of Biotechnology 41:221–238 (1995).

Ovodov, S.Y., "mRNA acetylated at 2'–OH–groups of ribose residues is functionally active in the cell–free translation system from wheat embryos", FEBS 270(1,2):111–114 (1990).

Ru, K. et al. "Specific inhibition of breast cancer cells by antisense poly–DNP–oligoribonucleotides and targeted apoptosis", Oncology Res. 10:389–397 (1998).

Roche Applied Science Advertisement: Protector RNase Inhibitor: Enhance the protection of RNA against Degradation.

Knorre, D.G., et al. "Production of transfer RNA acetylated at its 2'–hydroxy groups" Biochemistry USSR 1045–1050 (1965): translated from Biokhimiya 30:6 (1965).

Knorre, D.G., et al., "Investigation of the role of 2'–OH groups in the formation of secondary structure in polyribonucleotides" Biochim. Biophys. Acta 142:555 (1987).

Roland, A., et al., "Measurement of Copper–Binding Sites on Low Density Lipoprotein", Arterioscler Thromb Vasc Biol, pp. 594–602 (2001).

Knorre, D.G., et al. "Effect of Acetylation of the Ribose 2'–Hydroxyl Groups of Polyribonucleotides on Their Template Activity", Molekul.Biol 1: 837 (1967).

Heidenrich, Olaf et al., "Chemically Modified RNA: Approaches and Applications", The FASEB Journal, Jan. 1993, vol. 7.

Heidenrich, Olaf et al., "High Activity and Stability of Hammerhead Ribozymes Containing 2'–Modified Pyrimidine Nucleosides and Phosphorothioates", The Journal of Biological Chemistry, vol. 269, No. 3, Jan. 21, pp.2131–2138, 1994.

(List continued on next page.)

Primary Examiner—Kenneth R. Horlick  
Assistant Examiner—Young J. Kim  
(74) Attorney, Agent, or Firm—Saliwanchik, Lloyd & Saliwanchik

(57) ABSTRACT

Provided is a polynucleotide comprising mRNA, rRNA or viral RNA, comprising ribose rings that are covalently modified at the 2'-OH position. Further provided are methods for producing a double-stranded oligo- or polynucleotide from a template comprising an oligo- or polyribonucleotide, a proportion of the ribose rings of which are covalently modified at the 2'-OH position to bear a substituent which enables replication of the template by the nucleic acid polymerase. Also provided is use of a polynucleotide comprising mRNA, rRNA or viral RNA, a proportion of the ribose rings of which are covalently modified at the 2'-OH position, in a hybridisation reaction.

58 Claims, 5 Drawing Sheets

OTHER PUBLICATIONS

Aurup, Helle et al., "Translation of 2'–Modified mRNA in vitro and in vivo", Nucleic Acids Research, 1994, vol. 22, No. 23. pp. 4963–4968.

Xin, Wei et al., "Treatment of Duck Hepatitis B Virus by Antisense Poly–2'–O–(2,4–Dinitrophenyl)–Oligoribonucleotides", Bioenergetics Laboratory, Natural Sciences Center, State University of NY, Buffalo, Jul. 1998.

Iribarren, Adolfo M. et al., "2'–0–Alkyl Oligoribonucleotides as Antisense Probes", Proc. Natl. Acad. Sci.., vol. 87, pp 7747–7751, Oct. 1990.

Inoue, Hideo et al, "Synthesis and Hybridization Studies on Two Complementary Nona(2'–0–methyl) Ribonucleotides", Faculty of Pharmaceutical Sciences, Hokkaido University, Sapporo 060, Japan, Jun. 1987.

* cited by examiner

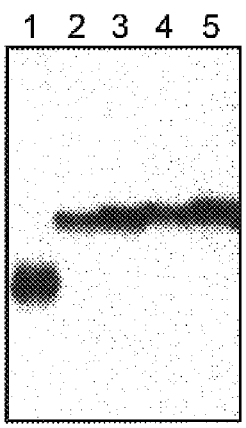
FIG. 7
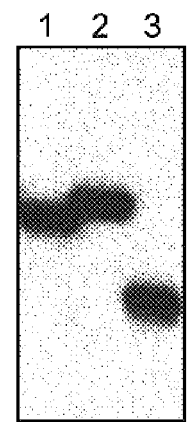
FIG. 8
FIG. 9
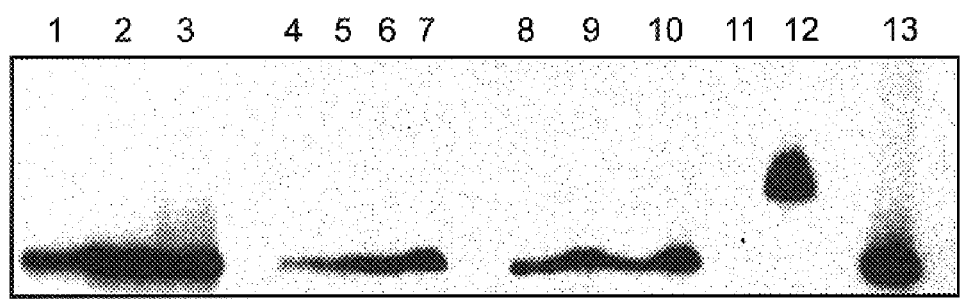
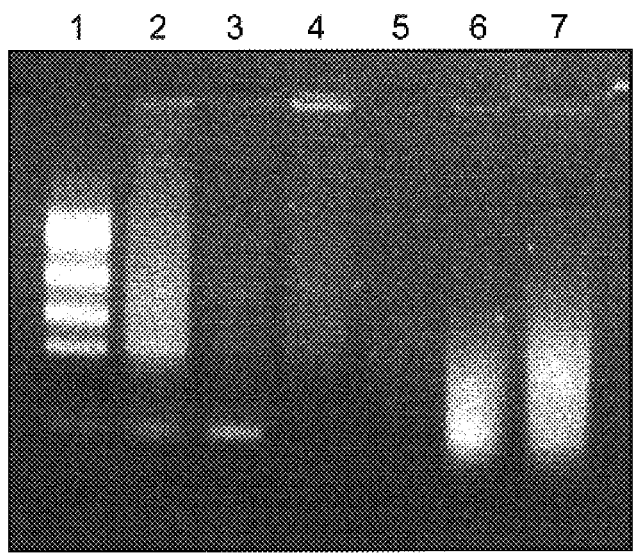
FIG. 10

MODIFIED POLYNUCLEOTIDES AND USES THEREOF

RELATED APPLICATIONS

The present application claims priority under 35 U.S.C. 120 from continuation PCT applications numbers PCT/GB00/01670, filed May 2, 2000; and continuation PCT/GB00/01687, filed May 2, 2000; and continuation PCT/GB00/01683, filed May 2, 2000, all three of which claim priority on British patent applications numbers 9910154.5, filed Apr. 30, 1999; 9910156.0, filed Apr. 30, 1999; 9910157.8, filed Apr. 30, 1999 and 9910158.6, filed Apr. 30, 1999, all of which were filed in English and the disclosures of which are incorporated herein by reference in their entireties.

FIELD OF THE INVENTION

The present invention relates to polynucleotides, modification of ribonucleic acid (RNA) to form oligo- and polynucleotides, and uses of such oligo- and polynucleotides.

BACKGROUND TO THE INVENTION

RNA serves as an essential component of every modern biological study. It provides a raw material for medical diagnostics, drug design, recombinant protein production, bioinformatics and almost every area concerning the pharmaceutical and biotechnology industries.

RNA is an essential and universal component of all organisms. There are three major types of RNA; these are messenger RNA (mRNA), transfer RNA (tRNA) and ribosomal RNA (rRNA), the latter being the most common type. In addition, some viruses encode their genes in the form of RNA such as the retroviruses, HIV being one example of this type. Other RNA forms include small infective RNA loops called viroids, PSTV being one example of this type. RNA has many diverse functions such as in the production of proteins and the storage of genetic information. The ability of RNA to carry out these functions is dependent on its composition and sequence.

mRNA is naturally produced from a DNA template by a process known as transcription. It accounts for less than 5% of the total RNA in a cell and exists in hundreds of thousands of forms depending on its sequence; however, nearly all eukaryotic mRNA have a 5' CAP structure and a 3' poly (A)+ tail, the latter serving as an essential feature for purifying mRNA from the bulk of the cellular RNA. There are estimated to be 500,000 mRNA molecules in an average mammalian cell. It contains the coding region for a protein and is crucial to understand the function of a gene.

All RNA molecules are linear macromolecules composed of repeated monomers (ribonucleotides) comprising a base, a ribose sugar and a phosphate. There are four principal bases: uracil, cytosine, guanine and adenine; the order in which they are connected together, the sequence, leads to many of the unique properties of RNA.

RNA differs chemically from DNA in two major ways. Firstly, it contains uracil instead of thymine, and secondly, RNA has a 2'-OH group on the ribose sugar instead of 2'-H found on the deoxyribose sugar of DNA.

Natural RNA has the 2' carbon atom bonded to two other carbon atoms (C1' and C3'), a hydrogen atom and an oxygen atom that forms part of a hydroxyl group (here called the 2'-OH group). The 2'-OH group endows RNA with many of its unique properties such as structure, reactivity and instability. The 2'-OH group can also assist in the cleavage of the phosphodiester bonds between ribonucleotides leading to chain cleavage and hence RNA degradation.

When RNA is manipulated for any number of common laboratory practices, its inherent instability leads to considerable technical and experimental difficulties. For example, measuring the abundance and size of a particular mRNA species is frequently considered essential to understanding the function of a gene. When the particular mRNA under study is degraded, even to a small extent, such measurements become impossible to carry out reliably or accurately. Another example would be the synthesis of a cDNA copy of a mRNA, where degradation of the mRNA precludes any possibility of obtaining a full and representative cDNA. Such cDNA copies are considered essential experimental tools because they allow a full and accurate characterisation of the gene such as its pattern of expression and chromosomal location. Furthermore the cDNA is essential to produce recombinant protein.

Protecting RNA from degradation whilst maintaining its biological activity is an essential task for any researcher or technician. However, the difficulty of removing nuclease activity from the RNA and the ease of accidentally introducing it, often precludes successful RNA manipulation to all except the most experienced. The cost and time considerations of RNA shipping and storage, equipment sterilisation, purchase of disposable plastic ware, training personnel and repeating failed experiments are a significant part of any laboratory budget.

The most important aspect of purifying RNA is to prevent degradation by RNases. RNases can be introduced from three sources: (1) intra-cellular sources due to carry-over from the experimental sample, (2) from external sources such as the researcher's skin secretions and (3) purified RNase used for DNA purification. RNases are truly ubiquitous; they can be found in finger tip secretions, dust, microbes, nearly all biological materials and even slight contamination will inevitably lead to RNA degradation. Compounding the problem is the common use of highly concentrated RNase in many DNA purification kits.

There are two principal means by which the 2'-OH group of ribonucleotides can be modified (a) enzymatically and (b) chemically. Enzymatic modification of the 2'-OH group arises from highly specific enzyme-catalysed reactions. For example, ribonucleotide reductase modifies the monomer ribonucleoside diphosphate, whereas an entire RNA molecule will not be recognised as a substrate. Another example is the methyl transferases that use an entire RNA molecule as a substrate but modify only a few 2'-OH groups per molecule.

The chemical synthesis of RNA and DNA is well known and many companies provide custom RNA and DNA synthesis (for review, see Eaton, (1995) *Annu. Rev. Biochem.* 64, 837). A considerable body of published work exists describing the different approaches to its synthesis (for review, see: Usman and Cedergreen (1992) *TIBS* 17:334). Protective groups have been reviewed (Greene and Wuts (1991) Protective Groups in Organic Synthesis, $2^{nd}$ Ed. Wiley Interscience). The most prominent route for preparation of 2'-modified ribopyrimidines is through the introduction of nucleophiles to the corresponding 2,2'-anhydropyrimidine precursor. This reaction is limited to preparation of 2'-halides, 2'-azide, 2'-thiolates (Moffatt, (1979) In: *Nucleoside Analogues*, Ed. Walker, pp.71–163, NY, Plenum., Townsend, (1988) *Chemistry of Nucleosides and Nucleotides*, pp.59–67, NY, Plenum), 2'-azido (Verheyden, et al., (1971) *J. Org. Chem.* 36:250) and 2'-amino ribonucleoside (Wagner, et al., (1972) *J. Org. Chem.* 37:1876). Methylation of the 3', 5'-protected precursor gives 2'-O-methyl ribonucleosides (Sproat, et al., (1991) *Oligonucleotides and Analogues: A Practical Approach*, ed. F. Eckstein, pp.49–86, NY. Oxford Univ. Press), and similarly 2'-O-alkyl and 2'-O-allyl derivatives have been made (Sproat, (1991) *Nucleic Acids Res.* 19:733, Lesnik, et al., (1993) *Biochemistry.* 32, 7832). Other modifications include 2'-methyl (Matsuda, et al., (1991) *J. Med. Chem.* 34:234), 2'-phenyl, 2'-alkyl ribonucleosides (Schmit (1994) *Synlett.* 234), 2'-acetylated (Imazawa, et al., (1979) *J. Org. Chem.* 44:2039), 2'-fluoro, 2'-trifluoromethyl (Schmit, (1994) *Synlett.* 241), 2'-mercapto (Imazawa, et al., (1975) *Chem. Pharm. Bull.* 23:604) and 2'-thio ribonucleosides (Divakar, et al., (1990) *J. Chem. Soc. Perkin Trans.* 1:969). 2'-Fluoro, 2'-O-methyl, 2'-O-propyl and 2'-O-pentyl nucleotides have each been incorporated into oligoribonucleotides (Cummins, (1995) *Nucleic Acid Res.* 23:2019). In each case the substrates and products are non-polymerised, that is they exist as simple monomers and not in the polyribonucleotide (RNA) form.

Practical applications of such 2'-modified ribonucleotides and polyribonucleotides include anti-viral activity (Wohlrab, et al., (1985) *Biochem. Biophys. Acta* 824:233), inhibition of bacterial growth (Salowe, et al., (1987) *Biochem.* 26:3408) and antisense oligonucleotides (Pieken, et al., (1991) *Science* 253:314). It has been shown that 2'-O-methoxyethyl replacement of the 2'-OH group can provide favourable conformations to enhance its binding to a target RNA. Research applications include developing novel ligands by the SELEX (systematic evolution of ligands by exponential enrichment) procedure (Gold, et al., (1995) *Annu. Rev. Biochem.* 64:763) and ribozyme research (Uhlenbeck, et al., (1987) *Nature* 328:596). The modification of the 2'-OH group as an investigative tool has been reviewed (Heidenreich, (1993) *FASEB J.,* 7:90). Many of the 2'-modified ribonucleotide triphosphates (Amersham International, Buckinghamshire, UK) or polymers (Midland Certified Reagent Company, Texas, USA) are available commercially.

Procedures suitable for modifying the 5'-OH and 3'-OH groups of deoxyribose have been developed in order to facilitate DNA oligonucleotide synthesis. For example, acetic anhydride in the presence of N-methylimidazole and tetrahydrofuran composes what is called the 'capping' reagent used commonly in almost all automated DNA synthesisers today. Other applications for acetic anhydride have been found, for example in the production of L-nucleoside dimers (Weis, International Patent Application, WO 97/11087).

Chemical modification studies are routinely carried out in order to analyse protein-RNA interactions (Jones et al., (1994) in RNA Isolation and Analysis. Bios. Oxford; Hecht (1996) Bioorganic Chemistry Nucleic Acids, Oxford University Press). Chemical modification is usually carried out with diethyl pyrocarbonate (Green et al., (1995) *J. Mol. Biol.* 247:60) which modifies the purine base or hydrazine which cleaves pyrimidines. For DNA footprinting studies, ethylnitrourea treatment is used to modify the phosphates leading to ethyl phosphotriester formation (Siebenlist and Gilbert (1980) *Proc. Nat'l. Acad. Sci.* 77:122; Green et al., (1995) *J. Mol. Biol.* 247:60). Alternatively, DNA may be treated with dimethylsulfate which leads to alkylation on the base (Carey (1989) *J. Biol. Chem.* 264:1941).

Modification of RNA chains using chemical reagents has been reported in several articles. Specific modifying chemicals that have been used include dimethylsulphate leading to base modification (Bollack et al., (1965) *Bull. Soc. Chim. Biol.* 47:765–784), N-chlorosuccinimide leading to base modification and RNA degradation (Duval and Ebel, (1967) *Bull. Soc. Chim. Biol.* 49:1665–1678; Duval and Ebel., (1966) *C.R. Acad. Sc. Paris* t. 263:1773 series D), N-bromosuccinimide (Duval and Ebel, (1965) *Bull. Soc. Chim. Biol.* 47:787–806), diazomethane leading to methylation of the base and phosphate causing RNA breakdown (Kriek and Emmelot., (1963) *Biochemistry* 2:733), carbodiimide leading to base modification (Augusti-Tocco and Brown (1965) *Nature* 206:683), alkyl halides leading to base and phosphate modification (Ogilvie et al., (1979) *Nucleic Acids Res.* 6:1695) and allyl bromide leading to guanine modification and chain degradation (Bollack and Ebel, (1968) *Bull. Soc. Chim. Biol.* 50:2351–2362). It has been reported that the use of acetic anhydride in DMF results in acylation of cytosine (Keith and Ebel (1968) *C.R. Acad. Sc. Paris* t. 266:1066 series D). Methyl sulphate has been used to modify the bases of an RNA template (Louisot et al., (1968) *Annales de L'institut Pasteur.* 98). The results of such chemical modification reactions of RNA are therefore degradation, base and/or phosphate modification.

Other work has shown the acylation of the base uridine of tRNA (Glu) using benzoic anhydride but not the 2'-OH groups (Cedergreen et al., (1973) *Biochem.* 12:4566–4570). Using benzoic anhydride, phthalic anhydride, N-benzoylimidazole and acetylimidazole Cedergreen demonstrated that there is only one major site of modification of the tRNA and that 1 mole of anhydride reacted with 1 mole of tRNA. The authors conclude that acylation occurred on the base moiety.

The free amino function of the base is often N-acylated when the nucleotide or nucleoside is treated with an anhydride such as acetic anhydride or an acid chloride in anhydrous pyridine. Indeed this method is often used to protect the amino groups of nucleosides (Brimacombe et al., (1968) *Czech. Chem. Commun.* 33:2074; Saneyoshi (1968) *Chem. Pharm. Bull.* 16:1400; Cedergreen et al., (1971) 49:730; Amarnath and Broom., (1977) *Chem. Rev.* 77:183). Furthermore it has been shown that RNA treated with acetic anhydride in dimethyl formamide is specifically modified on the cytosine base and not on the 2'-OH group (Keith and Ebel, (1968) *Biochim. Biophys. Acta.* 166:16–28). It is well known and widely reported that ribonucleotides in pyridine solution exclusively acetylate the base.

The work of Chang and Lee (*Biochemistry* (1981) 20:2657) demonstrated the methylation of RNA using methyl methanesulfonate. Six methylation sites were identified, 5 on the bases and one on the phosphate.

This body of work, taken together, strongly suggests that chemical treatment of nucleic acids would be likely to result in the modification of either the bases or the phosphate with or without RNA degradation. This is not surprising considering the chemical reactivity of these groups. Obtaining 2'-OH regiospecific modification of RNA is the basis for this invention.

(2'-azido-2'-deoxyuridylic acid) has been prepared (Torrence, (1972) *J. Amer. Chem. Soc.* 94:3638–3639). Pyridine-catalysed quantitative examples of acetylation are reported for 3'-hydroxynucleotides (Weber and Khorana, (1972) *J. Mol. Biol.* 72:219; Zhdanov and Zhenodarova, (1975) *Synthesis* 222).

The acetylation procedure was first described by Khorana and co-workers (Stuart and Khorana (1963) *J. Biol. Chem.* 85:2346) who acetylated the terminal 3'-OH group of deoxyribonucleotides and oligonucleotides with acetic anhydride. No modification of the bases was observed unless the acetylation was carried out in the presence of strongly basic solvents such as pyridine or tributylamine (Michelson and Grunberg-Manago, (1964) *Biochem. Biophys. Acta,* 91:92).

Acetylation of a tRNA molecule was carried out by using acetic anhydride. A change in the secondary structure was reported (Knorre, et al., (1965) *Biokhimiya* 30:1218). Modification of 30% of the 2'-OH groups of tRNA was found to destroy its secondary structure. Further work by the same researchers demonstrated that variable acetylation levels of tRNA (Knorre, et al., (1966) *Biokhimya* 31:1181) and polyribo-oligonucleotides (Knorre, et al., (1967) *Biochim. Biophys. Acta* 142:555) could be achieved by use of acetic anhydride and N,N-dimethylformamide. It was also shown that acetylated poly(U) lost its ability to hydrogen bond with poly(A). Acetylated forms of poly(U) and poly(A) were reportedly quite unable to direct polypeptide synthesis in a cell-free system (Knorre, et al., (1967) *Molekul. Biol.* 1:837).

More recently, it has been reported in a publication that mRNA from a cell-free transcription system has been used as a substrate for acetylation (Ovodov and Alakhov, (1990) *FEBS* 270:111). Acetylation of 70–75% of the 2'-OH groups was said to be achieved using the method of Knorre et al. However, results presented in the publication suggest otherwise. FIG. 9 shows no change in mobility indicating that no modification actually took place.

SUMMARY OF THE INVENTION

In a first aspect, the present invention provides a polynucleotide comprising mRNA, rRNA or viral RNA, greater than 25% of the ribose rings of which are covalently modified at the 2'-OH position. The invention does not extend to polynucleotides consisting only of DNA or uses of oligo- or polynucleotides consisting only of DNA.

In a second aspect, the present invention provides a process for producing a modified oligo- or poly-nucleotide, which comprises (i) contacting in a reaction medium RNA comprising an oligo- or poly-ribonucleotide with a reaction system comprising a reactant capable of covalently modifying the 2'-OH position of the ribose rings of the RNA; (ii) reacting the RNA with the reaction system to produce modified oligo- or poly-nucleotide under conditions to achieve covalent modification of greater than 25% of the 2'-OH positions of the ribose rings; and (iii) optionally separating the modified oligo- or polynucleotide from the reaction medium, wherein the reaction medium comprises at least 20% v/v organic solvent and the reaction system is capable of achieving the covalent modification in 1 hour or less. The RNA may be mRNA, tRNA, rRNA, viral RNA, synthetic RNA such as chemically synthesised or in vitro transcribed forms, or any other form of RNA, such as hnRNA and viroid RNA. The RNA may be a mixture of different types of RNA and may be in single- or double-stranded form, linear or circular and even contain internal regions of secondary structure such as is commonly found in tRNA, mRNA and viral RNA. According to the present invention an oligonucleotide generally has a sequence length of up to about 80 bases and a polynucleotide generally has a sequence length of more than about 80, preferably more than about 100 bases. A preferred length for a polynucleotide is at least 1000 bases.

The mRNA may or may not have a cap and/or polyA tail. The mRNA, rRNA, or viral RNA used in the present invention is preferably naturally-occurring. A naturally-occurring RNA according to the present invention typically comprises a nucleotide sequence which is found in nature and which generally encodes a polypeptide having biological activity, or such a nucleotide sequence which is modified, for example to alter in some way the biological activity of the polypeptide encoded thereby. Whilst the naturally-occurring RNA is preferably obtained by transcription from a suitable template, itself usually naturally-occurring, in some cases the naturally-occurring RNA can be obtained synthetically. mRNA according to the present invention does not encompass simple homopolynucleotides (polyA, polyU, polyG and polyC) which can be generated synthetically but are biologically non-functional.

As described in further detail below, other steps in the process may include (iv) using the modified RNA as a template in order to produce a second complementary strand of RNA or DNA, and (v) ligating suitable DNA fragments such as a plasmid vector to the ends of the molecule in order to clone and propagate it. An important aspect of this invention is modification of mRNA and viral RNA since it is of major scientific interest and serves as a good example of the problems encountered when manipulating RNA. The invention further provides methods for obtaining intact full-length copies of mRNA and other types of RNA isolated from cellular sources that demonstrate increased stability in conditions that would otherwise destroy a major fraction of the unmodified RNA.

Modification at the 2'-OH position is preferably substantially regiospecific. Thus, there is preferably substantially no modification of the bases, phosphodiester bonds and/or any other position within the RNA chain other than the 5'-OH and 3'-OH groups. In this way, the polynucleotide retains important properties of the RNA. For example, advantageously, the polynucleotide is preferably modified so that a single strand of the polynucleotide is replicable by a nucleic acid polymerase to generate a second strand of polynucleotide complementary to the single strand.

The extent of modification of the 2'-OH position of the ribose rings is not especially limited, and may vary according to the application of the modified oligo- or polynucleotide. Generally the oligo- or polynucleotide may be modified such that a proportion of the ribose rings are modified at the 2'-OH position, the modification preferably being sufficient to protect the polynucleotide against nuclease degradation, especially against cellular endonucleases and/ or intracellular concentrations of nucleases. The claimed polynucleotide of the present invention has at least 25% of its ribose rings modified at the 2'-OH position. In the other embodiments of the present invention, preferably at least 25%, more preferably at least 50%, and even more preferably at least 75% of the ribose rings are covalently modified. In the most preferred embodiments of the present invention, at least 80%, more preferably 85% of the ribose rings are covalently modified at the 2'-OH position, still more preferably at least 90% and most preferably at least 95% of the ribose rings are covalently modified at the 2'-OH position.

Measuring the Percentage Modification of RNA

Due to the polymeric nature of RNA, it is difficult to measure its molecular weight above 100 nucleotides using mass spectrometry because a large amount of RNA degradation occurs during the analytical process. However, RNA (tRNA) up to 142 nucleotides (Nordhoff et al., (1993) Nucleic Acids Res. 21:3347; Gruic-Sovulj et al., (1997) Nucleic Acids Res. 25:1859; Tolson and Nicholson (1998) Nucleic Acids Res. 26:446) and double stranded DNA up to 500 base-pairs (Bai et al. (1995) Rapid Comm. Mass Spectrom. 9:1172; Taranenko et al., (1998) Nucleic Acids Res.

26:2488; Ausdall and Marshall (1998) Anal. Biochem. 256:220) have been measured using MALDI mass spectrometry (for reviews see; Smith (1996) Nat. Biotech. 14:1084; Murray (1996) J. of Mass Spectrom. 31:1203). Phosphate (Schuette et al., (1995) J. Pharm. Biomed. Anal. 13:1195; Sinha et al., (1994) Nucleic Acids Res. 22:3119) and chemically modified oligonucleotides (Potier et al., (1994) Nucleic Acids Res. 22:3895) have also been measured using mass spectrometry.

Although there is a molecular weight limitation to a few hundreds of nucleotides when using mass spectrometry, it provides a simple, automated means to accurately determine the exact molecular weight and therefore the percentage modification of a polynucleotide. Optimisation relies on a number of factors such as the type of mass spectrometry being carried out (electro-spray, MALDI-TOF etc), the method used to purify the modified RNA from the modification reaction, the size of the polynucleotide, the ionisation matrix used, the method used to remove cations from the RNA, positive or negative ion mode and the voltage strength used (Fenn et al., 1989) Science 246:64). Capillary high performance liquid chromatography can be used prior to mass spectrometry of RNA because desalting and other purification steps are not required prior to ionisation (Taniguchi and Hayashi (1998) Nucleic Acids Res. 26:1481).

To measure the molecular weight and hence the percentage modification of polynucleotides consisting of thousands of nucleotides requires a different approach. In certain situations where it is preferable to measure the percentage modification of the polynucleotide using more precise means a degradative step may be employed followed by an analytical process. It is expected that degradation of the modified polynucleotide using chemical or enzymatic means will, depending on the method used leave the 2'-OH modification attached to the ribose sugar allowing the amount of modification to be established by mass spectrometry or high performance liquid chromatography (HPLC). HPLC and gas chromatography analysis of nucleotides has been described (Gehrke and Patel (1977) J. Chromat. 130:103; Iwase et al., (1975) J. Chromat. 106:213; Kemp et al., (1982) J. Chromat. 241:325).

In order to establish the percentage of nucleotides that are modified, degradation of the polynucleotide should follow the modification reaction. Methods have been described for enzymatic cleavage methods employing ribonucleases RNase T1, RNase A, RNase U2, RNase PhyM, RNase CL3, nuclease S7 and cusativin, chemical cleavage methods using sulphuric acid (Jones et al., (1994) RNA Isolation and Analysis, chapter 3, Bios Scientific Publishers, Oxford) and physical methods using post source decay (Hahner et al., (1997) Nucleic Acids Res. 25:1957; Taniguchi and Hayashi (1998) Nucleic Acids Res. 26:1481; Kirpekar et al., (2000) RNA 6:296).

It will be understood that the 2'-OH modification may inhibit degradation of the polynucleotide. However, by empirically determining the sensitivity of the modified RNA to a range of conditions it should be possible in most cases to select conditions that are suitable for chain cleavage. For example, it has been found that acetylated RNA is readily cleaved by nuclease Bal 31. Whilst alkali cleaves acetylated RNA it also results in acetyl cleavage so unless the amount of cleaved acetyl groups is measured by mass spectrometry (see section entitled 'mass spectrometry of isotopically labelled RNA') acetylated nucleotides will not be detected. For example, acid cleavage of the modified polynucleotide can be used for base sensitive modifications, whilst base cleavage can be used for acid sensitive modifications. It will also be understood that other degradation products such as dinucleotides, trinucleotides etc. will also be suitable for measuring the percentage modification of the polynucleotide. Whether it is the nucleotide, dinucleotide or larger fragments that are being measured, in each case it is the ratio of the number of fragments bearing a modification compared with the number of fragments not bearing a modification that provides the percentage modification.

Other methods that are capable of measuring high molecular weight RNA such as analytical ultracentrifugation to find the sedimentation coefficients (Svedberg units) are imprecise, require large amounts of starting material and are dependent on the conformation of the RNA (for review, see Jones et al., (1994) RNA Isolation and Analysis, chapter 3, Bios Scientific Publishers, Oxford). Despite these drawbacks, analytical ultracentrifugation using denaturing sucrose or isokinetic gradients may be useful to measure very large molecular weight changes in abundant RNA samples.

It is now much more common to measure the molecular weight of polynucleotides using electrophoretic separation in polyacrylamide or agarose gels. Detailed descriptions of the preparation, use and handling of electrophoresis gels are described in several publications (Sambrook et al., (1989) Molecular Cloning: A Laboratory Manual, CSH; Jones (1995) Gel Electrophoresis: Nucleic Acids Essential Techniques, Wiley). Denaturing gels are preferred to non-denaturing gels because they reduce conformational effects providing a means to measure the true molecular weight of the linear polynucleotide (Jones (1995) Gel Electrophoresis: Nucleic Acids Essential Techniques, page 47, Wiley). There are a variety of denaturants that can be used such as DMSO (50–90%), glyoxal (10–30%), formaldehyde (3% w/v), formamide (50–98%), heat (60–80° C.), methyl mercuric hydroxide (3–5 mM), sodium iodoacetate (10 mM), 2-pyrrolidone (5%) and urea (6–8 mM). It is known that incomplete denaturation of the polynucleotide leads to anomalous migration so that more than one denaturing condition may be required such as 8M urea plus 5% pyrrolidone or 8M urea run at 60° C. (Rosenblum et al., (1997) Nucleic Acids. Res. 25:3925) Capillary electrophoresis provides an excellent means to carry out such molecular weight determinations and suitable methods have been described for RNA (Engel and Dieguez-Lucena (1993) Nucleic Acids Res. 21:759).

Comparative measurements of polynucleotide migration between different gels are difficult because the distance migrated is dependent on the buffer used, gel concentration and temperature. Therefore it is preferred that comparisons be made with both molecular weight standards and sample polynucleotides in the same gel. It is also known that certain percentages of the sieving matrix such as polyacrylamide or agarose are optimal for certain lengths of nucleic acids and above a certain percentage of acrylamide or length of polynucleotide (the exclusion limit) separation as a function of length does not occur. Therefore, measurements of the molecular weight should be made within such known limits (Sambrook et al., (1989) Molecular Cloning: A Laboratory Manual, CSH; Jones (1995) Gel Electrophoresis: Nucleic Acids Essential Techniques, Wiley).

It has been found that using a 20 cm 6M urea 5% polyacrylamide gel that a 250 nucleotide acetylated RNA runs approximately 20 mm apart from the non-modified form as a tight band. Therefore, measuring the amount of modification of smaller modifying groups than acetyl (42 daltons) should be feasible. The acetylated RNA also runs at a position predicted to be 100% modified as compared with RNA size markers.

It is common practice to be able to separate in a denaturing sequencing gel DNA polynucleotides differing by as little as 1 nucleotide in a total length of 500 nucleotides i.e. by 0.2% or less difference in length (Sambrook et al., (1989) Molecular Cloning: A Laboratory Manual, CSH.). It is therefore reasonable to expect that accurate measurements can be made for the molecular weight of RNA polynucleotides in their modified and unmodified forms when the modifying group is large, for example 28 daltons for formyl and 42 daltons for acetyl. Measuring the percentage modification with other modifying groups may also be possible providing that the molecular mass increase as a result of the modification is sufficient. For example, halogenation of the 2'-OH group should be readily measured for chlorine (35.4 daltons) and bromine (79.9 daltons) substitution of the 2'-OH group.

Calculating the percentage modification may be carried out by measuring the migration of known RNA size markers in a gel such as a 6M urea 5% acrylamide sequencing gel and plotting migration (mm) versus molecular weight (daltons) to obtain a standard curve. Because the exact, molecular weights of all the markers are known, it is straight forward to graph the relationship between the mobility in the gel versus the known molecular weight of each marker. The percentage modification for an RNA of known length with a known mass for the modifying group can then be readily calculated by comparison with this standard curve.

An alternative means to determine the percentage modification is to use a radioactively labelled reactant such as 14C or 3H acetic anhydride to modify RNA and then determining the molar ratio of radioactive acetyl groups to nucleotides in a known amount of RNA sample. If the molar ratio is 1:1, then 100% of the 2'-OH groups are modified. It will be understood that radioactive isotopes can be incorporated into a wide variety of reagents.

Regiospecificity of the reaction can be determined by subjecting an identical sequence of DNA (or preferably single stranded DNA bearing uracil as a replacement to thymine), to identical reaction conditions as used for RNA. It is expected that the DNA is not substantially modified as measured by incorporation of radioactivity, gel electrophoresis mobility, mass spectrometry, HPLC or any other analytical means used if the reaction is regiospecific for the 2'-OH group.

The modification at the 2'-OH position may be such that the entire OH of the 2'C of the ribose ring is replaced by a reactant group R as in 2'-R or by OR having 2'-OR where the —O— group may or may not originate from the 2'-OH group. Accordingly, the substituent at the 2'-OH position in this case is R or OR respectively. One aim of the modification is to protect the molecule to a significant extent from degradation. Degradation may be a result of nucleases, metal ions and/or high temperatures, high pH or other chemical or physical conditions.

It will be apparent to those skilled in the art that multiple types of substituents exist which are suitable to practice this invention. One set of acyl substituent examples is given here for clarity, where the acyl is joined to the 2'-oxygen as in 2'-O—COR where R can be composed solely of carbon, oxygen and hydrogen atoms in a linear chain arrangement, as in —COCH$_2$CH$_2$CH$_2$CH$_3$, in a branched chain arrangement as in —COC(CH$_3$)$_3$ or in a ring structure as in COC$_6$H$_5$. It will be further understood that hydrogen can be replaced by other atoms as in —COCH$_2$Cl or —COCF$_3$ and that carbon atoms can be joined to another carbon with one or more bonds as in the crotonate —COCH$_2$CH=CHCH$_3$ or one or more oxygen atoms as in the ether —COCH$_2$CH$_2$OCH$_3$ or carbonate —COOCH$_2$CH$_3$ or a combination of both. Furthermore, other atoms such as nitrogen, silicon and sulphur may also be present. A single RNA molecule may bear more than one type of substituent on any of its 2'-OH positions producing mixed substituent RNA chains.

The modified ribose rings may bear at the 2'-OH position a variety of substituents. The substituent may have the formula OR, wherein R is selected from: C1–C10 alkyl, C1–C10 alkenyl, C1–C10 alkynyl, C1–C10 haloalkyl, C1–C10 aminoalkyl, C1–C10 haloalkoxyalkyl, C1–C10 aminoalkoxyalkyl, C6–C14 aryl, C6–C14 alkylaryl, C6–C14 arylalkyl, C6–C14 arylalkenyl, C1–C10 alkanoyl, C1–C10 alkenoyl, C1–C10 haloalkanoyl, C1–C10 dihaloalkanoyl, C1–C10 trihaloalkanoyl, C2–C10 haloformylalkanoyl, C1–C10 aminoalkanoyl, C6–C14 arylalkanoyl, C6–C14 arylalkenoyl, C1–C10 alkoxyalkanoyl, C6–C14 aryloxyalkanoyl, C6–C14 alkylarylalkanoyl, C1–C10 azidoalkanoyl, C1–C10 carboxyalkanoyl, C1–C10 carboxyalkenoyl, C1–C10 carboxyalkynoyl, C6–C14 haloarylalkanoyl, C6–C14 aminoarylalkanoyl, C7–C15 alkylaminoarylalkanoyl, C1–C10 haloalkenoyl, C1–C10 haloalkynoyl, C1–C10 alkylsilanyl, C3–C10 trialkylsilanyl C1–C10 alkoxycarbonyl, C3–C18 alkylthioalkoxyalkoxycarbonyl, C1–C10 alkenyloxycarbonyl, C3–C18 alkoxyalkoxyalkyl, C2–C12 alkoxyalkyl, C2–C12 alkylthioalkyl, C1–C10 alkylsulfonyl, C12–C28 diarylphosphone. In this case R is preferably selected from: methyl, ethyl, vinyl, allyl, ethynyl, 2-chloroethyl, 2-aminoethyl, ethyloxyethyl, methoxymethyl, methylthiomethyl, methoxyethoxymethyl, (2-chloroethyl)oxyethyl, (2-aminoethyl)oxyethyl, phenyl, 4-methylphenyl, benzyl, cinnamyl, formyl, acetyl, propanoyl, butanoyl, pentanoyl, hexanoyl, heptanoyl, octanoyl, nonanoyl, pivaloyl, isobutanoyl, isopentanoyl, carboxyacetyl, chloroformylnonanoyl, 3-carboxypropanoyl, 4-aminobutanoyl, 4-chlorobutanoyl, chloroacetyl, dichloroacetyl, trifluoroacetyl, trichloroacetyl, 3-azidopropanoyl, 4-azidobutyryl acryloyl, propioloyl, crotonoyl, benzoyl, diphenylacetyl, phenoxyacetyl, methoxyacetyl, methoxycarbonyl, 2-(methylthiomethoxy) ethoxycarbonyl, vinyloxycarbonyl, 4-methylbenzoyl, 4-chlorobenzoyl, 2-methylaminobenzoyl, 2-aminobenzoyl, 4-aminobenzoyl, 4-nitrobenzoyl, cinnamoyl, silanyl, trimethylsilanyl, triethylsilanyl, tripropylsilanyl, triisopropylsilanyl, t-butyldimethylsilanyl, 2-chlorophenyl (4-nitrophenyl)phosphono, and methylsulfonyl. Alternatively, the substituent may be R', wherein R' is selected from methyl, ethyl, vinyl, allyl, ethynyl, t-butyl, 2-chloroethyl, 2-aminoethyl, ethyloxyethyl, phenyl, benzyl, fluoro, chloro, bromo, iodo, amino.

Various reactants or reactant combinations may be used, optionally in the presence of a catalyst, to provide these substituents, as described in further detail in the Examples below. Advantageously, the reactant comprises an acid anhydride, an acid chloride, a carboxylic acid, an acyl cyanide, an N-acylimidazole, an alkoxyalkyl halide, an alkylthioalkyl halide, an alkoxyalkoxyalkyl halide, a trialkylsilane halide or a trialkylsilane imidazole, each of these reactants participating in an acylation reaction, silylation or alkoxyalkylation reaction with the RNA. Under these reaction conditions, the reaction medium may further comprise an acylation catalyst. For example, where the reactant comprises an acid anhyride, this may be reacted with the RNA in the presence of a catalyst such as a fluoride ion or amino pyridine. As a further example, where the reactant comprises an acid chloride or N-acylimidazole, the reactant may be reacted with the RNA in the presence of an amino pyridine. As a further example, where the reactant comprises a carboxylic acid, this may be reacted with the RNA in the presence of a dehydrating agent or a catalyst, such as an isocyanide catalyst. A preferred aminopridine catalyst is dimethyl aminopyridine (DMAP). When the RNA is to be formylated, a catalyst is preferably added, especially if the solvent employed is THF, in order to increase the rate of the reaction. Two suitable catalysts for this aspect of the invention are dimethylaminopyridine (DMAP) at 5 mg/ml or more preferably 1-methylimidazole at 160 mg/ml. Both catalysts are known to promote acylation reactions (see *Bull. Soc. Chem. Fr.* (1973) 1021). Mixtures of DMAP (5 mg/ml) and 1-methylimidazole (160 mg/ml) may be employed, preferably in THF. There is prolific gas production when 1-methylimidazole is used as the formylation catalyst. No gas production is observed when DMAP serves as the catalyst. Other acylation catalysts, such as aminopyridines (4-pyrrolidinopyridine, 2-hydroxypyridine), tributylphosphine, may also be employed in this aspect of the present invention.

Alternatives to DMAP, 4-pyrrolinopyridine and 1-methylimidazole catalysts for acylation reaction using acid anhydrides are $TaCl_5$ (Chandrasekhar, et al., (1998) *Tetrahedron Lett.* 39:3263), TMSOTf (Procopiou et al., (1998) *J. Org. Chem.* 63 :2342), $Sc(OTf)_3$ (Zhao et al., (1998) *J. Org. Chem.* 63 :7559), $Bu_3P$ (Vedejs et al., (1993) *J. Am. Chem. Soc.* 115 :3358), $COCl_2$ (Iqbal and Srivastava. (1992) *J. Org. Chem.* 57 :2001), Montmorillonite K-10, KSF (Li et al., (1997) *Chem. Commun.* 1389) and $Cu(OTf)_2$ (Saravanan and Singh. (1999) *Tetrahedron Lett.* 40 :2611).

Various enzymes are capable of transferring acyl groups such as acetyl or benzoate from a suitable donor molecule such as vinyl acetate or vinyl benzoate respectively to an alcohol. Such enzymes may be employed in the present invention. Other activated acyl donors include isoprenyl alkanoates, oxime esters, symmetrical anhydrides or mixed carboxylic-carbonic anhydrides (Guibé-Jampel et al. (1996) *Tetrahedron* 52:4397). Such enzymes include lipases such as those isolated from *Pseudomonas fluorescens* (Boaz. (1989) *Tetrahedron Lett.* 30:2061), *Candida cylindracea* (Holla (1989) *Angew. Chem. Int. Ed. Engl.* 28:220), porcine pancreatic lipase (Guibé-Jampel et al. (1996) *Tetrahedron* 52:4397) and *Mucor miehei*. Such acylation reactions can be either in an aqueous or organic solvent such as tetrahydrofuran, pyridine or DMSO. Organic solvents may be beneficial in that they are capable of dissolving a wide range of molecules (Ciuffreda et al. (1999) *Biorg. Med. Chem. Lett.* 9:1577)

Esterases such as lipases from *Candida albicans, Candida cylindracea* or porcine pancreatic lipase can both add or remove acyl groups (Hennen et al., (1988) J. Org. Chem. 53:4939; Kloosterman et al., (1987) Tetrahedron Lett. 28:2989). Enzymatic hydrolysis can be brought about in aqueous solutions by mixing acylated RNA substrates with suitable esterases in an aqueous buffered solution, an aqueous-organic or organic solution.

Advantages to enzymatic over chemical deacylation are firstly that the buffers and pH are compatible with other enzymes such as reverse transcriptases and secondly that deacylation with ammonia for example may lead to degradation of the RNA chain unless the ammonia is removed or neutralised. By contrast, following enzymatic deacylation the RNA chain would be intact and capable of being reverse transcribed. Indeed, enzymatic deacylation coupled with a second enzyme may provide a robust system for the analysis of RNA. For example, although acetylated RNA is generally a poor template for reverse transcriptase, it is protected against the activity of nucleases. By combining an enzyme capable of deacetylation such as an esterase with a reverse transcriptase in the same reaction tube it may be possible to couple the deprotection of the RNA so that the RNA is then immediately copied into a cDNA form. Therefor, the RNA is not in a deprotected form for any significant length of time. Furthermore, the partially deprotected RNA may be expected to lack secondary structure resulting in full length cDNA forms being made.

It is preferred that the RNA is modified by introducing a formyl group, a silyl group, a halogen, or a group comprising an ether group at the 2'-OH position. Modification using these groups will now be discussed in more detail.

The formyl group (—COH) can be introduced into the 2' position of RNA in a similar manner to acetylation, although any conventional formylation agents and conditions may be employed, provided the required modification of the RNA is not adversely affected. There are several means (see T. W. Greene: (1991) Protective Groups in Organic Synthesis, $2^{nd}$ edition, Wiley Interscience) to introduce formyl groups such as by the use of formic acid (Ringold et al., (1956) *J. Am. Chem. Soc.* 78:816; Hughes et al., (1949) *J. Chem. Soc.* 3347), N-formyl imidazole (Staab et al., (1962) Ann. 655:95), formic anhydride or acetic formic anhydride (Reber et al., (1954) *Helv. Chim. Acta.* 37:45; Zemlicka et al., *Collect. Czech. Chem. Commun.* 27:2784). All of these reagents can be used in the present invention, however the reactant formic anhydride ($C_2H_2O_3$) unlike acetic anhydride ($C_4H_6O_3$) is quite unstable and tends to degrade readily at room temperature. Therefore acetic formic anhydride ($C_3H_4O_3$) which is more stable than formic anhydride is preferably used to carry out the formylation reaction (for review see Strazzolini et al., (1990) *Tetrahedron* 46:1081).

Acetic formic anhydride is not readily available and may be prepared as follows, essentially according to *Fieser and Fieser*, (after Muramatsu et al., (1965) *Bull. Chem. Soc. Japan.* 38:244). 10 g of sodium formate crystals (Aldrich) were ground to a fine powder using a mortar and pestle and then mixed with 8.3 ml of anhydrous ether (Sigma). The ether was dried by mixing 5 g of molecular sieves with 40 ml of diethyl ether and leaving the mixture at room temperature for 1 hr before decanting the ether. To the sodium formate-ether mixture was added 8.87 ml of acetyl chloride (Sigma) in small volumes over 5 minutes whilst maintaining the temperature at 22° C. in a water bath. A slight excess of sodium formate ensures all of the acetyl chloride is consumed. The reaction was mixed with a magnetic stirrer for 5 hr 30 min. at 22° C. and then filtered under suction into a distillation flask. The filter was washed once with 30 ml of anhydrous ether and both ether fractions combined. The ether was removed under a 10–20 mm Hg vacuum using a water pump and then the acetic formic anhydride product distilled at 22° C. and collected by passing the vapour over glass cooled in ice. Warming the reaction mixture to 50° C. during the distillation procedure resulted in a product that was completely unreactive, possibly due to the thermolabile character of acetic formic anhydride. The product remaining in the distillate flask was found to be partially reactive, but was less pure than the distilled product. Therefore the most suitable preparation was to distil at room temperature under 10–20 mm Hg and to collect the distillate on ice. The purified reagent can be stored for at least 3 months at 4° C. or 6 months at −80° C. in a sealed storage vessel without apparent loss of activity.

An alternative formylation reagent is benzoic formic anhydride. Benzoic formic anhydride may be produced by mixing either 6 molar equivalents (1 ml) of formic acid with 1 (1 g) or 2 molar equivalents (2 g) of benzoic anhydride and mixing for 15 minutes at 22° C.

Acyl groups, including formyl and acetyl groups, may be removed from the RNA, if required, in a deprotection reaction. Thus, although acylation endows RNA with a high degree of stability, in certain circumstances it may be preferable to remove the acyl group prior to use. This may be useful for example in increasing hybridisation stability during northern blot analysis. Both acid and alkaline conditions lead to ester bond cleavage but careful titration of the amount of acid or alkali added is required if the RNA polymer is not to be cleaved by the acid or alkali present. For example, adding NaOH to acetylated RNA will rapidly cleave the acetyl ester reinstating the original 2'-OH group which then becomes a target for base catalysed cleavage. In this example, deprotection is closely followed by polynucleotide cleavage, unless the amount of alkali added is sufficient to cleave the acetyl group and neutralise the acetic acid produced. Successful base catalysed deprotection has been achieved using NaOH and ammonium hydroxide ($NH_4OH$). It would be expected that other bases such as KOH or $KHCO_2$ will have a similar result.

Alternatives to acid and base catalysed ester cleavage include potassium cyanide which is a mild transesterification catalyst (Plattner et al., (1972) J. Am. Chem. Soc. 94:8613). Preferably the RNA is incubated in KCN of 60 mM or less, since larger concentrations in some circumstances lead to both acetyl cleavage and polynucleotide breakdown. It is also preferred that the KCN concentration is 1 mM or more, since lower concentrations may in some cases not cleave the acetyl or lead to RNA cleavage. Particularly preferred KCN catalysed acetyl cleavage is as follows: to 5–20 ng of acetylated RNA in 1 µl of water is added 9 µl of methanol and KCN to a final concentration of 10–40 mM. The reaction is incubated for 15–30 min at 22° C. Under these conditions, complete deacetylation can be achieved with a minimum of RNA polymer cleavage.

The chemical stability of acyl groups is in part dependent on the electron withdrawing capability of the acyl group. The more electron withdrawing the acyl group the weaker the ester linkage. For example the chloroacetate ($ClH_2CO_2$—R) is known to be approximately 760 times more labile than the acetate ($CH_3CO_2$—R) (Greene and Wuts. "Protective Groups in Organic Synthesis" $2^{nd}$ edition, pp92, Wiley Interscience). It has been found that RNA modified with the chloroacetate group at the 2'-OH position using chloroacetic anhydride in THF/DMAP, can be purified by ethanol precipitation, but on standing in water at 22° C., the chloroacetate tends to be spontaneously cleaved leading to acidification of the solution. Although haloacetates such as the chloroacetate would be too unstable for many uses such as protection from serum nucleases, they may be useful for certain applications such as northern blotting or reverse transcription. An easily cleaved acyl group may be preferable because it is unlikely that conditions required to cleave the chloroacetate ester would also cause RNA polymer cleavage.

Ester linkages with intermediate lability between the acetate and chloroacetate include 3-phenylpropionate and methoxyacetate which are 50 and 20 times respectively, more labile than the acetate (Greene and Wuts. "Protective Groups in Organic Synthesis" $2^{nd}$ edition, pp92, Wiley Interscience). It is therefore possible to use extremely mild deprotection reactions by using electron-withdrawing acyl groups attached at the 2'-OH position.

It has also been found experimentally that hog liver esterase and porcine liver esterase are not normally suitable for the extensive deacetylation of modified RNA. Furthermore, such crude preparations of esterase contain significant concentrations of RNases necessitating the use of RNase inhibitors such as RNasin in order to measure deacetylation. Another more preferred enzymatic deacetylation procedure for modified RNA uses the enzyme α-chymotrypsin, which recognises and cleaves the 3-phenylpropionate ester at 37° C. (Rigby, (1973) J. Org. Chem. 38:977).

Some strong acylating reagents such as acetyl chloride with extended reaction times may lead to both 2'-OH modification and some non-regiospecific acylation of the base (i.e. an amide bond forming). Amide formation on the RNA may diminish biological properties such as hybridisation and template activity. Following the acylation reaction, any amide bonds on the base may, in some preferred embodiments, be specifically removed without destroying the ester bonds at the 2'-OH. Copper (II) chloride in the presence of glyoxal promotes the chemoselective cleavage of amides over esters (Singh and Ram, J. Org. Chem. (1994) 59:710). Temperatures in the range of 0° C. to 50° C., and pH in the range of 3.5–9 are preferred for this reaction.

Many reagents are capable of halogenating alcohol groups, resulting in the exchange of the —OH for the halogen atom. For example it has been reported that the fluorine atom is similar in size and electronegativity to the 2'-OH group and would therefore be expected to be recognised by nucleic acid polymerases as a suitable template. Replacement of the 2'-OH group of RNA with a halogen atom is a preferred aspect of the present invention. Preferably the halogen atom is fluorine, chlorine or bromine. The present invention preferably achieves halogenation using a non-catalysed system, but any system or reagent may be used, provided that the modification is not adversely affected. The RNA substrate is preferably mixed with halogenating reagent in the presence of an organic solvent. The best results are obtained when water was excluded from the system. Thus, in this aspect of the invention the RNA is preferably dissolved either in DMF, DMSO or other suitable organic solvent. In the presence of approximately 5% or more water, the reaction may be inhibited. It has been shown that halogenated RNA synthesised chemically or by in-vitro transcription using halogenated nucleotide triphosphates has higher resistance to nucleases.

A further preferred group form modifying RNA according to the present invention is a group containing an ether or thioether group. Such groups include alkoxyalkyl groups, alkylthioalkyl groups and alkoxyalkoxyalkyl groups. Preferred groups of this type include methoxymethyl, methylthiomethyl, methoxyethyl, ethoxymethyl, ethoxyethyl, methoxymethoxymethyl, methoxymethoxyethyl, methoxyethoxymethyl, methoxyethoxyethyl, ethoxymethoxymethyl, ethoxymethoxyethyl, ethoxyethoxymethyl, and ethoxyethoxyethyl groups. The method for introducing these groups into the RNA is not especially limited. Preferably the corresponding halides (e.g. chlorides, bromides or iodides) or imidazole derivatives of these groups are employed.

It has been found that MEM chloride is a particularly suitable reagent for the introduction of the methoxyethoxymethyl (MEM is $CH_3OCH_2CH_2OCH_2$—O—R, where R is the 2'-carbon) group at the 2'-OH position of RNA. However, careful choice of solvents may be required so that the modification occurs without RNA chain degradation. For example, low concentrations of MEM chloride in a tetrahydrofuran (THF) solvent may give no detectable RNA modification whilst adding more MEM chloride may lead to RNA chain cleavage, probably as a result of acid formation in the reaction. In contrast, high concentrations of MEM chloride may be required in N-ethyldiisopropylamine (EDPA or Huning's base) (4 µl MEM chloride in 40 µl of EDPA) in order to counteract the basicity of the solvent, otherwise the RNA can be rapidly degraded in EDPA alone. It is therefore preferred to use reaction conditions that do not lead to either acid or base catalysed RNA cleavage. A mixture of EDPA and THF provides good reaction conditions for MEM modification. It is preferred to add between 5–25% EDPA, preferably in THF, with 2.5% v/v of MEM chloride. These reagents are particularly effective for 2'-OH modification.

Other reagents that are suitable for protecting RNA include bromomethyl methyether ($BrCH_2OCH_3$) and chloromethyl methylsulphide ($ClCH_2SCH_3$). These may be used under similar reaction conditions as MEM-Cl.

The reaction incorporating the ether or thioether groups is not especially limited, but is preferably carried out at 22° C. to 60° C. for up to three hours. In some cases this may lead to some RNA degradation, in which case the temperature and/or reaction time may be reduced accordingly. Adding more than 100 ng of RNA to the standard reaction may reduce the extent of modification in a manner approximately proportional to the amount of RNA added. It may thus be advantageous to control the reaction scale in some cases. Some of the MEM modified RNA tends to aggregate and therefore not enter the sequencing gel. This effect has also been seen with RNA modified with acyl groups longer than 5 carbons. Increasing the time of the reaction may lead to reversal of the modification. For example when the reaction is incubated over-night at 22° C., there is less modified RNA compared with a reaction of 3 hrs or 30 minutes. A minimum reaction volume of 120 µl is preferred because it was found that in some cases e.g. in a 40 µl reaction the modification may be incomplete.

An interesting property of MEM-ethers is their sensitivity to Lewis acid catalysts such as $ZnBr_2$, $MgCl_2$, $AlCl_3$, $FeCl_3$, $SnCl_4$ and $TiCl_4$ (Tetrahedron Lett. (1976) 809, 4701, 4705). This has interesting consequences in reverse transcription. Since the reverse transcription contains 1.3 mM $MnCl_2$ or 2.5 mM $MgCl_2$, the MEM groups may be cleaved during the reaction so that the enzyme is copying non-modified or partially MEM modified RNA templates. Both $MnCl_2$ and $MgCl_2$ are commonly used in reverse transcription reactions so that no substantial changes to the standard reaction conditions are required when using MEM modified RNA as a template. MEM modified RNA would provide a simple means to protect the template RNA during shipping, handling and storage whilst deprotection occurs spontaneously during reverse transcription or whenever it is mixed with a Lewis acid catalyst. Thus modification with MEM is particularly preferred in reverse transcription aspects of the present invention.

If it is important to remove the MEM group from the modified RNA without contamination by the metal ions (i.e. the Lewis acid catalyst), solid phase Lewis acid catalysts may be used, so that following deprotection the RNA can be separated from the metal ion simply by separating it from the solid phase (see review by Akelah and Sherrington (1981) Chem. Rev. 81:557). This may be important where a downstream application of the RNA such as reverse transcription is inhibited by the metal ion. A suitable solid phase Lewis acid catalyst is aluminium chloride polystyrene resin.

It is also preferred in the present invention that the RNA is modified by silylation. The modifying silyl group is not especially limited. There is a wide range of silyl groups that may be employed in the present invention. Those bearing a bulky silyl group such as triphenylsilyl may result in low levels of 2'-OH group modification due to steric hindrance between the reagent and the RNA such as the bases. These types of silyl group are less preferred. Preferred reagents are those bearing smaller groups such as trimethylsilyl, triethylsilyl or tripropylsilyl and triisopropylsilyl. However, it is known that of this series, the trimethyl silyl group is relatively unstable and therefore although it may readily react with the RNA leading to high levels of modification, it is not particularly preferred since in some cases it may not be sufficiently stable to provide RNA stability for purposes such as handling and storage. The choice of silylation reagent is dependent on the specificity of the reaction towards the 2'-OH group versus other reactive groups such as the bases, its steric bulk and stability (see Chapter 8, Greene and Wuts "Protective Groups in Organic Synthesis" $2^{nd}$ edition, Wiley Interscience; see also "Silylating Reagents" (1995) Fluka Chemie AG). It should also confer protection from nuclease activity whilst maintaining some biological properties of the RNA such as hybridisation or template activity for polymerases. Alternatively, if the RNA modified with the silylating group is ineffective as either a polymerase template or hybridisation partner, the modifying group may be cleaved (so that the RNA is deprotected) prior to use. Reagents capable of cleaving silyl groups include fluoride ions (stability (see Chapter 2, Greene and Wuts. "Protective Groups in Organic Synthesis" $2^{nd}$ edition, Wiley Interscience; see also "Silylating Reagents" (1995) Fluka Chemie AG).

The organic solvent used in the reaction medium of the present invention preferably comprises an organic base and may comprise an organic solvent in which is dissolved the organic base or, in a preferred embodiment, may be the organic base itself. It is preferred that the reactant is soluble in the organic solvent. In a preferred embodiment the reaction medium further comprises water. In this way RNA to be modified may be conveniently added to the organic solvent as an aqueous solution of RNA. Typical organic solvents include alkanes such as hexane and pentane, pyridine, acetonitrile, dimethylformamide, dichloromethane, acetone, diethyl ether, benzene, chloroform, ethyl acetate, light petroleum, tetrahydrofuran, carbon tetrachloride, dichloroethane, dioxane, carbon disulphide, nitromethane, dimethyl sulphoxide, hexamethylphosphoric triamide and toluene. Typical organic bases include pyridine, triethylamine, trimethylamine, diisopropylethylamine, N,N-diethylaniline, N,N-dimethylaniline, 1,5-diazabicyclo(4,3,0)non-5-ene (DBN) 1,8-diazabicyclo(5,4,0)undec-7-ene (DBU) and N-methylmorpholine. Triethylamine ($(CH_3CH_2)_3N$ is a stronger amine base than pyridine, aniline, diethylamine or trimethylamine but less so than pyrrolidone. It is one of the strongest amine bases. A preferred organic base which acts as a solvent is triethylamine (TEA). Where a catalyst is to be used, it is convenient for the catalyst to be soluble in the organic solvent as well. The water and the organic solvent may form different phases in the reaction medium. For example, the water and the organic solvent may be immiscible with one another and form phases which will separate upon standing. Where there is more than one phase, the RNA may be reacted with the reactant under conditions of phase transfer catalysis.

The amounts of water and organic solvent may be varied and will depend to some extent upon the particular organic solvent/base/catalyst system to be used. Advantageously, the reaction medium comprises at least 50% organic solvent, preferably at least 80%, more preferably at least 90% and more preferably at least 95% v/v. Typically, the ratio of water:organic solvent is in the range 1:50 to 1:10, preferably around 1:20.

When the modification involves formylation of the RNA, the polar solvent, tetrahydrofuran (THF), is preferred to the basic solvent triethylamine because it was found to be less likely to cause RNA chain cleavage when the modification reaction includes a reduced amount of reactant. It is well known that basic conditions lead to RNA cleavage, and RNA left in triethylamine for more than 5 minutes suffers considerable degradation. However, this is not a problem when using reactants such as acetic anhydride in triethylamine because the reaction occurs rapidly thereby protecting the RNA from cleavage. There is a distinct advantage when replacing triethylamine with tetrahydrofuran as the formylation reaction solvent particularly when 0.1 µl or less of acetic anhydride is used per 1 µg of RNA. An additional advantage is that RNA can be precipitated out of tetrahydrofuran more efficiently than from triethylamine, thereby increasing purification yields. Pyridine when used as the solvent instead of THF or TEA led to the reaction proceeding more sluggishly and is therefore not as favoured.

In the absence of a catalyst, the reaction time is generally from 20 to 60 mins. In the presence of the catalyst, the reaction proceeds more quickly, generally being completed within about 20 seconds. With respect to formylation, a 20 µl final reaction volume can be used with 5 µl of acetic formic anhydride to formylate up to 1 µg of RNA, although 100% formylation may not be achieved unless reaction times are prolonged to 1 hr. A smaller volume (1 µl) of acetic formic anhydride may be used to modify 100 ng RNA if reaction times are increased to 1 hr. Reaction times as short as 5 min can be used if 5 µl of acetic formic anhydride is used to modify approximately 100 ng of substrate RNA.

On a vol/vol basis it is found that the ratio of reactant to reaction medium (especially acetic anhydride triethylamine/DMAP) is preferably in the range 1:200 to 1:10, more preferably around 1:20. Too little reactant gives a partial reaction and too much makes the reaction difficult to control.

In certain circumstances, it may be advantageous prior to step (i) of the process of the present invention to use a step of protecting the exocyclic amino groups of the bases of the RNA with a protecting group. After step (ii) a step of deprotecting the exocyclic amino groups by removing the protecting group may be used. In this way, unwanted side-reactions between reactants and the exocyclic amino groups is avoided. For adenine, the protecting group may be benzoyl, N-phenoacetyl or N,N-dimethylaminomethylene. For cytosine, the protecting group may be benzoyl. For guanine, the protecting group may be isobutyl, N-phenoacetyl or N,N-dimethylaminomethylene. Crown 18–6 has been found to be a useful protecting agent to protect the exocyclic primary amino group from acylation, essentially with acetic anhydride (Barrett & Lana, J.C.S. Chem. Commun. 471, 1978).

In one aspect, the RNA which is modified comprises an RNA sample from a cell extract. The RNA sample may be a total RNA sample or a purified RNA, such as an mRNA.

RNA is generally purified in order to study gene expression, determine the size and structure of the mRNA, identify gene products, determine its abundance and to clone it as a DNA copy. Purifying intact and complete copies of RNA is one of the first, critical steps in many molecular biology protocols yet it is also one of the most difficult to carry out successfully. Although there are any number of means by which to purify RNA, all extraction methods involve four steps: (1) inactivation of nucleases, (2) separation of RNA from proteins, (3) separation of the RNA from other macromolecules and (4) concentration of the RNA. To purify the mRNA fraction from the total RNA another step is involved, that is (5) separation of poly (A) tailed RNA from other types.

The choice of the purification system depends on a number of factors such as the source of RNA, its abundance and its ultimate use. One of the most important aspects when isolating RNA is to prevent any degradation during the process. All cells contain enzymes capable of destroying mRNA called ribonucleases which must be removed or rapidly inactivated during the process of mRNA isolation. The ubiquitous nature of 'nuclease' is illustrated by their presence in secretions from finger tips and dust; contamination by any of these will inevitably lead to RNA degradation. Instability of RNA makes it very difficult to isolate it intact, since even a single break in the chain will make this impossible.

RNases (enzymes capable of degrading RNA) are notoriously difficult to inactivate because unlike DNases they do not require cofactors, are heat stable and refold rapidly following heat denaturation. Some tissues such as the pancreas and spleen contain particularly high concentrations of RNases. Unlike DNases, RNases do not require metal ions for activity and therefore cannot be inactivated by metal chelating substances such as EDTA. Some RNases can do without a metal ion for activity because they use the 2'-OH groups instead as a reactive species. Many RNases such as RNase A can survive autoclaving temperatures (120° C.) because the polypeptide readily refolds to assume its original active structure on cooling. This is rarely a property of DNases which become permanently inactivated on heating at moderate temperatures such as 65° C. Due to the extreme difficulty of inactivating RNases, several harsh methods have been developed. These include the use of an alkylating agent such as diethyl pyrocarbonate (DEPC) which permanently modifies the active site of RNase A, or denaturing agents such as guanidinium isothiocyanate. DEPC is unfortunately a suspected carcinogen. Other commercially available RNase inhibitors include ribonucleoside vanadyl complex and angiogenin-binding protein. The former reagent has limited use because it will inhibit the majority of enzymes and the latter is very expensive.

One of the most commonly used methods for purifying RNA are those based on Chirgwin et al., (1979) *Biochemistry* 18:5294–5299 and Chomczynski and Sacchi, (1987) *Anal. Biochem.* 162:156 and useful descriptions of how to correctly handle RNA can be found in Sambrook et al., (1989) *Molecular Cloning: A Laboratory Manual* (2nd Ed.) Cold Spring Harbor University Press, Cold Spring Harbor, N.Y. Many companies also provide RNA isolation kits such as MICRO FAST TRACK™ from Invitrogen, PolyATract® from Dynal, Norway and TRIzol Reagent™ from Gibco BRL of Gaithersburg, USA.

In one embodiment, at least some of the modified ribose rings bear at the 2'-OH position a substituent which is labelled with a label. Useful labels include fluorescent or radioactive labels as well as ligands for antibodies or other proteins, for example biotin, or specific types of metal ions such as tin. Various uses for labelled oligonucleotides or labelled polynucleotides are discussed below.

In a further aspect, the present invention provides a kit for modifying an oligo- or polynucleotide comprising an oligo- or poly-ribonucleotide, which kit comprises (a) an organic solvent; and
(b) a reaction system comprising a reactant capable of covalently modifying the 2'-OH position of the ribose rings of the oligo- or poly-ribonucleotide in the presence of the organic solvent, which reaction system is capable of achieving the covalent modification in one hour or less. The kit may be used to modify an oligo- or polynucleotide which conveniently comprises an aqueous sample. Alternatively, the oligo- or polynucleotide may be present in a non-aqueous solvent.

In a further embodiment there is provided a method for gene expression analysis which comprises obtaining a polynucleotide comprising an mRNA sample modified in accordance with the above process where the RNA sample is from a cell extract. The polynucleotide is analysed, for example, by hybridisation probing. Commonly used methods of gene expression analysis include northern blotting, RT-PCR, dot blotting and in situ hybridisation. These methods require mRNA in an intact form capable of serving as a marker of gene expression. By modifying the 2'-OH group in accordance with the present invention, the extent of degradation of the mRNA is reduced.

In a further aspect, the present invention provides use of an oligo- or poly-nucleotide comprising RNA, a proportion of the ribose rings of which are covalently modified at the 2'-OH position, as a probe. The probe may be labelled, for example, with a fluorescent or radioactive label. For example, modified mRNA may serve as a labelled probe for hybridisation, finding utility, for example, in "biochip" applications used to study gene expression.

Currently, an entire mRNA population is reverse transcribed in the presence of a radioactive deoxynucleotide triphosphate such as $^{32}$P dATP to produce a labelled cDNA probe which is then hybridised to the 'biochip'. In this invention, as described in Example 5, the modified mRNA itself serves as the probe. Probes prepared in this way would have very high specific activities (cpm/µg RNA) and therefore be capable of detecting very small amounts of target DNA or RNA. Alternatively, fluorescent silyl or acyl groups could be used as labelling groups for RNA such as isatoic anhydride (Horner, et al., (1985) J. Organomet. Chem. 282:175).

In a further aspect, the present invention provides a method for the replication of a polynucleotide, which comprises obtaining a polynucleotide comprising modified RNA as described above, and replicating the modified RNA to form a complementary polynucleotide using a nucleic acid polymerase. Because modification of RNA in accordance with the present invention can provide a replicable polynucleotide which is relatively stable to laboratory manipulation, the polynucleotide may be used in a range of applications as a substitute for DNA. The complementary polynucleotide may comprise an RNA, DNA or hybrid or modified forms thereof.

For example, the complementary polynucleotide may comprise a cDNA and the nucleic acid polymerase may comprise a DNA polymerase. Such polymerases are discussed in detail below.

The copying of mRNA into cDNA is an important method for obtaining fully representative copies for use in applications including cDNA cloning, DNA sequencing, protein production for drug screening programs and understanding the function of a particular gene. Conventionally, all require the activity of reverse transcriptase which is associated with many associated problems such as inhibition.

The synthesis and cloning of cDNA involves a complex series of enzymatic steps in order to copy the mRNA into double-stranded DNA and cloning this into a DNA vector. As used herein the term cDNA refers to a complementary DNA molecule synthesised using a ribonucleic acid strand (RNA) as a template. Many approaches are known for cDNA cloning, all have tried to preserve as much of the original sequence as possible (Okayama and Berg, (1982) Mol. Cell. Biol. 2:161, Gubler and Hoffman, (1983) Gene 25:283).

Conventionally, problems can occur at one or more of three stages, 1) mRNA isolation, 2) first strand cDNA synthesis or 3) second strand synthesis. When the mRNA starting material is degraded, incomplete forms of the cDNA are an inevitable result. One application of the present invention is to stabilise the mRNA molecule in order to isolate complete copies of the mRNA. mRNA modified in accordance with the present invention can be used as a template for reverse transcriptase.

obtaining a full length cDNA is one of the most difficult yet important tasks when characterising a gene. Most commonly, cDNA libraries are produced by the complete conversion of a mRNA pool into a cDNA copy (Gubler and Hoffman (1983) Gene 25:263–269) however the most common outcome is to produce an incomplete representation of the starting mRNA.

Methods to isolate full length cDNA copies of mRNA include: RACE (rapid amplification of cDNA ends) first described in 1988 as a method to isolate full length cDNAs using PCR (Frohmann, et al., (1988) Proc. Natl. Acad. Sci. USA 85, 8998–9002). Related methods have been reviewed (Schaefer, (1995) Anal. Biochem. 227:255–273). Although these methods can be successful for retrieving the 5' and 3' ends of single cDNA molecules, it requires considerable skill and depends in large part on the abundance of the mRNA and can only be done one at a time.

The method for the replication of the polynucleotide, according to the present invention, may further comprise a step of ligating to a vector a single- or double-stranded polynucleotide comprising the polynucleotide and the complementary polynucleotide. In this way, molecular cloning procedures may be accomplished using modified RNA according to the present invention.

In this aspect of the present invention, it is preferred that the RNA is modified by formylation. Formylated RNA serves as an excellent template for reverse transcriptases. However, the optimum re action conditions differ from those used for RNA. The most important difference is the divalent metal cation present in the reaction. Although MULV will reverse transcribe formylated RNA in the presence of $MgCl_2$ e.g. at either 2.5 or 5 mM final concentration, it is preferred that the metal ion is manganese. Manganese is known to alter the specificity of many DNA polymerases such that their template specificity is relaxed. For example, reverse transcriptases will readily copy DNA templates and DNA-dependent DNA polymerases can use RNA templates in the presence of manganese ions. This may explain the enhanced template activity of formylated RNA in the presence of manganese ions. The Mn concentration is not especially limited, but the most preferred (optimum) Mn concentration is 1.2–1.4 mM. The reaction is less effective (with little cDNA product detected) with buffers containing in excess of 3 mM or less than 0.1 mM manganese. Mixtures of the two types of metal ion may also be employed in the present invention, such as a mixture of 1 mM manganese and either 0.5 or 1 mM magnesium ions.

A final Tris-HCl buffer (pH 8.4 at 22° C.) concentration of 200 mM yields more cDNA product than the 50 mM specified in the product protocol of Superscript II (Life Technologies, USA). Increasing the Tris-HCl concentration further to 350 mM slightly reduces the cDNA yield.

Enzymes which can be used successfully in this aspect of the invention include Superscript II (Life Technologies), MULV RNase H+ (Promega), MULV RNase H− (Promega), Expand (Roche Molecular Biochemicals) and HIV-1 reverse transcriptase (Amersham Pharmacia). A mixture of Supercript II and AMV (Invitrogen, USA) may also be used successfully.

Formylated BMV RNA can be reverse transcribed in the presence of DMSO (e.g. 10% DMSO) which is known to reduce nucleic acid secondary structure, or in a Tris-HCl buffer pH 7.5 (e.g. at 22° C.) or in KCl (e.g. 150 mM).

In a further aspect, the present invention provides, a method for producing a double-stranded oligo- or polynucleotide from a template, which comprises contacting the template with a plurality of mononucleotides comprising UTP, dTTP and/or dUTP, ATP and/or dATP, GTP and/or dGTP, and CTP and/or dCTP, in the presence of a nucleic acid polymerase and optionally a template primer under conditions to polymerise the mononucleotides to form a nucleic acid strand complementary to the template, wherein the template comprises an oligo- or polyribonucleotide, a proportion of the ribose rings of which oligo- or polyribonucleotide are covalently modified at the 2'-OH position to bear a substituent which enables replication of the template by the nucleic acid polymerase.

It has been surprisingly found that when the ribose rings of the oligo- or polyribonucleotide are modified in accordance with the present invention, the oligo- or polyribonucleotide produced thereby is capable of acting as a template for one or more of a variety of nucleic acid polymerases. Nucleic acid polymerases within the scope of the present invention include DNA polymerases, RNA dependent polymerases and RNA dependent RNA polymerases.

Among the RNA-dependent DNA polymerases are Superscript™ II (MMLV reverse transcriptase RNase H−), MMLV reverse transcriptase, HIV reverse transcriptase, AMV reverse transcriptase, RAV-2 reverse transcriptase, human T-cell leukemia virus type I (HTLV-I) reverse transcriptase, bovine leukemia virus (BLV), Rous Sarcoma virus (RSV), Tth DNA polymerase, Tfl DNA polymerase, Bst polymerase, Taq DNA polymerase, Thermoscript, C.therm polymerase, displaythermo-RT or Klenow DNA polymerase.

Among the DNA-dependent DNA polymerases are DNA polymerase I;-Klenow fragment; T4 DNA polymerase; T7 DNA polymerase; Taq DNA polymerase, Tli DNA polymerase, Pfu DNA polymerase; Vent™ DNA polymerase; Deep Vent™ DNA polymerase; Bst DNA polymerase; Tth, Pfu Turbo™, Pfu(exo−), Pwo, Pyra™, Tfu, KlenTaq, Taq2000™, AmpliTaq Stoffel fragment, Sequenase™, Tma, Vent®(exo−), Deep Vent®(exo−) or a DNA polymerase purified from *Thermosipho africanus, Thermotoga maritima, Desulfurococcus mobilis, Methanobacterium thermoautotrophicum, Methanothermus fervidus, Pyrococcus furious, Pyrodictium occultum, Sulfolobus acidocaldarius, S. solfataricus, Thermococcus litoralis* or *Thermoplasma acidophilum.*

Among the RNA-dependent RNA polymerases are Q beta replicase, and those derived from *E. coli* phage f2, R17, MS-2 or ø6, or from a virus family selected from the bromoviridae, flaviviridae, picornaviridae, potyviridae, tobamovirus, tombusviridae, leviviruses, hepatitis C-like viruses, and picornaviruses or from polio virus, yellow fever virus, tobacco mosaic virus, brome mosaic virus, influenza virus, reovirus, myxovirus, rhabdovirus and paramyxovirus.

Nucleic acid polymerases may be classified into four overlapping groups. Classification is based on the type of template copied (RNA or DNA) and the type of complementary nucleic acid strand that is produced (RNA or DNA). Although in vivo, nucleic acid polymerases have discrete activities, in vitro specificity for the template and the substrate mononucleotides is less stringent. As one example, in vitro certain DNA dependent DNA polymerases such as Taq and Tth DNA polymerase can also behave as RNA dependent DNA polymerases. Specificity depends in part on the buffer conditions, presence of metal ions and the type of mononucleotide triphosphate present. Lastly, many mutant forms of polymerases are known (for one example see; Gao et al., (1997) Proc. Natl. Acad. Sci (USA) 94:407) that are less specific with respect to the template strand copies and the type of complementary strand produced. Accordingly, some enzymes appear in more than one of the above lists.

Preferably, the oligo- or poly-nucleotide is modified by (i) contacting in a reaction medium RNA comprising an oligo- or poly-ribonucleotide with a reactant capable of covalently modifying the 2'-OH position of the ribose rings of the RNA; (ii) reacting the RNA with the reactant to produce modified oligo- or poly-nucleotide under conditions to achieve covalent modification of a proportion of the 2'-OH positions of the ribose rings; and (iii) optionally separating the modified oligo- or polynucleotide from the reaction medium, wherein the reaction medium comprises an organic solvent.

In a further aspect, the present invention provides a method for amplifying an oligo- or polynucleotide, which comprises:
(1) providing the oligo- or poly-nucleotide as a template comprising an oligo- or poly-ribonucleotide, a proportion of the ribose rings of which oligo- or poly-ribonucleotide are covalently modified at the 2'-OH position;
(2) producing from the template a double-stranded oligo- or poly-nucleotide in accordance with the above method;
(3) melting each double-stranded oligo- or poly-nucleotide to form single strands;
(4) annealing the template primer to the single strand having the nucleotide sequence of the template and annealing a second primer to the strand complementary thereto to form primed single strands;
(5) contacting the primed single strands with the plurality of mononucleotides in the presence of the nucleic acid polymerase to form double-stranded oligo- or poly-nucleotides;
(6) optionally repeating steps (3) to (5) until sufficient amplification is achieved; and
(7) harvesting the amplified oligo- or poly-nucleotide in single- or double-stranded form.

This method is typically used in a polymerase chain reaction.

In a further aspect the present invention provides a method for amplifying an oligo- or polynucleotide, which comprises:
(1) providing the oligo- or poly-nucleotide as a template comprising an oligo- or poly-ribonucleotide, a proportion of the ribose rings of which oligo- or poly-ribonucleotide are covalently modified at the 2'-OH position;
(2) amplifying the template in a nucleic acid sequence based amplification (NASBA), and
(3) harvesting the amplified oligo- or poly-nucleotide in single- or double-stranded form, wherein the step of amplifying the template including producing from the template a double-stranded oligo- or poly-nucleotide in accordance with the above method.

There is further provided a method for diagnosing in a subject a disease indicated by the presence or absence of a target nucleotide sequence, which method comprises:
(a) obtaining an oligo- or poly-nucleotide sample from the subject;
(b) amplifying the oligo- or poly-nucleotide in accordance with either of the above methods to form an amplified oligo- or poly-nucleotide; and
(c) analysing the amplified oligo- or poly-nucleotide for the target nucleotide sequence.

The subject may be a human, an animal or a plant.

In a further aspect, the present invention provides use of a nucleic acid polymerase for the production of a nucleic strand complementary to a template for the nucleic acid polymerase, wherein the template comprises an oligo- or polynucleotide comprising an oligo- or polyribonucleotide, a proportion of the ribose rings of which oligo- or polyribonucleotide are covalently modified at the 2'-OH position to bear a substituent which enables replication of the template by the nucleic acid polymerase.

The nucleic acid polymerase may be any of those nucleic acid polymerases defined above.

In a further aspect, the present invention provides use of an oligo- or polynucleotide as a template for a nucleic acid polymerase, wherein a proportion of the ribose rings of which oligo- or polyribonucleotide are covalently modified at the 2'-OH position, to bear a substituent which enables replication of the template by the nucleic acid polymerase.

Either of these uses relate to, for example, reverse transcription or use in a polymerase chain reaction, including RT-PCR.

In a further aspect, the present invention provides a kit for producing a nucleic acid strand complementary to an oligo- or polynucleotide comprising an oligo- or polyribonucleotide, which kit comprises:
(a) a nucleic acid polymerase;
(b) a reaction system for modifying the oligo- or polynucleotide to form a template for the nucleic acid polymerase in which a proportion of the ribose rings of the oligo- or poly-ribonucleotide are covalently modified at the 2'-OH position to bear a substituent which enables replication of the template by the nucleic acid polymerase;
(c) optionally a plurality of mononucleotides comprising UTP, dTTP and/or dUTP, ATP and/or dATP, GTP and/or dGTP, and CTP and/or dCTP; and
(d) optionally a buffer for the nucleic acid polymerase.

Typically, the reaction system comprises:
(i) an organic solvent preferably comprising an organic base; and
(ii) a reactant capable of covalently modifying the 2'-OH position of the ribose rings of the oligo- or polyribonucleotide in the presence of the organic solvent.

The kit may be used for a variety of applications including reverse transcription to produce, for example, full length cDNA, a kit for producing a template for SELEX, a kit for NASBA, a kit for RT-PCR, a kit for ligase chain reaction, a kit for transcription mediated amplification, a kit for producing a template for sequencing, or a target for hybridisation.

The kits optionally further comprise appropriate buffer systems depending on the use to which the kit is to be put and the specificity of the nucleic acid polymerase which is required.

In a further aspect, the present invention provides a method for replicating an oligo- or polynucleotide, which comprises:
(1) providing the oligo- or polynucleotide as a template comprising an oligo- or polyribonucleotide, a proportion of the ribose rings of which oligo- or polyribonucleotide are covalently modified at the 2'-OH position;
(2) producing from the template a double-stranded oligo- or polynucleotide in accordance with the above method;
(3) ligating the double-stranded oligo- or polynucleotide into a vector; and
(4) replicating the vector in a host.

In a further aspect, the present invention provides a method for replicating an oligo- or polynucleotide, which comprises:
(1) providing the oligo- or polynucleotide as a template comprising an oligo- or polyribonucleotide, a proportion of the ribose rings of which oligo- or polyribonucleotide are covalently modified at the 2'-OH position;
(2) ligating the template into a vector;
(3) producing from the template in the vector a double-stranded oligo- or polynucleotide in accordance with the above method; and
(4) replicating the vector in a host.

In a further aspect, the present invention provides a method for replicating an oligo- or polynucleotide, which comprises:
(1) providing the oligo- or polynucleotide as a template comprising an oligo- or polyribonucleotide, a proportion of the ribose rings of which oligo- or polyribonucleotide are covalently modified at the 2'-OH position;
(2) producing from the template a double-stranded oligo- or polynucleotide in accordance with the above method;
(3) obtaining from the double-stranded oligo- or polynucleotide the nucleic acid strand complementary to the template;
(4) ligating the nucleic acid strand into a vector; and
(5) replicating the vector in a host.

According to each of these methods, modified RNA according to the present invention may be used in a cloning procedure.

Although cloning of DNA is well known and commonly carried out (Sanbrook et al., (1989) Molecular Cloning: A Laboratory Manual, CSH), the following alterations may be expected to enhance cloning of modified RNA. In particular, the following alterations of the basic protocol would be expected to provide longer cDNA inserts.

The RNA modification reaction (example 6 and others) may also lead to the modification of the 5'-phosphate group of the RNA substrate in addition to the 3'-OH group and 2'-OH groups. In the case of mRNA which has a common 5'CAP structure it would be expected that the CAP is also modified. In order to allow cloning of the modified RNA into a vector it is necessary to remove both the CAP and the 3' terminal nucleotide.

Alternatively for RNA strands with no CAP structure direct removal of the modified 5'-phosphate group can be carried out either with shrimp or calf alkaline phosphatase, it has been found that acetylated RNA with a 5'-triphosphate structure, as is common to RNA polymerase derived synthetic RNA strands, can be dephosphorylated using shrimp alkaline phosphatase and rephosphorylated with T4 polynucleotide kinase (Sambrook et al., (1989) Molecular Cloning: A Laboratory Manual, CSH).

The CAP structure is commonly removed by either an enzymatic (Jones et al.,(1994) in RNA Isolation and Analysis. Bios. Oxford p77) or chemical procedure (Stahl et al., (1989) in *Nucleic Acids Sequencing: A Practical Approach.* IRL Press, Oxford p137). The 3' modified nucleotide can be removed by the brief exposure to 3' exonucleases such as a snake venom phosphodiesterase (Crotalus durissus). Alternatively the 3' exonuclease activities of T4 DNA polymerase or Klenow fragment DNA polymerase could be exploited.

To enhance the ligation of single stranded nucleic acids into either a single or double stranded DNA vector the following procedure may be used. T4 DNA ligase will not ligate single stranded nucleic acids, therefore a region of double stranded nucleic acid is produced at each end of the cloning site. The restriction enzyme Hga 1 produces a 5 nucleotide 5' overhang and BstX1 produces a 4 nucleotide 3' extension and these are used in conjunction with appropriate cloning vectors to produce ligation sites for the single stranded nucleic acid insert. Inserts can either be ligated with DNA ligase or alternatively with RNA ligase.

A double stranded form of the insert can be produced in two ways: firstly by transforming appropriate $E.coli$ hosts and allowing the host polymerases to produce the second strand; and secondly in vitro by extending from the free 3'-OH group of the vector or oligonucleotide primers with enzymes such as AMV reverse transcriptase, T4 DNA polymerase, T7 DNA polymerase or Klenow fragment DNA polymerase. The addition of single stranded DNA binding protein may improve the efficiency of polymerisation. Subsequent addition of T4 or Tth, Pfu DNA ligase to the reaction joins the vector and insert improving transformation efficiency.

It will be evident to those skilled in the art that many alternative methods exist to create cDNA libraries such as those employing oligo dT, random primers, linkers, adaptors and RNaseH.

Appropriate $E.coli$ hosts may include those that have reduced nuclease activity such as mutants for recB, recC, sbcB, nei, nfi, xth, nfo, hsd and/or those genotypes that increase the stability of clone inserts such as recA, recj, sbcC, umuC and uvrC.

In a still further aspect, the present invention provides use of a poly-nucleotide comprising mRNA or viral RNA, a proportion of the ribose rings of which are covalently modified at the 2'-OH position, in a hybridisation reaction.

In accordance with this aspect of the invention it has been surprisingly found that RNA modified in accordance with the present invention it is still capable of hybridising with nucleic acid. Because modified RNA is more stable to degradation than its unmodified counterpart, problems of degradation of RNA during and before analysis are avoided. There is no longer any need for extreme measures to be used to prevent RNA degradation such as those involving the use of ultra-clean working environments, or expensive inhibitors of RNases.

Typically, the hybridisation reaction comprises a hybridisation between a probe and a template comprising the poly-nucleotide, which may comprise a mixture of oligo- and poly-nucleotides such as those involved in a gene expression analysis.

Alternatively, the hybridisation reaction may comprise a hybridisation between a template and a probe comprising the poly-nucleotide.

The probe or the template may be immobilised to a solid phase such as a hybridisation membrane, a bead, a particle, a slide, a sheet, a gel, a microtitre strip, tube, fibre or capillary.

The solid phase may be made of substances such as nitrocellulose, agarose, acrylamide, cellulose, latex, nylon, polystyrene, polycarbonate, polypropylene, PVDF (polyvinylidene fluoride), polytetrafluroethylene, a silica-based material, a glass, a metal alloy, gold, a magnetic material or a paramagnetic material The hybridisation reaction may comprise a blotting process typically using any one of the above solid phases.

The probe or template may be attached to another molecule or group of molecules. It is frequently desired that the probe or the template is labelled with a label, which may be a fluorescent label, a radioactive label, and enzyme, a ligand or an affinant for such a label. Fluorescent labels for carbohydrate labelling are described in U.S. Pat. No. 6,048,707. The molecules or group of molecules may itself comprise the label in the sense that the group of molecules is capable of causing a detectable reaction or capable of binding a detectable entity. The molecule or group of molecules may comprise a peptide, a poly-peptide such as an antibody, an enzyme, an affinity partner such as protein A or streptavidin, a receptor protein, a ligand such as biotin, dinitrophenyl, digoxigenin or other hapten or lectin, or a label such as fluorescein, rhodamine, Texas red, cy-5, TAMRA or a pigmented chromogenic, chemiluminescent or coloured marker.

The probe may comprise a branched DNA (bDNA) probe.

In a further embodiment, the poly-nucleotide may be bound to a third molecule such as an antibody-alkaline phosphatase conjugate.

The poly-nucleotide may comprise an antisense agent for use in an antisense hybridisation reaction for example in vivo.

In accordance with a further use, the poly-nucleotide has a specific binding affinity to a ligand and the hybridisation reaction comprises a hybridisation between the poly-nucleotide and a target comprising the ligand.

Typically, the RNA comprises a ribozyme.

In a further aspect, the hybridisation reaction comprises a ligase chain reaction (LCR). LCR requires four specific oligonucleotides, DNA ligase and a DNA template. Typically, it relies upon the hybridisation of two template-specific oligonucleotides next to each other such that the 5'-phosphate of one adjoins the 3'-OH of the other. The two oligonucleotides are then ligated by a ligase and this ligated product serves itself as a template for further rounds of ligation in the presence of two further oligonucleotides complementary to the first two oligonucleotides. Because initiation of LCR can only occur when a specific DNA template is present, LCR serves as an effective means for assay of such a template. According to the present invention, the template comprises RNA modified as described above.

In a further aspect, the hybridisation reaction comprises a nuclease protection assay in which unhybridised poly-nucleotides are digested typically with a single stranded nuclease such as Si nuclease or RNase T1, and the remaining poly-nucleotide is analysed, usually by gel electrophoresis.

Nuclease protection assays thereby provide a means to quantitate mRNA abundance and to match the positions of exons, introns and 5' transcription start sites.

In a further aspect, the solid phase comprises a biochip. When the probe comprises the modified RNA typically labelled with a label, a starting mRNA population can be used to probe the biochip directly, following modification. Because there are no enzymatic steps required to incorporate the label, the quantification of the mRNA transcript is improved. Alternatively, the target may comprise the modified RNA immobilised on discrete locations of the biochip or, alternatively, on discrete beads or particles. Because of a reduction in degradation of the RNA, gene expression analysis is improved.

In a further aspect, the probe is immobilised and comprises oligo- (dT), whereby the template is purified from contaminants such as DNA. In this way, mRNA, for example, modified in accordance with the present invention can be sorted from the bulk of total RNA and/or DNA by means of its poly(A) tail. Hybridisation occurs between the modified poly(A) and the immobilised oligo(dT).

The modified RNA may also be used for diagnosis based on the presence or absence of a specified nucleotide sequence.

In a further aspect, there is provided a method for hybridising an oligo- or poly-nucleotide with a modified poly-nucleotide comprising mRNA, rRNA or viral RNA, a proportion of the ribose rings of which are covalently modified at the 2'-OH position, which method comprises contacting the oligo- or poly-nucleotide with the modified poly-nucleotide under hybridisation conditions.

This method advantageously further comprises obtaining the modified poly-nucleotide by (i) containing in a reaction medium mRNA, rRNA or viral RNA with a reactant capable of covalently modifying the 2'-OH position of the ribose rings of the RNA; (ii) reacting the RNA with the reactant to produce modified poly-nucleotide under conditions to achieve covalent modification of a proportion of the 2'-OH positions of the ribose rings; and (iii) optionally separating the modified polynucleotide from the reaction medium, wherein the reaction medium comprises an organic solvent. Preferably, the reaction medium comprise at least 20% v/v organic solvent, more preferably at least 50%, still more preferably at least 80%, more preferably at least 90% and especially at least 95% organic solvent. The organic solvent advantageously comprises an organic base.

In a further aspect, the present invention provides a kit for modifying a polynucleotide comprising mRNA, rRNA or viral RNA, for use in a method according to claim 28 or claim 29, which kit comprises
(a) an organic solvent; and
(b) a reactant capable of covalently modifying the 2'-OH position of the ribose. rings of the mRNA, rRNA or viral RNA in the presence of the organic solvent, wherein the reactant is labelled with a label.

In all of the aspects of the present invention, dialysis may be employed in post reaction clean up. Dialysis is a well known method to separate molecules based on size. Due to the generally small volumes of the modification reaction (20–100 $\mu$l) it is preferred to make use of specialised dialysis units (Mini Slide-A-Lyzer, Cat. 69550T, Pierce, USA) that are adapted to these volumes. Membranes with a molecular weight cut-off of 3500 daltons are preferred. Dialysis therefore offers a simple and suitable means for post-reaction clean-up in the present invention.

Mass Spectrometry of Isotopically Labelled RNA

MALDI-TOF mass spectrometry provides a means to measure the mass of molecules within a fraction of a dalton. Isotopic variants exist for many common elements found in biomolecules such as nitrogen, carbon, and hydrogen. Although some isotopes are radioactive, many are quite stable. For example deuterium is an isotopic variant of hydrogen having a mass of 2 daltons. Reagents containing deuterium (D) or carbon-13 (C-13) such as acetic anhydride are available commercially and therefore provide a simple means to modify the 2'-OH group of RNA with an isotopic label. For example, the acetyl group (—$COCH_3$) has a mass of 43 daltons, whilst the deuterated form (—$COCD_3$) has a mass of 46 daltons. The 3 dalton difference in mass per acetyl group becomes even more significant when multiplied by the total number of acetyl groups per RNA molecule. For example a RNA molecule of 1000 nucleotides would have a mass 42,000 (—$COCH_3$) or 45,000 (—$COCD_3$) daltons greater than the non-modified form. The difference in mass between the two acetyl forms provides a means to label or tag two populations of RNA molecules. When mixed, the two acetylated forms of the RNA could be identified because each has a unique mass. Currently, gene expression studies are carried out by labelling cDNA copies of mRNA with fluorescent groups such that cDNA from tissue A is red and tissue B blue, the two cDNA populations are then mixed and hybridised to a biochip cDNA or oligonucleotide target. The proportion of red versus blue cDNA hybridised to each target provides a means to measure gene expression in the two tissue samples. The disadvantage is that it is necessary to make a cDNA copy of the mRNA, a process inevitably leading to quantitative error and the sensitivity is limited by the number of fluorescent groups incorporated. Using the mRNA itself as the probe offers many advantages, not least in terms of simplicity but more importantly because the assay remains quantitative because no cDNA forms are involved. In this procedure according to the present invention, two populations of RNA derived from tissue A and B, each modified with a chemical group differing from the other by at least one isotopic atom at the 2'-OH group, mixed and then hybridised to a target such as those commonly used for biochips and then the proportion of each type of RNA may be determined by mass spectrometry. For methods employing mass spectrometry or RNA degradation and mass spectrometry see 'Measuring the percentage modification of RNA'.

Due to the large and variable size of the RNA hybridised, it may be difficult to employ MALDI-TOF to determine its molecular weight. Therefore two types of degradative reactions could be used to reduce its size. Firstly the RNA could be degraded by nucleases such as Bal 31 which can degrade both RNA and acylated RNA. The result would be a collection of monomer ribonucleotides each with a molecular weight determined by the acetyl group attached. Therefore the monomer will have a molecular weight of +42 or +45. The exact proportion of each of the monomer types allows the proportion of the original RNA from tissue A or B to be determined. The advantages of carrying out the degradation are two fold. Firstly there is an amplification of signal, for example if the RNA under study was 1000 nucleotides in length, after degradation the relative concentration of the analyte would increase 1000 fold. Secondly, the analyte would be of a defined size depending on the base attached to the ribose. Therefore from each degradative procedure, four product monomers would result, representing U, C, G and A. Each of these would exist in two forms, so in total 8 peaks from each degradation reaction would result and provide a means to compare the relative expression levels of the transcript in tissue A and B.

A potentially simpler procedure may be, for example, to acylate two pools of RNA with normal or isotopic forms of acyl groups as described above, carry out the hybridisation and then cleave the acyl groups from the RNA. This procedure may or may not lead to the RNA being degraded and degradation is not of great importance. Any number of procedures may be used to cleave the acyl group (see T. W. Greene: (1991) Protective Groups in Organic Synthesis, $2^{nd}$ edition, Wiley Interscience) such as ammonia, cyanide, alkali or an esterase. In the case of ammonia, it would be expected that the product of the deacylation reaction of the normal/deuterated acetyl or formyl groups would be ammonium acetate (Mr 77.08 or 80.08) or ammonium formate (Mr 63.06 or 66.06). The relative amount of each ammonium salt for the acetate (77.08 or 80.08) or formate (63.06 or 66.06) would be proportional to the amount of the RNA deriving from tissue A or B that had hybridised to the biochip cDNA or oligonucleotide target.

The present invention may be used in a number of further applications including research applications and medical applications, as set out below.

Research Applications

RNA Shipping, Handling and Storage

Purified RNA samples are currently transported in dry ice or in a desiccated form at room-temperature. Dry ice is both bulky, heavy and expensive to transport whilst desiccated RNA is difficult to resuspend fully in water. RNA must be handled by experienced technicians otherwise there is a high risk of contamination by ribonuclease. Storage requires bulky and expensive −80° C. freezers to ensure the integrity of the RNA. RNA modified with acyl groups is stable for several days or longer at 37° C. and is very ribonuclease resistant. These properties make modified RNA an attractive means to ship, handle and manipulate RNA.

Analysis of RNA Structure and Function In situ Hybridisation

The in situ hybridisation procedure relies on maintaining, in an intact form, viral and cellular RNA especially mRNA in order to serve as a hybridisation partner for a RNA labelled probe. By examination of the localisation of the labelled probe, it is possible to identify specific tissues or cells where a particular gene is expressed. This procedure relies on both the target cellular RNA and the probe RNA being maintained in a largely intact form, otherwise hybridisation will not occur. Utility for the present invention may be found by stabilising both the target and probe RNA such that they are not degraded as is common for unmodified RNA.

(1) The tissue sections that normally contain the target RNA could be treated prior to hybridisation by one or more reagents as have been described in examples 1–32. However, unlike examples 1–32, the target RNA would be treated in an unpurified form in situ with other cellular components such as the cell membranes, DNA and proteins. In this way, the entire RNA population is modified and therefore stabilised throughout the in situ hybridisation process.

(2) The normal form of the probe used for in situ hybridisation is a riboprobe produced by in vitro transcription and composed of a radioactively or fluorescently labelled single-stranded RNA. Such probes are liable to destruction at any point during the in situ procedure. Following the in vitro transcription reaction, the ribo-probe could be treated in a manner as described in one of the examples 1–32 in order to stabilise it against destruction. Such modified ribo-probes would retain their ability to interact in a specific manner with the target RNA. Alternatively, such modified ribo-probes could be used as probes for any number of hybridisation procedures such as northern and Southern blotting, chromosome mapping probes or any procedure which requires such probes.

RNA Analysis Methods

Many techniques have been developed such as primer extension, S1 nuclease mapping and the RNase protection assay which rely on intact RNA as a substrate for analysis. Degradation of the RNA will result in false quantitation of RNA abundance or localisation of the structural features of the mRNA such as the 5' CAP site. Modification of the starting RNA to be analysed (primer extension) or the probe to be used for the analysis (S1 nuclease mapping) would lead to improved accuracy of the results.

RNA Molecular Weight Markers and Standards

Molecular weight markers composed of RNA find use for calibrating northern blots and other procedures that separate RNA according to its size such as mass spectrometry. Commonly, RNA markers of discrete sizes are produced by an in vitro transcription reaction. However such RNA frequently becomes degraded during the separation procedure. In this invention, such discrete RNA molecules are treated in such a way as to maintain their intactness throughout the separation procedure.

Currently, nucleic acid standards for use in diagnostic kits for RNA viruses are restricted to DNA or RNA copies of the sequence of interest. The standard serves as an internal control for RNA integrity, purification efficiency and quantity. DNA standards are not good internal controls because they do not have the same physical characteristics as RNA, whilst RNA standards are frequently degraded either during shipping or during processing. Modified RNA according to this invention, remains in its protected state throughout the purification process and would therefore be expected to be less degraded. It is also protected during shipping, storage, handling and when mixed with blood but is additionally protected during later stages of RNA purification and cDNA synthesis.

Sequencing

There are two common methods for sequencing RNA, nuclease digestion and Maxam-Gilbert methods. The second method, employing reverse transcriptase would benefit from a modified RNA that is stabilised allowing greater quantities of cDNA and therefore sequencing product to be made. MALDI-TOF analysis of longer sequencing products is currently severely limited by degradation occurring to the DNA polynucleotide. It has been found that RNA polynucleotides are less prone than DNA to degradation during MALDI-TOF analysis (Nordhoff et al., (1993) Nucleic Acids Res. 21:3347). Modified RNA copies of RNA sequencing products could provide a robust material for analysis. Such modified RNA would be expected to be less degraded during handling or ionisation during MALDI-TOF analysis thereby providing improved results.

Detection of Polymorphisms

Differences in sequence between two or more polynucleotides can be can be detected by differences in the secondary structure adopted by single strands. Changes in the sequence can alter the secondary structure of the nucleic acid because hairpins and other regions of base-pairing are sensitive to such changes (Hayashi (1991) PCR Methods and Applications 1:34). It is possible to detect alterations in secondary structure and therefore sequence changes using several methods such as single strand conformational polymorphism (SSCP), denaturing gel electrophoresis (DGGE) or cleavage fragment length polymorphism (CFLP™, U.S. Pat. No. 5,422,253). In each case a gel is used to detect the labelled single-stranded nucleic acid. Although single-stranded DNA is frequently used for such analysis, RNA may also be used (Brow et al., (1996) Focus, Life Technologies 18:2). One of the limitations of using RNA has been the sensitivity to degradation during the process, either during manipulation or gel electrophoresis. Modified RNA would offer two advantages over native RNA. Firstly it is more easily handled and less likely to be degraded. Secondly, the 2'-modifications alter the secondary structure of the polynucleotide in a manner specific to the modification. For example acetyl and benzoyl modified RNA adopt different secondary structures from each other and from native RNA. Therefore modified RNA would offer new possibilities for the detection of mutations based on structure. Specifically, modified RNA could be used as a novel substrate for CFLP™ cleavage reactions because it would be expected that cleavage patterns would be significantly altered from native RNA.

Medical Applications

Modified RNA may interact with a target in two distinct ways. Firstly by hydrogen bonding (base-pairing) with a hybridisation partner (e.g. antisense oligonucleotides) or secondly by virtue of its secondary structure (e.g. aptamers). In either case, the modified RNA can find utility for therapeutics or diagnostics

Therapeutics

Any therapeutic molecule (such as antisense nucleic acids) administered should ideally have the following properties; (i) be resistant to in vivo degradation, (ii) be capable of crossing the cell membrane (i.e. show lipophilic properties), (iii) interact specifically and efficiently with the target molecule or cellular machinery, (iv) have a low toxicity and immunogenicity. By careful choice of the type of RNA modification it should be possible to meet many or all of these requirements. For example, a 2'-aliphatic chain would increase the lipophilic nature of the molecule whilst preventing degradation from RNases and retaining the ability to interact with a target.

Types of therapeutic molecules that could benefit in some way from the 2'-modification of RNA could include inhibitory molecules such as antisense nucleic acids and aptamers. Other types could be molecules with catalytic activity such as RNA enzymes (ribozymes) or RNA encoding specific peptides such as mRNA for use in gene therapy or nucleic acid vaccines.

Ribonuclease P

Ribonuclease P can be used to target the cleavage of an RNA molecule containing specific sequences (U.S. Pat. No. 5,168,053; WO 92/03566). The utility for ribonuclease P includes in vitro analysis of sequences and therapeutic applications. However, these uses are limited by the ease with which the RNA is degraded (PCT WO 93/01286). RNA modified at the 2'-OH position according to this invention has increased resistance to ribonuclease degradation and therefore offers improvements over current practice.

Ribozymes

A catalytic RNA is called a ribozyme. It is capable of various reactions such as self cleavage or cleavage of a defined sequence in a heterogeneous RNA. In this case, therapeutic activity could be associated with it if, it cleaved for example the HIV RNA genome. Other activities include binding to specific ligands with high affinity. An in vitro procedure has been designed to select RNA molecules with specific enzymatic functions. Modification of the 2'-OH group of such RNA molecules could endow it with greater stability towards nucleases or indeed new enzymatic function.

Antisense

Antisense are sequences complementary to the sense strand of a mRNA and can consist of RNA, DNA or modified nucleic acids. They interfere with the normal regulation and function of mRNA in such a way that the amount of protein synthesis is reduced. Through the interaction with the target RNA, protein translation is physically blocked or, RNaseH activity is triggered leading to the destruction of the target RNA. Such interference can have therapeutic effects if for example, viral mRNA sequences are targeted. Some of the theoretical advantages of such antisense therapy is their highly specific binding to target molecules and low toxicity.

Modified RNA antisense molecules might be expected to have enhanced activity compared with natural nucleic acids because they are more stable in vivo and/or are more lipophilic so that they enter the cell more readily.

Enzyme Inhibitors and Other Specific Binding Interactions

The present invention further provides use of an oligo- or poly-nucleotide having a specific binding affinity to a ligand for binding specifically to a target comprising the ligand, wherein the oligo- or poly-nucleotide comprises RNA greater than 25% of the ribose rings of which are covalently modified at the 2'-OH position.

RNA aptamers selected by the SELEX procedure could be used in vivo to inhibit the activity of key enzymes associated with a pathogenic organism such as reverse transcriptase or proteases of HIV. SELEX (Systematic Evolution of Ligands by Exponential Enrichment) can in theory, by starting with a sufficiently large pool of random RNA sequences, be used to select RNA molecules with any number of specificities. For example RNA can be selected that is specific to the epidermal growth factor (EGF) or other hormones thus providing a potential therapeutic agent for blocking the activity of such hormones.

During the SELEX procedure, 2'-$NH_2$ groups 2'-F groups, 2'-methyl and 2'-O-methyl groups as ribonucleotides may be incorporated into the RNA chain by T7 RNA polymerase. See Gerard, et al., (1974) *Biochemistry* 13:1632; Jellinek, et al., (1995) *Biochemistry.* 34:11363; Pan, et al., (1995) *Proc. Natl. Acad. Sci. USA* 92:11509; Green, et al., (1995) *Chem. Biol.* 2:683; Green, (1995) *J. Mol. Biol.* 247:60; Lin, et al., (1994) *Nucleic Acids Res.* 22:5229.

It has been shown that injection into animals of double stranded RNA which is complementary to cellular mRNA sequences can specifically interfere with the biological activity of the mRNA. The interference activity is far superior to either single stranded sense of anti-sense RNA. Such double RNA interference molecules have been called RNAi, Tabara et al., (1998) *Science* 282:430–431; Kennerdell and Cartew, (1998) *Cell* 95:1017–1026). As an alternative to double stranded RNA which might be expected to be rapidly degraded in a cellular environment, modified double stranded RNA could be used as RNAi molecules. These would be expected to have an equal biological activity as unmodified forms but be active for prolonged periods thereby improving their efficacy. Other than research applications, RNAi holds promise for therapeutic and other medical applications.

Diagnostics

Modified RNA can be used in a labelled form (e.g. radioactive or fluorescent labels) as a probe to monitor gene activity including the following applications, 'biochip' diagnostics, RT-PCR, northern and Southern blotting, RNase protection, or any application where specific base-pairing is required between the probe and target.

Important diagnostic applications include the purification and detection of infectious agents from biological samples such as blood or cerebral spinal fluid. Those infectious agents such as viruses with RNA genomes are preferred. There are many medically important RNA viruses such as HCV, HIV, polio, Japanese encephalitis virus, yellow fever, Russian tick borne encephalitis, Dengue and West Nile virus. Modifying the 2'-OH groups of single stranded or double stranded RNA viruses endows additional stability therefore reducing the chance of accidentally degrading the analyte during manipulation and provides a straightforward means to introduce a label to aid analysis. It would also provide a means to purify the viral RNA from a body fluid and then subsequently, detect it as part of a diagnostic test or kit.

Related uses include the detection of virus transcripts that are important diagnostic indicators of latent virus infection.

For example, a DNA or RNA virus integrated into the hosts genome as a DNA copy will generate RNA transcripts. Such transcripts indicate the presence of an active and functional viral genome. Examples include HIV, a RNA virus, or polyomavirus, a DNA virus. Modified RNA copies of these transcripts could serve as indicators of both the presence of the virus and its activity. A specific example includes detecting the presence of HIV following anti-viral drug therapy where blood titres of the virus can drop below detectable levels. In this case, one reliable means to detect latent infection is to quantify the numbers of HIV transcripts produced from chromosomal copies within the infected host cells.

Labelled RNA with novel functions such as aptamers that can, like monoclonal antibodies bind to specific ligands, may be used as probes to localise a particular ligand within, for example a cell or tissue. Medical imaging would be one such application for this technology. Suitably modified RNA that can bind a tumour marker for example would aid in the localisation of a cancer cells within the body or serve as an early indicator of cancer.

Microorganism Testing

Detection of rRNA sequences is frequently used in a diagnostic process to identify pathogenic bacteria such as mycobacteria. The rRNA sequence is reversed transcribed using rRNA specific primers and the first strand cDNA amplified by one of several methods such as polymerase chain reaction (PCR) Eisenach et al., (1990) Journal of Infectious Diseases 161:977–981, 1990, nucleic acid sequence based amplification (NASBA), (U.S. Pat. No. 5,409,818), transcription mediated amplification (TMA) (WO 88/10315) or isothermal amplification, ligase chain reaction (LCR) (Iovannisci et al., (1993) Molecular and Cellular Probes 7:35–43, strand displacement amplification (Spargo et al., (1993) Molecular and Cellular Probes 7:395–404), and Q beta replicase (An et al., (1995) Journal of Clinical Microbiology 33:860–867). It will be apparent that the stabilisation or immobilisation of the rRNA by 2'-OH modification will improve detection using any of these methods because the rRNA is less likely to be degraded either during purification from the clinical sample or during transport, handling and reverse transcription.

Various publications describe the use of rRNA as a diagnostic tool for detection of pathogens such as Mycobacterium and Helicobacter (Oksanen et al., (1999) J. Pediatr. Gastroenterol. Nutr. 3:252; Kurabachew et al., (1998) J. Clin. Microbiol. 36:1352; Wondimu and Ryon. (1992) J. Clin. Microbiol. 30:2295; U.S. Pat. No. 5,925,518). These methods all rely on reverse transcription of rRNA, followed by a detection step which may involve hybridisation with a probe, or more commonly an amplification step such as PCR or NASBA.

The stabilisation of rRNA by 2'-OH modification prior to reverse transcription would be expected to have two effects. Firstly, since rRNA has a great deal of secondary structure, modification with for example, acylating reagents would reduce potential blocks to reverse transcription and secondly the rRNA would be less likely to be accidentally degraded during manipulation because it is in a nuclease resistant form. These effects would be expected to improve the sensitivity and reproducibility of pathogen detection.

BRIEF DESCRIPTION OF THE DRAWINGS

The invention will now be described in further detail, by way of example only, with reference to the following Examples and the accompanying drawings, in which:

FIG. 7 shows gel electrophoretic behaviour of RNA acetylated for different reaction times;

FIG. 8 shows gel electrophoretic behaviour of RNA modified in the presence and absence of catalyst;

FIG. 9 shows electrophoretic behaviour of RNA treated in accordance with prior art and modified in accordance with the invention;

FIG. 10 shows the results of performing the methods described by Wang et al.

EXAMPLE 1

Figure 1:
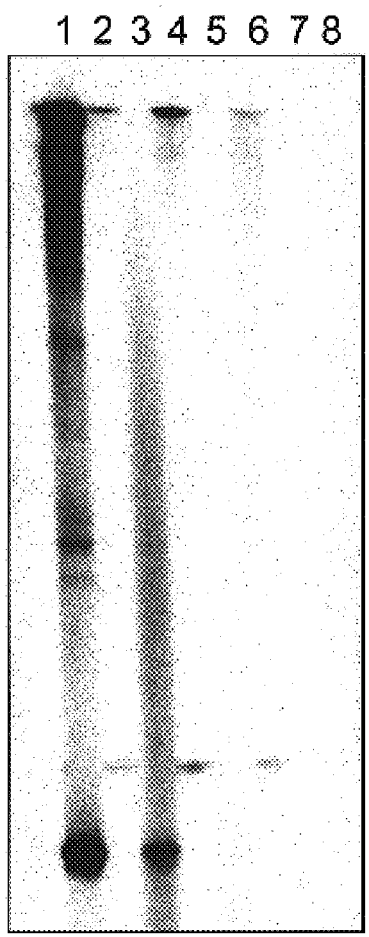
FIG. 1 shows a sequencing gel demonstrating enhanced stability of modified RNA according to the invention.

Acylation of Total RNA Followed by mRNA Selection

The procedure for the modification of mRNA could be one of several. However a preferred method is as follows. The tissue such as 1 g of mouse skeletal muscle is dissected and immediately snap-frozen in liquid nitrogen and then ground under liquid nitrogen with a mortar and pestle. Further tissue and cellular disruption is then made by standard means such as homogenisation using a Waring blender (Waring Commercial of Gateshead, England), in the presence of guanidine isothiocyanate and phenol commercially available as TRIzol reagent (Gibco BRL). Alternatively, tissue culture cells from a 3.5 cm tissue culture plate can be homogenised in 1 ml of TRIzol reagent by passing them repetitively through a pipette. Following a 5 minute incubation at room temperature, 0.2 ml of chloroform was added per 1 ml of TRIzol reagent and shaken for 15 seconds. Following centrifugation at 12,000×g for 15 minutes at 4° C. the upper aqueous phase was removed and mixed with 0.5 ml of isopropanol per 1 ml of TRIzol reagent in a fresh tube. The samples were incubated for 10 minutes at room temperature and centrifuged again at 12,000×g for 10 min at 4° C. The pellet was washed with 1 ml of 75% ethanol per 1 ml TRIzol reagent, allowed to dry and redissolved in 0.2 ml water. The total RNA solution, comprised of 1–5 mg of tRNA, rRNA and mRNA fractions, is then added to 4 ml tetrahydrofuran containing (12 mg; 98 μmoles) 1-methylimidazole as catalyst and then 200 μl (1.96 mmoles) of acetic formic anhydride was added and mixed vigorously on ice for 1 minute then the reaction was allowed to proceed at room temperature for 2 minutes. The reaction was then terminated by addition of three reaction volumes of ethanol followed by mixing with a vortex for 5 seconds. Modified RNA was removed from the reactants and solvent using one of several methods. The preferred method was to ethanol precipitate the modified RNA by adding sodium chloride to a final concentration of 0.3 M and spinning in a centrifuge for 15 minutes at 14 000×g at 4° C. (Sambrook et al., (1989) Molecular Cloning: A Laboratory Manual, CSH.) or Microcon-50 spin-column purification (Amicon, USA) as described or another method that allows such purification. The modified RNA can then be used for any number of applications such as northern blotting or mRNA purification. The process of mRNA purification from the total acylated fraction will now be described.

The acylated mRNA fraction is separated from the acylated total RNA by means of the poly(A) tail common to all mRNA molecules. A PolyATract® isolation system from Promega, USA was used as follows. One milligram of total RNA is diluted into a final volume of 2.43 ml of water and incubated at 65° C. for 10 minutes. Then 10 µl of biotinylated-oligo(dT) probe is added with 60 µl of 20×SSC to the RNA solution and allowed to cool to room temperature over 30 minutes. The biotinylated-oligo(dT) probe-mRNA complex was mixed with 0.5 ml (0.5×SSC) of streptavidin paramagnetic particles and incubated for 10 minutes at room temperature, then washed in 0.1×SSC (4×1.5 ml). The mRNA fraction was then eluted by mixing the biotinylated-oligo(dT) probe-mRNA complex in 1 ml of water, removing the particles and collecting the aqueous phase. The acylated mRNA thus prepared is suitable for applications including but not limited to cDNA library synthesis, northern blotting and in vitro protein translation. A yield of 30 µg mRNA from 1 mg of total RNA starting material is expected.

EXAMPLE 2

Acylation of Purified mRNA

A sample of tissue such as 1 g of mouse skeletal muscle is immediately snap-frozen in liquid nitrogen and then ground under liquid nitrogen with a mortar and pestle then transferred to a 10 ml centrifuge tube. Further tissue and cellular disruption is then made by standard means such as homogenisation using a Waring blender (Waring Commercial, Gateshead, England), in the presence of guanidine isothiocyanate and phenol commercially available as TRIzol reagent from Gibco BRL. Following a 5 minute incubation at room temperature, 0.2 ml of chloroform was added per 1 ml of TRIzol reagent and shaken for 15 seconds. Following centrifugation at 12,000×g for 15 minutes at 4° C. the upper aqueous phase was removed and mixed with 0.5 ml of isopropanol per 1 ml of TRIzol reagent in a fresh tube. The samples were incubated for 10 minutes at room temperature and centrifuged again at 12,000×g for 10 minutes at 4° C. The pellet containing the total RNA fraction was washed with 1 ml of 75% ethanol per 1 ml TRIzol reagent, allowed to dry and redissolved in 0.2 ml water.

The mRNA fraction is separated from non-polyadenylated RNA by any number of methods such as the PolyATract® isolation system from Promega, USA which was used as follows. One milligram of total RNA is diluted into a final volume of 2.43 ml of water and incubated at 65° C. for 10 minutes. Then 10 µl of biotinylated-oligo(dT) probe is added with 60 µl of 20×SSC to the RNA solution and allowed to cool to room temperature over 30 minutes. The biotinylated-oligo(dT) probe—mRNA complex was mixed with 0.5 ml (0.5×SSC) of streptavidin paramagnetic particles and incubated for 10 minutes at room temperature, then washed in 0.1×SSC (4×1.5 ml). The mRNA fraction was then eluted by mixing the biotinylated-oligo(dT) probe-mRNA complex in 0.2 ml of water, removing the particles with the magnetic stand and collecting the aqueous phase.

To 0.1–1 µg of mRNA in 1 µl of water was added 20 µl of triethylamine containing a catalytic quantity (60 µg; 490 nmoles) of 4-dimethylaminopyridine (DMAP) and then 1 µl (9.8 µmol) of acetic anhydride was added. The solution was mixed vigorously using a vortex for 5 seconds and the reaction allowed to proceed for 60 seconds at room temperature (22° C.). The reaction was then terminated by addition of three reaction volumes of ethanol or methanol followed by mixing with a vortex for 5 seconds. Modified RNA was removed from the reactants and solvent using one of several methods. The preferred method was to dilute the mixture into a final volume of 400 µl of water which was then added to a Centricon-50 spin-column (Amicon, USA) and centrifuged for 15 minutes at 3000 g or until the filter was dry. The filter was then washed by addition of 400 µl of water and again spun for 15 minutes at 3000 g. The modified RNA was recovered by inverting the cup containing the filter in a fresh centrifuge tube and spinning it for 60 seconds at 3000 g. Recovery volumes were typically 5–15 µl and recovery yields >95%.

EXAMPLE 3

Halide Ion-catalysed Acetylation Reaction

The specificity and amount of mRNA acetylation can be improved by the addition of halide ions such as fluoride ions. Between 100 ng to 1000 ng of purified mRNA was mixed with a solution containing 30 nmol tetrabutylammonium fluoride (TBAF) or tetrabutylammonium iodide (TBAI), 10 µmol of acetic anhydride and tetrahydrofuran (THF) or triethylamine (TEA) serving as the solvent to bring the final volume to 20 µl. The reaction is allowed to proceed for 2 to 30 minutes at room temperature. Alternatively, pivalic anhydride or benzoic anhydride may be substituted for the acetic anhydride as the acyl donor (Beaucage and Ogilvie, (1977) Tetrahedron Lett., 1691). Alternatively 10 µl of one of the acylating reagents, acetic-formic, propanoic, butyric, pentanoic, hexanoic, heptanoic, octanoic or benzoic anhydrides was added instead of acetic anhydride. All other reaction and purification methods were identical. The unreacted components were removed either by ethanol precipitation (Sambrook et al., (1989) Molecular Cloning: A Laboratory Manual, CSH) or Microcon-50 spin-column purification (Amicon, USA) as described.

EXAMPLE 4

Aminopyridine-catalysed Acylation Reaction

Described is the catalytic acylation of alcohols with an acid anhydride involving triethylamine and the hypernucleophillic acylation catalyst aminopyridine such as 4-pyrrolidinopyridine. To a solution of 1 µg of RNA in 1 µl of water was added 60 µg of 4-pyrrolidinopyridine in 20 µl triethylamine(TEA) and then 10 µmol of an acid anhydride such as acetic-formic, acetic, propanoic, butyric, pentanoic, hexanoic, heptanoic, octanoic or benzoic anhydrides was added. The reaction was mixed and allowed to proceed at room temperature until acetylation was complete (2 minutes to 30 min), (Hofle and Steglich, (1972) Synthesis 619; Steglich and Hofle, (1969) Tetrahedron Lett. 4727; Hassner, et al., (1978) Tetrahedron 34:2069). Excess components of the reaction were removed either by ethanol precipitation (Sambrook et al., (1989) Molecular Cloning: A Laboratory Manual, CSH) or Microcon-50 spin-column purification (Amicon, USA) as described.

EXAMPLE 5

RNA Labelling with a Fluorescent or Radioactive Group

The modifying chemical used to react with the 2'-OH group could include a radioactive label such as 14C, tritium, (3H) or a fluorescent marker such as fluorescein or rhodamine, as a means to label the molecule at multiple positions. Suitable labelled reactants include 14C- or 3H-acetic anhydride and are used a follows. To 1 µg of mRNA was added 20 µl of triethylamine containing (60 µg; 490 nmol) DMAP and 500 µCi of 14C (100–124 µCi/mmol) acetic anhydride (Amersham, UK).

The unreacted components including the radiolabelled acetic anhydride were removed either by ethanol precipitation (Sambrook et al., (1989) Molecular Cloning: A Laboratory Manual, CSH) or Microcon-50 spin-column purification (Amicon, USA) as described. The specific activity of the labelled RNA is quantified by TCA precipitation. The purified radiolabelled mRNA is suitable for a variety of purposes such as a hybridisation probe.

EXAMPLE 6
DMAP-catalysed Acylation Reactions

To 0.1–1 µg of mRNA in 1 µl of water was added 20 µl of triethylamine containing a catalytic quantity (60 µg; 490 nmoles) of 4-dimethylaminopyridine (DMAP) and then 1 µl (10 µmoles) of acetic anhydride was added. The solution was mixed vigorously using a vortex for 5 seconds and the reaction allowed to proceed for 60 seconds at room temperature (22° C.). The reaction was then terminated by addition of three reaction volumes of ethanol or methanol followed by mixing with a vortex for 5 seconds. Modified RNA was removed from the reactants and solvent using one of several methods. The preferred method was to dilute the mixture into a final volume of 400 µl of water which was then added to a Centricon-50 spin-column (Amicon, USA) and centrifuged for 15 minutes at 3000 g or until the filter was dry. The filter was then washed by addition of 400 µl of water and again spun for 15 minutes at 3000 g. The modified RNA was recovered by inverting the cup containing the filter in a fresh centrifuge tube and spinning it for 60 seconds at 3000 g. Recovery volumes were typically 5–15 µl and recovery yields >95%.

Alternative acetylating reagents were used with the same protocol except a maximum of 200 ng of RNA was used per reaction. In each case 10 µmol of the acylating reagents from the list, acetic-formic, propanoic, butyric, pentanoic, hexanoic, heptanoic, octanoic or benzoic anhydrides was added instead of acetic anhydride. All other reaction and purification methods were identical.

EXAMPLE 7
Chloroacetic Anhydride Reactions

To 0.1–1 µg of mRNA in 1 µl of water was added 20 µl of triethylamine containing a catalytic quantity (60 µg; 490 nmoles) of 4-dimethylaminopyridine (DMAP) and then 1 µl (4.8 µmol) of chloroacetic anhydride was added. The solution was mixed vigorously using a vortex for 5 seconds and the reaction allowed to proceed for 60 seconds at room temperature (22° C.). The reaction was then terminated by addition of three reaction volumes of ethanol or methanol followed by mixing with a vortex for 5 seconds. Modified RNA was removed from the reactants and solvent using one of several methods. The preferred method was to dilute the mixture into a final volume of 400 µl of water which was then added to a Centricon-50 spin-column (Amicon, USA) and centrifuged for 15 minutes at 3000 g or until the filter was dry. The filter was then washed by addition of 400 µl of water and again spun for 15 minutes at 3000 g. The modified RNA was recovered by inverting the cup containing the filter in a fresh centrifuge tube and spinning it for 60 seconds at 3000 g. Note, the chloroacetyl modification is labile in water at room temperature, therefore storage in acidified solutions such as pH 3–6 at −80° C. are preferred. Chloroacetyl modified RNA can not be detected using conventional urea-acrylamide sequencing gels.

EXAMPLE 8
DMAP-catalysed Acid Chloride Reactions

To 0.1–1.0 µg of mRNA in 1 µl of water was added 20 µl of triethylamine containing a catalytic quantity (60 µg; 490 nmoles) of 4-dimethylaminopyridine (DMAP) and then 1 µl (3.5 µmol) of a solution of 25% acetyl chloride in toluene was added. The solution was mixed vigorously using a vortex for 5 seconds and the reaction allowed to proceed for 60 seconds at room temperature (22° C.). The reaction was then terminated by addition of three reaction volumes of ethanol or methanol followed by mixing with a vortex for 5 seconds. Modified RNA was removed from the reactants and solvent using one of several methods. The preferred method was to dilute the mixture into a final volume of 400 µl of water which was then added to a Centricon-50 spin-column (Amicon, USA) and centrifuged for 15 minutes at 3000 g or until the filter was dry. The filter was then washed by addition of 400 µl of water and again spun for 15 minutes at 3000 g. The modified RNA was recovered by inverting the cup containing the filter in a fresh centrifuge tube and spinning it for 60 seconds at 3000 g. Recovery volumes were typically 5–15 µl and recovery yields >95%. Either haloacetic anhydride, dihaloacetic or trihaloacetic anhydride or haloacetyl, dihaloacetyl or trihaloacetyl chloride or bromide may also be used as a substitute for chloroacetyl anhydride. However, the presence of more than one halo atom in the acetyl group significantly increases its lability.

EXAMPLE 9
Condensation Reactions Between Carboxylic Acid and RNA

In order to promote the esterification process, dehydrating agents such as N,N'-dicyclohexylcarbodiimide (DCC) are used. 1 µg of mRNA (6 pmol) was dissolved in 10 nmol at carboxylic acid containing 11 nmol dicyclohexylcarbodiimide (DCC) 1 nmol of 4-pyrrolidinopyridine and ether or dichloromethane was added to bring the final volume to 50 µl. The reaction was allowed to proceed at room temperature until esterification was complete (20 min–6 hrs). The carboxylic acids used can be benzoic, acetic, diphenylacetic and mesitoic (Hassner and Alexanian, (1978) *Tetrahedron Letters* 4475). The nucleic acid fraction of the reaction was purified either by ethanol precipitation (Sambrook et al., (1989) *Molecular Cloning: A Laboratory Manual*, CSH) or Microcon-50 spin-column purification (Amicon, USA) as described In order to improve the solubility of the RNA it can be dissolved in 10 µl of either dimethyl formamide or dimethyl sulphoxide before adding it to the reaction.

EXAMPLE 10
t-Butyl Isocyanide-catalysed Acylation with Carboxylic Acid

The use of isonitrile reagents such as t-butyl isocyanide in the esterification of alcohols with carboxylic acids (Rehn and Ugi, (1977) *J. Chem Research* (M) 1501–1506). 3.5 µg mRNA (6 pmol) was dissolved in a solution containing 5 nmol carboxylic acid, 15 nmol t-butyl isocyanide and either ether or dichloromethane to bring the final volume to 50 µl. The reaction was allowed to proceed at room temperature until esterification was complete (approximately 3 hrs). The carboxylic acids used can be, but are not restricted to acetic, diphenylacetic and mesitoic. The nucleic acid fraction of the reaction was purified either by ethanol precipitation (Sambrook et al., (1989) *Molecular Cloning: A Laboratory Manual*, CSH) or Microcon-50 spin-column purification (Amicon, USA) as described. In order to improve the solubility of the RNA it can be dissolved in 10 µl of either dimethyl formamide or dimethyl sulphoxide before adding it to the reaction.

EXAMPLE 11
Use of Phenoxyacetyl Chloride Reagents

RNA (1 µg; 6 pmol) in 1 µl water was added to 20 µl of THF containing 10 µmol of phenoxyacetyl chloride. The reaction was allowed to proceed at room temperature for 30 min (see tetrahedron Lett. (1968) 4273). The nucleic acid fraction of the reaction was then purified either by ethanol

EXAMPLE 12
Use of Levulinic Acid Reagents

1 μg (1.7 pmol) of RNA was dissolved in 10 μl of dimethyl formamide and then dioxan containing 3.4 nmol of levulinic acid, 3.4 nmol of DCC and 100 μg of DMAP was added and mixed. The reaction was allowed to proceed for 24 hr at room temperature (Tetrahedron Lett. (1982) 2615). The unreacted components were removed from the levulinate ester RNA either by ethanol precipitation (Sambrook et al., (1989) *Molecular Cloning: A Laboratory Manual,* CSH) or Microcon-50 spin-column purification (Amicon, USA) as described.

The levulinate group can subsequently be removed by two alternative methods. Method (1). By the addition of 47.7 μg of sodium borohydride (NaBH$_4$) to a 50 μl solution containing 10 μl water and 40 μl of dioxan and the levulinate ester RNA. The pH is brought to 5 by the addition of acetic acid and the reaction allowed to proceed at room temperature for 6 hr. Method (2). 1 μg of the levulinate RNA was treated with 10 μl of 10 mM hydrazine hydrate in pyridine-acetic acid (4:1 vol/vol) (van Boom and Burgers, *Tetrahedron Letters* (1976) 4875). In both cases the mRNA was recovered by ethanol precipitation (Sambrook et al., (1989) *Molecular Cloning: A Laboratory Manual,* CSH). In order to improve the solubility of the RNA it can be dissolved in 10 μl of either dimethyl formamide or dimethyl sulphoxide before adding it to the reaction.

EXAMPLE 13
TBAF-catalysed Silyl to Hydroxyl Replacement

The reaction leads to the direct replacement of a 2'-O-silyl group with the original hydroxyl group when carried out in the presence of fluoride ion. Between 100 ng to 1000 ng of silyated mRNA in 10 μl of dimethyl formamide was mixed with a solution containing 150 nmol tetra-(n-butyl) ammonium fluoride (TBAF) and tetrahydrofuran (THF) serving as the solvent to bring the final volume to 50 μl. The reaction is allowed to proceed for 24 hours at room temperature. The unreacted components were removed either by ethanol precipitation (Sambrook et al., (1989) *Molecular Cloning: A Laboratory Manual,* CSH) or Microcon-50 spin-column purification (Amicon, USA) as described.

EXAMPLE 14
TEA.3HF-catalysed Silyl to Hydroxyl Replacement

The reaction leads to the direct replacement of a 2'-O-silyl group with a hydroxyl group when carried out in the presence of TEA.3HF. Between 100 ng to 1000 ng of silyated (TBDMS) mRNA in 10 μl of dimethyl formamide was mixed with 50 μl of pure triethylamine-tris-hydrofluoride (TEA.3HF). The reaction is allowed to proceed for 14 hours at room temperature (Sproat, et al., (1995) *Nucleosides and Nucleotides* 14:255). The unreacted components were removed either by ethanol precipitation (Sambrook et al., (1989) *Molecular Cloning: A Laboratory Manual,* CSH) or Microcon-50 spin-column purification (Amicon, USA) as described.

EXAMPLE 15
Fluoride Ion-catalysed Silyl to Acyl Replacement

The reaction leads to the direct replacement of a 2'-O-silyl group with an 2'-O-acyl group when carried out in the presence of fluoride ion. Between 100 ng to 1000 ng of silyated mRNA in 10 μl of dimethyl formamide was mixed with a solution containing 30 nmol tetra-(n-butyl) ammonium fluoride (TBAF), 10 μmol of acetic anhydride and tetrahydrofuran (THF) serving as the solvent to bring the final volume to 50 μl. The reaction is allowed to proceed for 30 minutes to 5 hours at room temperature. Alternatively, acetic-formic, pivalic, propanoic, butyric, pentanoic, hexanoic anhydrides or benzoic anhydride may be substituted for the acetic anhydride as the acetyl donor or acetylating agent (Beaucage and Ogilvie, (1977) *Tetrahedron Letters,* 1691). The unreacted components were removed either by ethanol precipitation (Sambrook et al., (1989) *Molecular Cloning: A Laboratory Manual,* CSH) or Microcon-50 spin-column purification (Amicon, USA) as described.

EXAMPLE 16
Phase Transfer Catalysis-2'-O-Alkylation Approaches

To the two phase system consisting of 1 μg (1.6 pmol) of mRNA was added 6 ng of tetrabutylammonium iodide in 5 μl of dichloromethane and 2.5 μl of 7.8 nmol NaOH was vigorously mixed for 30 minutes and then 4 nmoles of either dimethyl or diethyl sulphate was added whilst the reaction temperature was maintained at 45° C. The reaction was allowed to proceed for 3 hours at 45° C. and then 1 μl of NH$_3$ added, stirred and incubated for 30 minutes at room temperature (Merz, (1973) *Angew. Chem. Intl. Edit.* 12:846). The unreacted components were removed from the methyl ether modified RNA by either ethanol precipitation (Sambrook et al., (1989) *Molecular Cloning: A Laboratory Manual,* CSH) or Microcon-50 spin-column purification (Amicon, USA) as described. Alternatively, 6 ng of another phase transfer catalyst such as tetrabutylammonium bromide, tetrabutylammonium hydrogensulphate or tetraethylammonium tetrafluoroborate could be used.

EXAMPLE 17
Dialkyl Sulphate Reactions

To 1 μg (1.6 pmol) of mRNA was added 20 μl of dimethylformamide, and 4 nmoles of either dimethyl or diethyl sulphate was added whilst the reaction temperature was maintained at room-temperature. The reaction was allowed to proceed for 3 hours at room-temperature (Tazawa, et al., (1972) *Biochemistry* 11:4931). The unreacted components were removed from the methyl ether modified RNA by either ethanol precipitation (Sambrook et al., (1989) *Molecular Cloning: A Laboratory Manual,* CSH) or Microcon-50 spin-column purification (Amicon, USA) as described.

EXAMPLE 18
Diazomethane and SnCl$_2$ for 2'-methyl ether Formation

To 1 μg (1.7 pmol) of mRNA in 10 μl of dimethyl formamide was added 7 nmol of a diazomethane, 1 ng of SnCl$_2$ in a total volume of 50 μl of 1,2-dimethoxyethane. All reaction components were mixed on ice and the reaction was allowed to proceed for 24 hr at room temperature (Robins, (1974) *J. Org. Chem.* 39:1891–1899; Ekborg, (1980) *J. Carbohydrates Nucleosides Nucleotides* 7:57–61; Robins, (1981) *Can. J. Chem.* 59:3360–3364). The unreacted components were removed either by ethanol precipitation (Sambrook et al., (1989) *Molecular Cloning: A Laboratory Manual,* CSH) or Microcon-50 spin-column purification (Amicon, USA) as described.

EXAMPLE 19
Use of Methyl Iodide for 2'-methyl ether Formation

To 1 μg (1.7 pmol) of mRNA in 10 μl of dimethyl formamide was added 7 nmol of a alkyl iodide such as methyl iodide, 1 ng of Ag$_2$O in a total volume of 50 μl of dimethylformamide. All reaction components (Purdies method) were mixed on ice and the reaction was allowed to proceed for 24 hr at room temperature in the dark (Furukawa, Y. et al. (1965) Chem. Pharm. Bull. 13:1273; Frukawa, (1965) *Chem. Pharm. Bull.* 13:1273–1278; Inoue, (1987) *Nucleic. Acid. Res.* 15:6131–6148). The unreacted components were removed either by ethanol precipitation (Sambrook et al., (1989) *Molecular Cloning: A Laboratory Manual,* CSH) or Microcon-50 spin-column purification (Amicon, USA) as described.

EXAMPLE 20
Northern Blotting

A sample of the modified mRNA was prepared as in example 6, μg was loaded on a 0.8% agarose gel, followed by electrophoresis and transfer to a membrane (Hybond, Amersham, UK) as described (Sambrook et al., (1989) Molecular Cloning: A Laboratory Manual, CSH). The membrane was then used in a hybridisation with a radioactively labelled probe using standard methods. Alternatively, following transfer and immobilisation of the modified mRNA to the membrane the acetyl or any other ammonia sensitive group at the 2' position was cleaved with 28% ammonium hydroxide as follows. The membrane was covered with 50 ml of concentrated ammonia and incubated at room temperature for 5 minutes. In this case, the acetyl group at the 2'-position (i.e. 2'-O-COR) is replaced by the original 2'-OH group and therefore has normal hybridisation properties. The advantage of this approach is that denaturing agents are not required in either the gel loading buffer or the gel because the modified RNA has reduced secondary structure. Furthermore, the modified RNA can be stored, handled, separated on the gel and blotted to a membrane in a ribonuclease protected form. The binding properties of the modified RNA to the membrane are improved, probably because of its increased hydrophobicity.

EXAMPLE 21
Acetylation Using Imidazole Reagents

To 0.1–1 μg of RNA in 1 μl of water was added 20 μl of triethylamine containing a catalytic quantity (60 μg; 490 nmoles) of 4-dimethylaminopyridine (DMAP) and then 1 μl (10 μmol) of N-acetylimidazole (Review: Newer Methods of Prep. Org. Chem. 5:61) was added. The solution was mixed vigorously using a vortex for 5 seconds and the reaction allowed to proceed for 60 seconds at room temperature (22° C.). The reaction was then terminated by addition of three reaction volumes of ethanol or methanol followed by mixing with a vortex for 5 seconds. Modified RNA was removed from the reactants and solvent using one of several methods. The preferred method was purification using a Centricon-50 spin-column (Amicon, USA). Alternative imidazole reagents such as N-benzoylimidazole can be used with the same protocol.

EXAMPLE 22
Fluorescent Labelling of RNA

Derivatives of isatoic and N-methylisatoic anhydrides are fluorescent (Hiratsuka (1982) J. Biol. Chem. 257:13354). Fluorescent RNA derivatives are useful as probes for hybridisation studies such as Southern blotting and other applications. To 0.1–1 μg of RNA in 1 μl of water was added 20 μl of a non-basic solvent such as dimethyl formamide, THF or dimethyl sulphoxide containing a catalytic quantity (60 μg; 490 nmoles) of 4-dimethylaminopyridine (DMAP) and then 10 μl (100 μmoles) of either isatoic anhydride or N-methylisatoic anhydride was added. The solution was mixed vigorously using a vortex for 5 seconds and the reaction allowed to proceed for 60 minutes at room temperature (22° C.). The reaction was then terminated by addition of three reaction volumes of ethanol or methanol followed by mixing with a vortex for 5 seconds. Fluorescent RNA was removed from the reactants and solvent using one of several methods. The preferred method was purification using a Centricon-50 spin-column (Amicon, USA). The excitation wavelengths were 330 nm for isatoic anhydride derivatives and 350 nm for N-methylisatoic anhydride derivatives with emission spectra in the range of 410–445 nm depending on the solvent polarity.

EXAMPLE 23
Acetylation Using Tributylphosphine Catalyst

To 0.1–1 μg of RNA in 1 μl of water was added 20 μl of triethylamine containing a catalytic quantity (60 μg; 490 nmoles) of tributylphosphine (Vedejs and Diver (1993) J. Am. Chem. Soc. 115:3358) and then 1 μl (10 μmoles) of acetic anhydride was added. The solution was mixed vigorously using a vortex for 5 seconds and the reaction allowed to proceed for 60 seconds at room temperature (22° C.). The reaction was then terminated by addition of three reaction volumes of ethanol or methanol followed by mixing with a vortex for 5 seconds. Modified RNA was removed from the reactants and solvent using one of several methods. The preferred method was purification using a Centricon-50 spin-column (Amicon, USA).

EXAMPLE 24
Uncatalysed Acetylation

To 0.1–1 μg of RNA in 1 μl of water was added 20 μl of triethylamine containing 1 μl (10 μmoles) of acetic anhydride. The solution was mixed vigorously using a vortex for 5 seconds and the reaction allowed to proceed for 60 seconds at room temperature (22° C.). The reaction was then terminated by addition of three reaction volumes of ethanol or methanol followed by mixing with a vortex for 5 seconds. Modified RNA was removed from the reactants and solvent using one of several methods. The preferred method was purification using a Centricon-50 spin-column (Amicon, USA).

EXAMPLE 25
Overnight Reaction Using Reduced Acetic Anhydride Amounts

To 0.1–1 μg of RNA in 1 μl of water was added 20 μl of triethylamine containing a catalytic quantity (60 μg; 490 nmoles) of 4-dimethylaminopyridine (DMAP) and then 0.1 μl (1 μmol) or 0.01 μl (0.1 μmol) of acetic anhydride was added. The solution was mixed vigorously using a vortex for 5 seconds and the reaction allowed to proceed for over-night at room temperature (22° C.). The reaction was then terminated by addition of three reaction volumes of ethanol or methanol followed by mixing with a vortex for 5 seconds.

EXAMPLE 26
Mixtures of Acetylating Reagents

To 0.1–1 μg of RNA in 1 μl of water was added 20 μl of triethylamine containing a catalytic quantity (60 μg; 490 nmoles) of 4-dimethylaminopyridine (DMAP) and then 1 μg of a mixture of 9 parts acetic anhydride (8.82 μmole) and 1 part acetyl chloride (1.4 μmole) was added. The solution was mixed vigorously using a vortex for 5 seconds and the reaction allowed to proceed for over-night at room temperature (22° C.). The reaction was then terminated by addition of three reaction volumes of ethanol or methanol followed by mixing with a vortex for 5 seconds.

EXAMPLE 27
Mixtures of Modifying Reagents

In certain circumstances where it is desirable to obtain RNA modified with two or more modifying groups, mixtures of modifying reagents can be used in the same reaction. The relative proportion and reactivity of each reagent will determine the final number of each modifying group attached to each RNA chain. To 0.1–1 µg of RNA in 1 µl of water was added 20 µl of triethylamine containing a catalytic quantity (60 µg; 490 nmoles) of 4-dimethylaminopyridine (DMAP) and then 1 µl (5 µmole) of a mixture of 1 part acetic anhydride and 1 part (5 µmole) propionic anhydride was added. The solution was mixed vigorously using a vortex for 5 seconds and the reaction allowed to proceed over-night at room temperature (22° C.). The reaction was then terminated by addition of three reaction volumes of ethanol or methanol followed by mixing with a vortex for 5 seconds. In principle any combination of reactants could be mixed, providing there is no chemical reaction between them, to give a wide range of multiply modified RNA. Other useful combinations of reagents would be a mixture of acetic anhydride and isatoic anhydride. In this case it would be expected that the resulting modified RNA would have increased resistance to ribonuclease and be fluorescent.

EXAMPLE 28
Diluting Acetyl Chloride

It was found that adding 1 µl of acetyl chloride undiluted directly into the reaction led to excessive production of a white precipitate which made handling of the liquid difficult. For this reason acetyl chloride was first diluted in a suitable solvent such as toluene before mixing with the RNA. To 0.1–1 µg of RNA in 1 µg of water was added 20 µl of triethylamine containing a catalytic quantity (60 µg; 490 nmoles) of 4-dimethylaminopyridine (DMAP) and then 1 µl of either 10% (1.4 µmole) or 25% (3.5 µmole) acetyl chloride diluted in toluene was added. The solution was mixed vigorously using a vortex for 5 seconds and the reaction allowed to proceed for over-night at room temperature (22° C.). The reaction was then terminated by addition of three reaction volumes of ethanol or methanol followed by mixing with a vortex for 5 seconds.

EXAMPLE 29
Protection with Crown 18–6

It has been reported that addition of crown 18–6 eliminates the reaction of acetic anhydride with primary amines (Barrett et al., (1978) J. Chem. Soc. Chem. Commun. 471). In order to test the effect of crown 18–6 addition on RNA acetylation, it was added in varying amounts to a standard acetylation reaction. To 0.1–1 µg of RNA in 1 µl of water was added 20 µl of triethylamine containing a catalytic quantity (60 µg; 490 nmoles) of 4-dimethylaminopyridine (DMAP), and either 6.6 µg, 660 ng, 66 ng, 6.6 ng, 660 pg or 66 pg of crown 18–6 added and allowed to complex for 5 min. at room temperature and then 1 µl (10 µmoles) of acetic anhydride was added. The solution was mixed vigorously using a vortex for 5 seconds and the reaction allowed to proceed for 20 seconds at room temperature (22° C.). The reaction was then terminated by addition of three reaction volumes of ethanol or methanol followed by mixing with a vortex for 5 seconds.

EXAMPLE 30
Increased RNA Substrate Quantity

To determine the upper limit for the amount of RNA that can be added to a standard acetylation reaction, varying amounts of RNA were added. The highest RNA concentration used (24 µg) represented the highest concentration of RNA that it was possible to dissolve in 1 µl of water without the RNA precipitating out of solution. To either 0.5, 1, 2, 6, 12 or 24 µg of RNA in 1 µl of water was added 20 µl of triethylamine containing a catalytic quantity (60 µg; 490 nmoles) of 4-dimethylaminopyridine (DMAP) and then 1 µl (10 µmoles) of acetic anhydride was added. The solution was mixed vigorously using a vortex for 5 seconds and the reaction allowed to proceed for 20 seconds at room temperature (22° C.). The reaction was then terminated by addition of three reaction volumes of ethanol or methanol followed by mixing with a vortex for 5 seconds. It was found that even with 24 µg of RNA, the acetylation reaction proceeded to the same degree as the reactions containing less RNA. Therefore 20 µg or more of RNA may be modified per reaction under these conditions.

EXAMPLE 31
Deprotection with Alkali

The reversible nature of the acetylation reaction was examined using alkali which is known to lead to the cleavage of the acetyl group and replacement with a —OH group. To 0.1–1 µg of acetylated RNA in 5 µl of water was added 1 µl of either 1 M, 500 mM or 250 mM of freshly dissolved NaOH and deprotection allowed to proceed for 15 min. at room temperature before neutralisation with an equal volume and concentration of HCl. It was found that subsequent to acetyl group cleavage, the 2'-OH group was attacked by the alkali leading to RNA phosphate backbone cleavage.

EXAMPLE 32
Deprotection with Ammonium Hydroxide

Ammonium hydroxide is also an effective reagent for acetyl group cleavage. To 0.1–1 µg of acetylated RNA in 5 µl of water was added 1 µl or 5 µl of ammonium hydroxide solution (26%) and deprotection allowed to proceed for 15 min. at room temperature. The RNA can be purified using a Centricon-50 column. Other acyl groups such as those produced by reaction of butyric or propionic anhydrides will also be cleaved by this ammonia hydroxide treatment.

EXAMPLE 33
Modified RNA Stability

The instability of RNA is a consequence of the reactivity of the ribose 2'-OH groups which leads to strand breakage. Many conditions and chemicals lead to the RNA strand breakage such as high pH and divalent metal ions. The consequence of modifying the 2'-OH group is to increase the stability and intactness of the RNA allowing complete cDNA copies and accurate measurements of its size and abundance to be made.

It is preferable to choose 2'-OH modifications that provide maximum stability to the modified RNA, yet can be readily removed under mild conditions without leading to RNA chain cleavage. Although acetyl can be removed using ammonia or KCN for example, there can be some subsequent cleavage of the RNA chain, therefore, when it is important to subsequently remove the modification, it is preferred to choose a 2'-OH modification that is removed under milder conditions than acetyl. In the acyl series, both methoxyacetate (20), formyl (100) and chloroacetyl (760), bromoacetyl ($7.6 \times 10^3$), dichloroacetyl ($1.6 \times 10^4$), trichloroacetyl ($10^5$), and carbonates are more easily cleaved than acetyl (relative rates of cleavage compared to acetyl are given in brackets see; Greene and Wuts (1991) Protective Groups in Organic Synthesis, $2^{nd}$ Ed. Wiley Interscience). The choice of the specific 2'-OH modification will depend on the level of protection required during the procedure being carried out and the ease with which the modification can be removed. For example chloroacetate is too labile for protecting RNA during gel electrophoresis because it is cleaved by the electrophoresis buffer.

Experimental Approach

A key biophysical characteristic of RNA is its intactness and completeness. Natural RNA chains can be tens of thousands of bases long and must be preserved in this condition if they are to be usefully studied. In order to measure the robustness of modified RNA under conditions known to lead to RNA chain cleavage a sequencing gel assay was used. Simply, a radioactive nucleotide was incorporated into RNA during an in vitro transcription reaction, then the RNA modified and subjected to conditions that normally results in its degradation. The result was analysed following electrophoresis on a sequencing gel to assess its completeness. Intact (modified) RNA gave a single band whilst degraded RNA appeared as a smear of smaller fragments. In each case, RNA modified with various reagents were compared side by side with natural RNA. An added advantage of this gel assay was the unambiguous identification of modified RNA sample lanes because of its reduced electrophoretic mobility (see figure below).

FIG. 1 demonstrates the enhanced resistance of modified RNA. A sequencing gel was run with alternating lanes of normal RNA (lanes 1,3,5,7) and acetylated RNA (lanes 2,4,6,8). Two RNA sizes of 250 and 1525 bases can be seen per lane. Samples were heated in a PCR buffer (2.5 mM $MgCl_2$) for 0 min (lane 1,2), 2 min. (lane 3,4), 6 min. (lane 5,6), and 13 min. (lane 7,8), at 94° C. Despite less modified RNA than normal RNA being loaded (compare lanes 1 and 2), acetylated RNA was still detectable after 13 minutes at 94° C. whilst normal RNA was undetectable after only 6 minutes. Note the smear in lane 3 as a result of RNA degradation.

Enzymatic Degradation of RNA Samples

A selection of commonly used nucleases were incubated with labelled RNA samples and the degradative effect visualised by sequencing gel degradation. The enzymes and conditions used were; S1 nuclease (Part. No. E576A, Promega, USA), degrades single-stranded DNA and RNA. 100 ng of each type of RNA was mixed with 10 µl of 1×S1 nuclease buffer containing 15, 1.5 or 0.15 units S1 and incubated for 15 min at 37° C. Mung bean nuclease (part. No. M194A, Promega, USA) an endonuclease, degrades single stranded DNA and RNA. 100 ng of each type of RNA was mixed with 10 µl of 1×mung bean nuclease buffer containing 50, 5 or 0.5 units nuclease and incubated for 15 min at 37° C. 10–100 pg RNase A (Cat. No. 109 142, Boehringer Mannheim) a general purpose RNase was incubated with 100 ng each RNA in 1×buffer (40 mM Tris-HCl (pH 7.5), 6 mM $MgCl_2$, 2 mM spermidine and 10 mM NaCl) and incubated for 15 min at 37° C. 1/1000 unit RNase One™ (Part. No. M4261, Promega, USA) was mixed with 100 ng of each RNA in 1×RNase One buffer and incubated for 15 min at 37° C.

Chemical Degradation of RNA Samples

Conditions known to favour RNA degradation include high pH and metal ions. In each case 100 ng of each labelled RNA sample (modified and normal) was mixed under the following conditions. An equal volume of formamide and RNA sample was mixed and incubated for 1 min to 30 min at 99° C. A 9 mM $MnCl_2$ solution was mixed with each RNA to bring the final $Mn^{2+}$ concentration to 1.5 mM. The mixture was then heated for 5 min at 100° C. A 25 mM $MgCl_2$ solution was mixed with each RNA to bring the final $Mg^{2+}$ concentration to 1.5 mM. The mixture was then heated for 5 min at 100° C. 100 ng of each RNA was incubated with 100 mM, 250 mM, 500 mM and 1 M NaOH solution and incubated for 5 min at room temperature. 100 ng of RNA was mixed with 10 µl of PCR buffer (15 mM Tris-HCl pH 8.8, 60 mM KCl, 2.5 mM $MgCl_2$) and heated for 5 min at 94° C. followed by 15 min at room temperature. Serum assays were carried out by removing the red blood cell component from 200 µl human blood and incubating 100 ng RNA with 10 µl serum for 15 min at 37° C.

Conclusion

The modification of the ribose 2'-OH group provides excellent resistance to conditions that would otherwise lead to the rapid degradation of RNA. Carbon chain lengths that were attached to the 2'-OH group of the test RNA were from 2 carbon (acetyl) to 8 carbon (octanoate) and trimethyl acetyl and the benzoyl group. The 8 carbon chain length was not preferred because the extent of RNA modification was below 100%. Carbon chain lengths of 3–5 were preferred because they efficiently modified the RNA and offered good protection from both enzymatic and chemical attack. Protection from degradation in 1×PCR buffer is significant because DNA or RNA polymerisation nearly always involves heating samples in Mg or Mn containing buffers; conditions that rapidly lead to RNA template degradation and as a result poor sensitivity

EXAMPLE 34

PCR and Reverse Transcription

Experimental

Template Preparation

Synthetic RNA (in vitro) transcripts and purified viral RNA (BMV) were used as templates. RNA templates derived from an in vitro transcription reaction using T7 RNA polymerase and pGEM express positive control template (Part No. P256A, Promega, USA) were prepared according to the manufacturer's instructions. Two RNA transcripts were generated of 1065 and 2346 bases in length. Template DNA was removed by the addition of 1 unit of RNase free DNase RQ1 and incubating for 15 min at 37° C., followed by extraction with phenol:chloroform, then chloroform:isoamyl alcohol (24:1) and a final purification using Centricon-50 column filtration (Amicon, USA). Final volumes were typically 10 µl and RNA concentrations adjusted to 1 µg/µl. This procedure provided very pure RNA preparations suitable for chemical modification and subsequent use as DNA polymerase templates.

The use of DNA primers specific for the RNA modification that had been prepared resulted in newly synthesised DNA strands of pre-determined sizes thereby aiding analysis. The 1065 and 2346 base RNA transcripts prepared as described above contain annealing sites for the primers SP6 and T3. SP6 and T3 could be used together for PCR or SP6 alone for reverse transcription studies.

Reverse Transcription 100 ng (modified or normal) RNA was heated for 10 min at 75° C. in 10 µl of water containing 50 ng SP6 primer or oligo (dT) and then left on ice. Alternatively, no pre-annealing step was required for BMV RNA reverse transcription. Modification of the RNA could be made with a range of modifying reagents such as acetic-formic, acetic or benzoic anhydrides. The reverse transcription reaction contained either 2 µl of 25 mM $MgCl_2$ or 13 mM $MnCl_2$, 2 µl 100 mM DTT, 1 µl 10 mM dNTPs, 1 µl 32P dCTP and 1 µl (10 units), Superscript II (Gibco-BRL, USA) (10 units), HIV reverse transcriptase (Seikagaku, Japan), 10 units of MULV Point mutant (Promega, USA), or (10 units) AMV reverse transcriptase (Invitrogen, Netherlands). The reaction was incubated at a temperature from 37° C. to 55° C. for 30 minutes and stopped by the addition of 1 µl of 0.5 M EDTA. TCA precipitation was carried out by spotting 5 µl of the reaction onto glass filters and washing three times with 100 ml 10% TCA and counting. For gel analysis of the 32P labelled cDNA, the reaction was mixed with one volume 95% formamide load dye containing bromophenol blue and loaded. into a 7M urea, 4% acrylamide gel containing 1×TBE and run at 80 W for 1 hour. The gel was then fixed for 5 minutes in 10% acetic acid and dried. Bands were quantitated using a Molecular Dynamics Phosphorimager.

Reverse Transcription Results

Both Superscript II and HIV reverse transcriptases can copy modified RNA into a complementary DNA strand. However a large reduction in the amount of product (50–100 fold less than normal RNA) was observed with Superscript II reactions when acetylated RNA was reverse transcribed using oligo (dT). This reduction was probably due to the thermal instability of the oligo (dT): modified poly (A) RNA hybrid because modified RNA appears to have a reduced melting temperature. Effective priming was obtained using primers such as SP6 that contain G and C bases which increase stability. Excellent results were obtained with formylated and methoxyethoxymethyl chloride modified BMV RNA.

Advantages of Modified RNA Templates

In separate experiments, modified RNA has been shown to have greatly increased resistance to conditions that rapidly degrade RNA. Conditions necessary for the effective use of Tth and Taq enzymes (high temperature and cation concentration) are also optimal for the degradation of the template RNA. It would therefore be advantageous to be able to use conditions that were optimal for enzyme activity but did not lead to the degradation of the template. By modifying the 2'-OH groups, the modified RNA retains both its template activity and completeness with conditions where a substantial proportion of the normal RNA is degraded.

Decreased melting temperature of the modified template RNA should also reduce the amount of secondary structure. RNA secondary structure leads to DNA polymerase obstruction and as a result chain termination and incomplete DNA copies. The secondary structure of mRNA is the major impediment to the production of full length cDNA clones and libraries. Unfortunately state of the art methods that have been developed to reduce the amount of secondary structure also result in RNA degradation. Because modified RNA has less secondary structure, enzyme obstruction should be reduced and therefore the proportion of full length cDNA clones increased. In addition, the template modified RNA is not becoming degraded and therefore the quality of the template is also improved.

RT-PCR Amplification of Modified RNA Templates

The following two enzyme method was used to amplify modified RNA templates. To 0.1–1 µg of RNA template containing SP6 and T3 sites, in 1 µl of water was added 20 µl of triethylamine containing a catalytic quantity (60 µg; 490 nmoles) of 4-dimethylaminopyridine (DMAP) and then 1 µl (10 µmoles) of acetic anhydride or acetic formic anhydride was added. The solution was mixed vigorously using a vortex for 5 seconds and the reaction allowed to proceed for 60 seconds at room temperature (22° C.). The reaction was then terminated by addition of three reaction volumes of ethanol or methanol followed by mixing with a vortex for 5 seconds. Modified RNA was removed from the reactants and solvent using one of several methods. The preferred method was to dilute the mixture into a final volume of 400 µl of water which was then added to a Centricon-50 spin-column (Amicon, USA) and centrifuged for 15 minutes at 3000 g or until the filter was dry. The filter was then washed by addition of 400 µl of water and again spun for 15 minutes at 3000 g. The modified RNA was recovered by inverting the cup containing the filter in a fresh centrifuge tube and spinning it for 60 seconds at 3000 g.

Portions of the modified RNA (100 µg to 10 ng) were used as templates for reverse transcription with Superscript II enzyme. 100 ng (modified or normal) RNA was heated for 10 min at 75° C. in 10 µl of water containing 50 ng SP6 primer and then left on ice. To this was added 2 µl of 25 mM $MgCl_2$, or 13 mM $MnCl_2$, 2 µl 100 mM DTT, 1 µl 10 mM dNTPs, 1 µl 32P dCTP and 1 µl (10 units), Superscript II (Gibco-BRL, USA) (10 units). The reaction was incubated within the temperature range 37° C. to 55° C. for 30 minutes. Template was removed by incubating samples with RNase A (1 µg) for 15 min at 37° C. 8 µl aliquots of the reverse transcription reaction were added to the following PCR mixture. The PCR was carried out in a final volume of 100 µl with final concentration of 15 mM Tris-HCl pH 8.8, 60 mM KCl, 2.5 mM $MgCl_2$, 400 µM each dNTP, 10 pmol of each primer SP6 and T3 and 1 unit Taq DNA polymerase (Amersham, UK). Cycle parameters were 94° C.×20 sec, 55° C.×20 sec and 72° C.×30 sec for 30 cycles. PCR products were visualised following agarose gel electrophoresis and staining with EtBr.

Reverse Transcription with Tth DNA Polymerase

Reverse transcription with Tth DNA polymerase offers the advantage of elevated reaction temperature that can reduce the amount of RNA secondary structure. The following two enzyme method was used to amplify modified RNA templates. To 0.1–1 µg of RNA template containing SP6 and T3 sites, in 1 µl of water was added 20 µl of triethylamine containing a catalytic quantity (60 µg; 490 nmoles) of 4-dimethylaminopyridine (DMAP) and then 1 µl (10 µmoles) of acetic anhydride was added. The solution was mixed vigorously using a vortex for 5 seconds and the reaction allowed to proceed for 60 seconds at room temperature (22° C.). The reaction was then terminated by addition of three reaction volumes of ethanol or methanol followed by mixing with a vortex for 5 seconds. Modified RNA was removed from the reactants and solvent using one of several methods. The preferred method was to dilute the mixture into a final volume of 400 µl of water which was then added to a Centricon-50 spin-column (Amicon, USA) and centrifuged for 15 minutes at 3000 g or until the filter was dry. The filter was then washed by addition of 400 µl of water and again spun for 15 minutes at 3000 g. The modified RNA was recovered by inverting the cup containing the filter in a fresh centrifuge tube and spinning it for 60 seconds at 3000 g.

The following protocol is essentially identical to the one provided by Boehringer Mannheim GmBH. To 2 µl of 1×buffer (10 mM Tris-HCl pH 8.9, 90 mM KCl) was added 2 µl of 9 mM $MnCl_2$, 0.4 µl of 200 µM each dNTP, 750 nM SP6 primer, 50–200 ng modified template RNA and 1 µl (4 units) of Tth DNA polymerase and water to a final volume of 20 µl. The reaction was incubated for 30 min at 70° C. DNA products could then be used in a standard PCR reaction or visualised by adding trace quantities (1 µl) of radioactive $^{32}P$ dATP to the reaction and separating the products by gel electrophoresis.

EXAMPLE 35

Hybridisation

Experimental Approach

Modified RNA was either immobilised onto a solid support such as a filter membrane (target) or labelled with radioactivity (probe) and allowed to hybridise with the target. Comparisons were made between modified and normal RNA as target and probes.

Dot Blotting

RNA samples were labelled as follows. 100 ng of either modified (acetylated) or normal RNA was added to 13 μl of water, 2 μl 10×kinase buffer and 1 μl of shrimp alkaline phosphatase (Boehringer Mannheim) added. The reaction was incubated for 10 min at 37° C. and then the enzyme destroyed by treating for 10 min at 65° C. The 5' end of the RNA was then labelled by the addition of 2.5 μl $^{32}$P γ-ATP and 1 μl of T4 polynucleotide kinase (Boehringer Mannheim) and incubating 90 min at 37° C. Unincorporated label was removed using a Centricon-50 column according to manufacturers instructions.

cDNA target was prepared using 1000 ng of 7.5 kb poly (A) tailed RNA (Cat. No. 15621-014, Gibco-BRL, USA) using a Superscript II cDNA kit (Life Technologies, USA) using oligo (dT) as a reverse transcriptase primer according to manufacturer's instructions. The reaction was terminated by incubating at 70° C. for 10 minutes. RNA was removed by treatment with RNase H (200 ng RNase H added to the reaction and incubated 15 min at 37° C.) and 50 ng of the remaining cDNA spotted onto a 5 mm square of Hybond N+ and allowed to dry before u/v cross-linking for 3 min. and baking at 65° C. for 10 min. Two such squares were hybridised with either a modified or normal 7.5 kb RNA $^{32}$P labelled probe at 65° C. over-night in Church buffer (0.5M NaPi pH7.2, 7% SDS and 1 mM EDTA). The squares were then washed at room-temperature in 1×Church buffer and results quantitated by scintillation counting.

Figure 2:
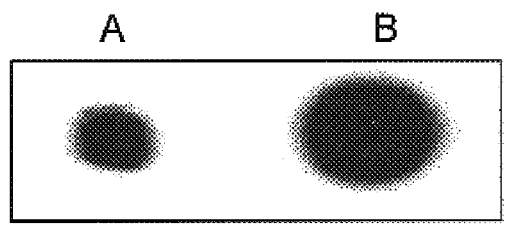
FIG. 2 shows a comparison of hybridisation properties of modified and unmodified RNA.

FIG. 2 shows a comparison of the hybridisation properties of modified RNA and RNA in which Panel A is modified 7.5 kb RNA probe and panel B is normal 7.5 kb RNA probe. Each probe was hybridised to an immobilised cDNA target.

Comparison of Different Hybridisation Membranes

In order to select an optimum hybridisation membrane to be used, a portion of radiolabelled modified (acetylated) RNA was spotted onto 5 mm squares of six different membranes (Protran NC, Hybond N+ (Amersham, UK), Immobilon for DNA sequencing, Porablot NCL, Porablot PVDF, Immobilon P) and dried at room-temperature. each square was then washed twice for 5 min at 65° C. in Church buffer and the amount of radioactivity remaining on the squares quantitated using a scintillation counter.

TABLE 1

Binding properties of different hybridisation membranes

| Membrane | % CPM Remaining after washing |
|---|---|
| Protran-NC | 24.4% |
| Hybond N+ | 31.6% |
| Immobilon | 10.3% |
| Porablot NCL | 20.7% |
| Porablot PVDF | 19.8% |
| Immobilon P | 6.4% |

From these results it was apparent that Hybond N+ was the best membrane for binding acetylated RNA. However, Hybond N+ was less suitable than nitrocellulose for hybridisation. Hybridisation signals were approximately two times stronger when the modified RNA was attached to nitrocellulose than Hybond N+. However, nylon membranes are substantially more resistant to ammonium hydroxide treatment than nitrocellulose.

A further comparison was made between modified (acetylated) RNA spotted onto membranes in a denatured or native (folded) state. Denaturation was brought about by heating at 68° C. for 5 min in a 50% formamide/2.2 M formaldehyde solution prior to spotting on Hybond N+ membranes and hybridising with a labelled cDNA probe. No significant differences were detected in the hybridisation signals between denatured and native folded modified RNA.

Northern Blotting Procedure

Northern blotting was carried out according to Goda and Minton (1995) Nucleic Acid. Res. 16:3357–3358. Briefly, gels were prepared by adding 0.5 ml of 1 M guanidine thiocyanate and 2 μl of EtBr (10 mg/ml) in 100 ml of molten 1.2% agarose containing 1×TBE buffer. Modified (acetylated) or normal RNA (0.24–9.5 kb RNA ladder (Cat. No. 15620-016, Life Technologies, USA); CAT mRNA, luciferase (Promega, USA) or human liver mRNA (Clontech, USA) was denatured by mixing a 10 μl sample (25 ng–1 μg) with 10 μl formaldehyde and 5 μl formamide, heating at 90° C. for 5 min. and then adding 10×loading dye (50% glycerol, 1 mM EDTA, pH 8.0, 0.4% Bromophenol blue. Following electrophoresis at 100 V for 2 hrs the gel was photographed see panel A) and then the RNA was transferred to Hybond N+ (Amersham, UK) membrane according to manufacturers instructions. The membrane was hybridised overnight at 65° C. in 'Church buffer' with a radioactive probe.

Deprotection with Ammonia

Figure 3:
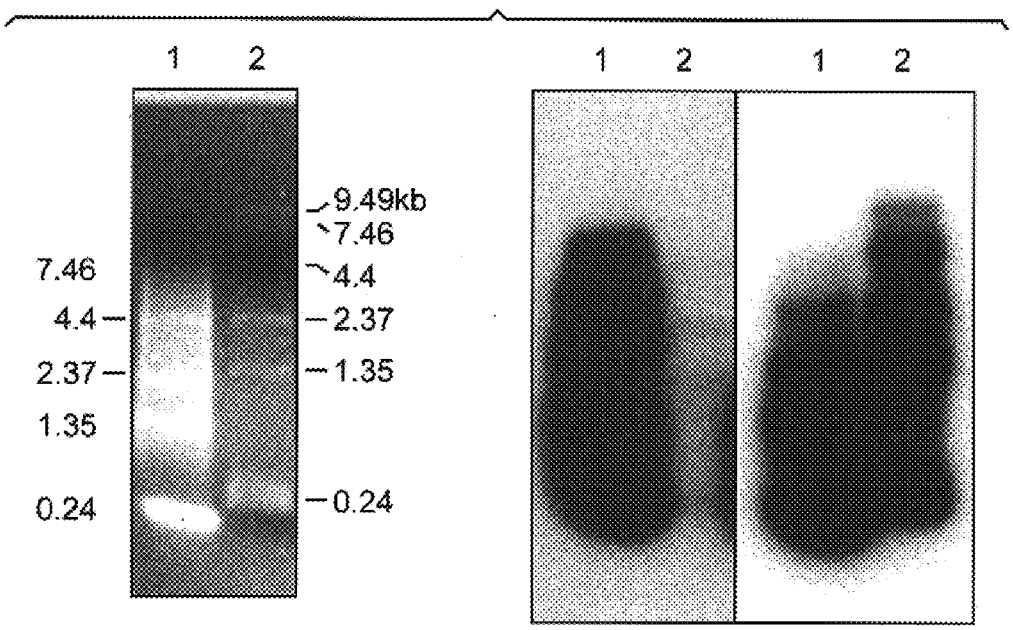
FIG. 3 shows results of agarose gel and northern blotting comparing modified and unmodified RNA.

Under the conditions used, the modified RNA hybridised only very weakly to the probe. Results are shown in FIG. 3. By contrast the normal RNA gave a strong signal (panel B). By removing (deprotecting) the acetyl groups from the modified RNA using ammonia treatment, hybridisation was restored (panel C). The failure to hybridise may have been due to the reduction in Tm of the modified RNA or interaction between the charged carbonyl group (C=O) which is part of every acetyl group (—CO—CH3). The negative charge on the oxygen may be sufficient to allow interaction with the positive charges covering the Hybond N+membrane, and as a result cause the modified RNA to adopt a conformation not compatible with hybridisation. 50 ml of ammonium hydroxide (26%) was added to the northern membrane and incubated for 5 min. at room temperature. The membrane was rinsed with water and then immersed in Church buffer for 10 min. Hybridisation was carried out as described. It will be apparent that other 2'-substituents than acetyl may require longer or shorter incubation periods with ammonium hydroxide, for example phenoxy acetyl is 50 times more labile than acetyl. There are also other methods to remove the modifying group such as KCN cleavage.

FIG. 3 shows a comparison of modified and unmodified RNA behaviour on agarose gel and northern blotting. Panel A shows an EtBr stained agarose gel (lane 1) 0.24–9.5 kb RNA ladder (Cat. No. 15620-016, Life Technologies, USA), (lane 2) 0.24–9.5 kb RNA ladder modified by acetylation prior to electrophoresis. Note the differences in mobility and the increased degradation of normal RNA. Panel B shows that acetylated RNA does not hybridise appreciably to a radioactive cDNA probe when bound to a nylon membrane under standard conditions. Panel C shows that, following removal of the acetyl groups from the modified RNA by ammonia treatment, hybridisation is strong.

Change in Electrophoretic Mobility of Modified RNA

Figure 4:
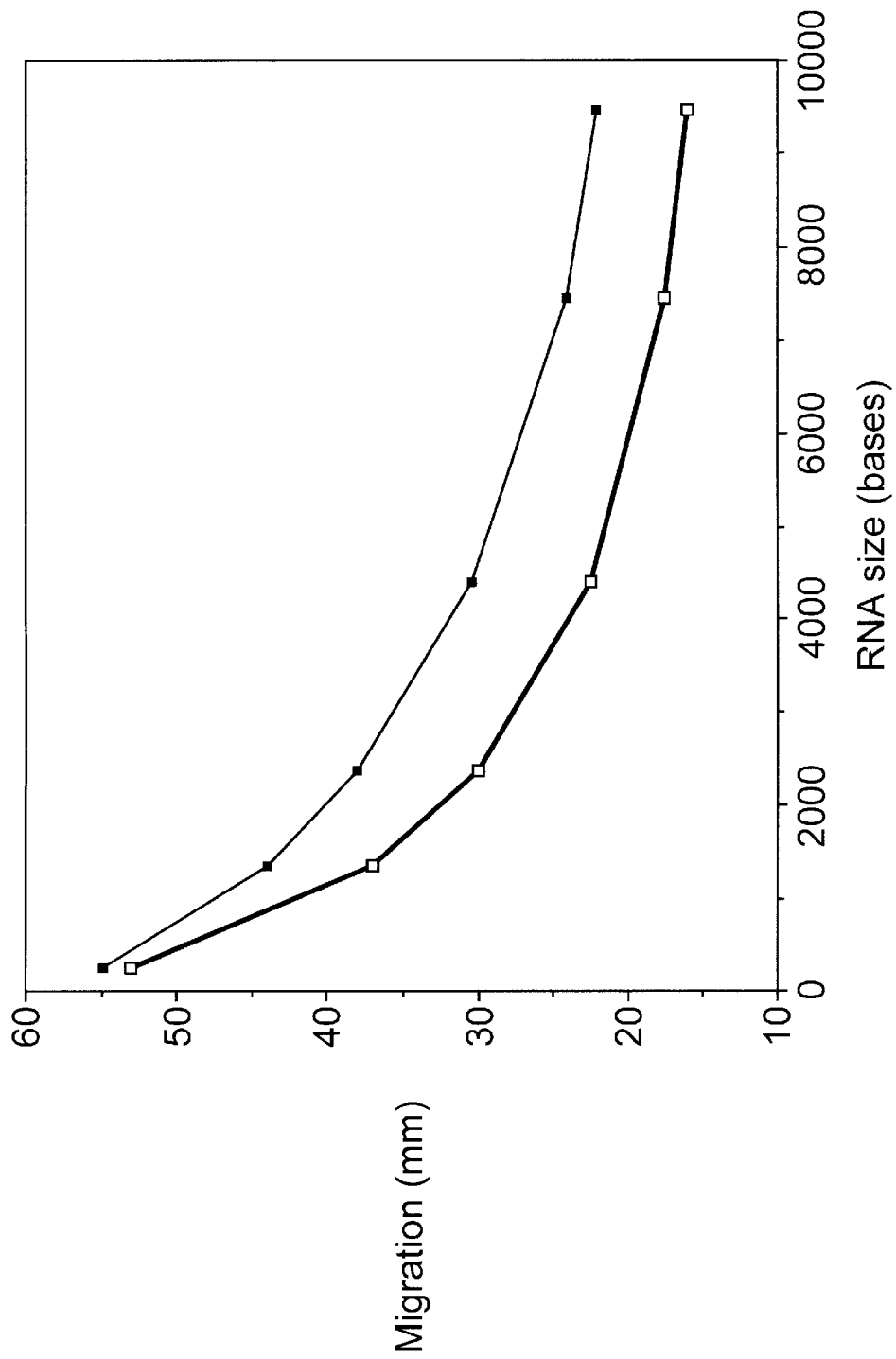
FIG. 4 compares gel electrophoretic migration behaviour of modified and unmodified RNA.

FIG. 4 demonstrates the relationship between electrophoretic mobility (mm) and molecular weight (bases) of modified (acetylated) and normal RNA in an agarose gel (see Panel A of FIG. 3). The upper line represents unmodified RNA and the lower line represents modified RNA. Modified RNA migrates at approximately 75% the rate of normal RNA reflecting its increased molecular weight due to the acetyl group and possibly a change in secondary structure. It was found that the individual markers in an RNA marker (0.24–9.4 kb RNA ladder, Life Technologies, USA) modified with acetic, propionic, butyric or valeric anhydrides all had very similar mobilities to one another despite the differences in the molecular weight of the modifying group. However, RNA modified using benzoic anhydride, had a mobility similar to unmodified RNA. This may reflect alterations in the structure of the modified RNA and how easily it can pass through the sieving action of the agarose gel. Reduced mobility of modified RNA in the agarose gel may be caused by conformational changes of the polynucleotide In order to accurately measure changes in the molecular weight of the RNA due to the modification, it is necessary to use denaturing sequencing gels such as 6M urea-6% acrylamide with radiolabelled RNA in the range of 250–500 nucleotides.

Conclusion

RNA modified by acetylation has altered hybridisation properties, probably reflecting a lower Tm of the hybrid. Standard conditions of hybridisation for northern blotting are probably too stringent and a lower temperature should be chosen. Removal of the modifying groups reconstitutes the hybridisation properties of the RNA.

Significant advantages of the use of modified RNA for northern blotting are as follows. 1) Modified RNA binds to the hybridisation membrane with greater efficiency than normal RNA; 6 fold more modified RNA is retained on the membrane after washing in a strong detergent solution at 65° C. than normal RNA. 2) Modified RNA does not degrade during electrophoresis and as a result it represents faithfully the starting material. 3) Simpler northern blotting materials can be used because the modified RNA has a reduced melting temperature. Without secondary structure formation, the RNA can be electrophoresed under mild conditions without the use of toxic denaturants such as formaldehyde. Despite their toxicity, formaldehyde northern blots are currently the standard procedure. Formaldehyde is known to covalently modify the adenine base thereby suppressing hydrogen bonding and as a consequence RNA secondary structure. Formaldehyde modification would therefore also be expected to reduce the efficiency of hybridisation between probe and target. By contrast, acylated RNA provides a means to reduce secondary structure and following deprotection, allow highly efficient hybridisation properties. With formyl modified RNA it is not necessary to deprotect prior to hybridisation although some formyl loss may occur spontaneously in the hybridisation mixture. The modified RNA provides much clearer separation of bands and unlike normal RNA, no degradation.

EXAMPLE 36

Acylation in Aqueous-tetrahydrofuran Solution

To 0.1–1 µg of RNA in 1 µl of water was added 20 µl of tetrahydrofuran containing a catalytic quantity (60 µg; 490 nmoles) of DMAP and then 10 µmole of acetic anhydride or other acylating agent was added. The solution was mixed vigorously using a vortex for 5 seconds and the reaction allowed to proceed for 20–60 minutes at room temperature before it was terminated by the addition of three volumes of ethanol and mixing. The modified RNA could be purified away from the acetic-formic, propanoic, butyric, pentanoic, hexanoic, heptanoic, octanoic or benzoic anhydrides.

EXAMPLE 37

Acylation in Aqueous-dimethyl Formamide Solution Using 4-pyrrolidinopyridine

To 0.1–1 µg of RNA in 1 µl of water was added 20 µl of dimethyl formamide containing a catalytic quantity of 4-pyrrolidinopyridine and then 0.1–10 µmole of acetic anhydride or other acylating agent was added. The preferred reaction contained 1 µg of RNA, 20 µl of dimethyl formamide, 60 µg of 4-pyrrolidinopyridine and 0.1 µmole of acetic anhydride. The solution was mixed vigorously using a vortex for 5 seconds and the reaction allowed to proceed for 20–60 minutes at room temperature before it was terminated by the addition of three volumes of ethanol and mixing. The modified RNA could be purified away from the reactants using Centricon-50 spin-column or ethanol precipitation. Other acylation agents include benzoic, propanoic, butyric, pentanoic, hexanoic, heptanoic and caprylic anhydrides.

EXAMPLE 38

Acylation in Aqueous-dimethyl Formamide Solution Using DMAP

To 0.1–1 µg of RNA in 1 µl of water was added 20 µl of dimethyl formamide containing a catalytic quantity (60 µg; 490 nmoles) of DMAP or (3 mg) 1-methylimidazole) and then 0.1–10 µmole of acetic anhydride or other acylating agent was added. The preferred reaction contained 1 µg of RNA, 20 µl of dimethyl formamide, 60 µg of DMAP and 1 µmole of acetic anhydride. The solution was mixed vigorously using a vortex for 5 seconds and the reaction allowed to proceed for 20–60 minutes at room temperature before it was terminated by the addition of three volumes of ethanol and mixing. The modified RNA could be purified away from the reactants using Centricon-50 spin-column or ethanol precipitation. Other acylation agents include propanoic, butyric, pentanoic, hexanoic, heptanoic, octanoic or benzoic anhydrides.

EXAMPLE 39

Acylation Using 2-hydroxypyridine Catalyst

To 0.1–1 µg of RNA in 1 µl of water was added 20 µl of triethylamine containing a catalytic quantity (60 µg; 490 nmoles) of 2-hydroxypyridine and then 0.1–10 µmole of acetic anhydride or other acylating agent was added. The preferred reaction contained 1 µg of RNA, 20 µl of TEA, 60 µg of DMAP and 1 µmole of acetic anhydride. The solution was mixed vigorously using a vortex for 5 seconds and the reaction allowed to proceed for 5–20 minutes at room temperature before it was terminated by the addition of three volumes of ethanol and mixing. The modified RNA could by purified away from the reactants using Centricon-50 spin-column or ethanol precipitation. Other acylation agents include propanoic, butyric, pentanoic, hexanoic, heptanoic, octanoic or benzoic anhydrides.

EXAMPLE 40

Use of Tetraethylammonium Acetate for Acetylation

To 1 µg (1.7 pmol) of mRNA or viral RNA was added 1 µmol of tetraethylammonium acetate and the mixture rendered anhydrous and then resuspended in 1 µl (10 µmol) of acetic anhydride. Following an incubation period of 2 hrs at room temperature, 10 µl of 1:1 (v:v) pyridine;water was added and the reaction incubated 5 hrs at room temperature. The unreacted components were removed either by ethanol precipitation (Sambrook et al., (1989) Molecular Cloning: A Laboratory Manual, CSH) of Microcon-50 spin-column purification (Amicon, USA) as described.

EXAMPLE 41
Use of Pyridinium Chlorochromate for Oxidation

The oxidation of alcohols (—OH→=O) is a well known procedure and pyridinium chlorochromate (Corey's Reagent) is particularly useful as an oxidising agent. The use of acetic acid can improve the reaction rate (Agarwal et al, (1990) Tetrahedron 46:4417–4420). To 1 µg (1.7 pmol) of mRNA or viral RNA in 10 µl of dimethyl formamide was added 5 nmol of pyridinium chlorochromate, 40 µl (1.6 nmol) of acetic acid to serve as an acid catalyst and the mixture incubated for 2 hrs at room temperature. The unreacted components were removed either by ethanol precipitation (Sambrook et al., (1989) Molecular Cloning: A Laboratory Manual, CSH) or Microcon-50 spin-column purification (Amicon, USA) as described.

EXAMPLE 42
Stability of RNA Modified with Butyric and Pentanoic Anhydrides

RNA was modified with either butyric or pentanoic anhydrides in accordance with the method of example 6.

Figure 5:
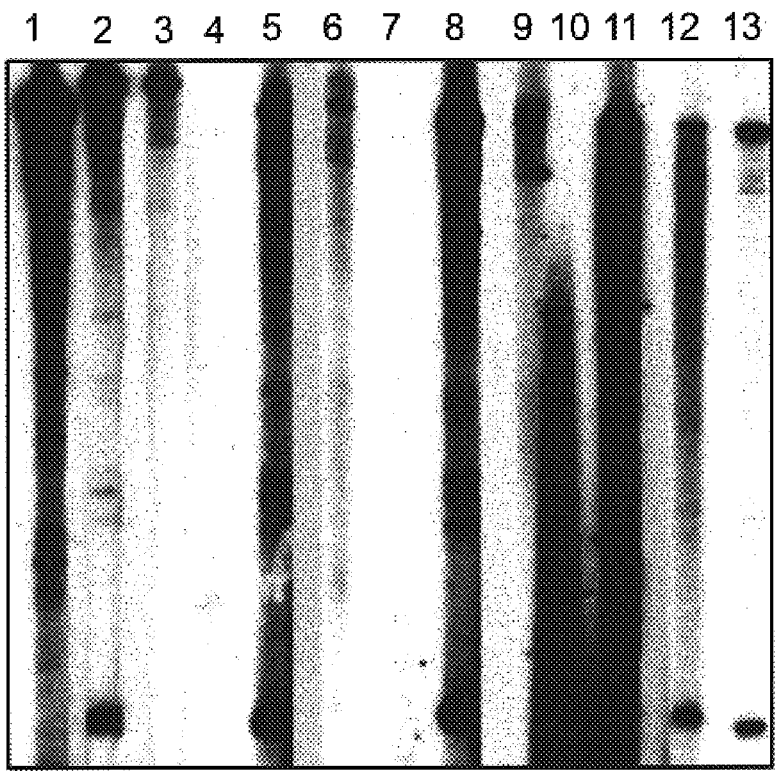
FIG. 5 shows gel electrophoretic behaviour of butyric and pentanoic anhydride modified RNA.

FIG. 5 shows enhanced stability of RNA modified with butyric and pentanoic anhydrides. The Lanes are as follows: Lane 1; Radiolabelled riboprobe (Promega, USA) RNA, lane 2; butyric anhydride modified RNA, lane 3; pentanoic anhydride modified RNA, lanes 4–6; samples treated with 5 units of mung bean nuclease for 10 minutes at 37° C., lane 4; RNA, lane 5; butyric anhydride modified RNA, lane 6; pentanoic anhydride modified RNA, lanes 7–9; samples treated with 15 units of S1 nuclease for 10 minutes at 37° C., lane 7; normal RNA, lane 8; butyric anhydride modified RNA, lane 9; pentanoic anhydride modified RNA, lanes 10–12; samples treated in 80 mM NaOH for 15 minutes at 22° C., lane 7; normal RNA, lane 9; butyric anhydride modified RNA, lane 9; pentanoic anhydride modified RNA, land 13; marker lane with acetic anhydride modified RNA. Note the complete degradation of RNA with mung bean nuclease (lane 4), S1 nuclease (lane 7) and its partial degradation with alkali (lane 10) compared with modified forms.

EXAMPLE 43
Acetyl Chloride Modification of RNA in Presence and Absence of Catalyst This example compares the degree of RNA acetylation as set out below in accordance with the method of example 8 in the presence and absence of the catalyst, DMAP.

Figure 6:
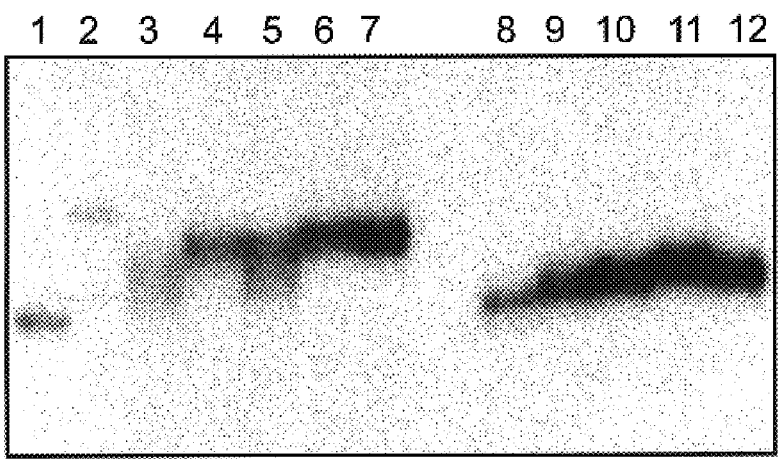
FIG. 6 shows gel electrophoretic behaviour of RNA acetylated in the presence and absence of a catalyst.

FIG. 6 shows a comparison of the degree of RNA acetylation using different concentrations of acetyl chloride with or without the catalyst DMAP. The lanes are as follows: Lane 1; radiolabelled riboprobe RNA marker (Promega, USA), lane 2, acetylated riboprobe RNA marker, Lanes 3–12; acetylation of RNA with acetyl chloride in a catalysed (3 mg/ml DMAP) (lanes 3–7) or uncatalysed (lanes 8–12) solvent system. Acetyl chloride of varying concentration and in a final volume of 1 µl of toluene was mixed with 100 ng RNA in 1 µl of water, 20 µl of TEA with or without a catalyst and incubated for 20 seconds at room temperature. Lane 3; 0.25%, lane 4; 0.5%, lane 5; 0.75%, lane 6; 1% and lane 7; 1.25% final concentration of acetyl chloride with DMAP. Lane 8; 0.25%, lane 9; 0.5%, lane 1-; 0.75%, lane 11; 1% and lane 12; 1.25% final concentration of acetyl chloride without DMAP. The amount of acetylation increases with increasing acetyl chloride concentration and in the presence of DMAP catalyst. Even when the highest concentrations of acetyl chloride are used with the catalyst (lane 7), there is less modification than with acetic anhydride (lane 2).

EXAMPLE 44
Acetylation of RNA with Prolonged Reaction Time

Using the methodology of example 37, this example shows the effect of reaction time on acetylation of RNA using acetic anhydride.

FIG. 7 shows increased acetylation of RNA when reaction times are prolonged. Modification reactions were carried with 20 ng of radiolabelled riboprobe RNA and 100 ng yeast RNA, 1 µl of acetic anhydride, 20 µl of TEA containing 3 mg/ml of DMAP, mixed and incubated for the following times. The lanes are as follows: Lane 1; 0 seconds, lane 2; 20 seconds, lane 3; 1 minute, lane 4; 6 minutes and lane 5; 20 minutes at room temperature before the reaction was stopped and analysed on a sequencing gel. Reactions were stopped by the addition of three volumes of ethanol with mixing.

EXAMPLE 45
Extent of RNA Modification Using DMAP Catalyst

This example compares the extent of RNA modification in the presence and absence of the catalyst DMAP. A DMAP catalysed acetylation reaction was carried out in accordance with example 6 and compared with an analogous reaction carried out in the absence of DMAP in accordance with example 36.

FIG. 8 shows that catalyst DMAP increases the amount of RNA modification by acetic anhydride. Lane 1; 20 ng of radiolabelled riboprobe RNA, 10 µg of yeast RNA, 10 µg of acetic anhydride and 20 µl of TEA containing 3 mg/ml of DMAP, lane 2; 20 ng of radiolabelled riboprobe RNA, 10 µl of yeast RNA, 1 µl of acetic anhydride, 20 µl of TEA with no DMAP, lane 3; unmodified RNA size marker. Reactions were carried out for 20 seconds at room temperature. Note the distinct step between lanes 1 and 2 demonstrating that the RNA in lane 2 is more modified in the presence of DMAP than without (lane 1).

EXAMPLE 46
Formylation of RNA Using Benzoic Formic Anhydride

Benzoic formic anhydride was produced by mixing either 6 molar equivalents (1 ml) of formic acid with 1 (1 g) or 2 molar equivalents (2 g) of benzoic anhydride and mixing for 15 minutes at 22° C. 1 µl of the product was used without further purification in a 20 µl reaction containing 19 µl THF, 3.2 mg (39 µmol) 1-methylimidazole and 60 µg DMAP and 100 ng RNA and the reaction incubated at 22° C. for 1 hr. This reagent is unstable under some conditions, leading to the build up of carbon monoxide and benzoic acid within the storage vessel when stored at 4° C. However, the simplicity of preparing benzoic formic anhydride allows the reagent to be made each time it is needed.

EXAMPLE 47
Formylation of RNA and RT-PCR
Formylation Reaction

5 µl of acetic formic anhydride was added to a 100 µl reaction containing 95 µl THF, 16 mg (195 µmol) 1-methylimidazole, 300 µg DMAP and 100 ng BMV RNA and the reaction incubated at 22° C. for 10 min before purification by ethanol precipitation, Centricon-50 spin filtration (Amicon, USA), dialysis or binding to silica beads (Qiagen, Germany). The formylated RNA was diluted in water to give a final concentration of 25 ng/µl.

Reverse Transcription 25 ng of formylated BMV RNA was added to a 10 µl reaction mixture containing the following final component concentrations: 200 mM Tris-HCl (pH 8.4 at 24° C.), 75 mM KCl, 1.3 mM MnCl$_2$, 10 mM DTT, 1 mM dNTP's, 110 ng of oligonucleotide primer and 100 units of Superscript II™ (Life Technologies, USA) or MULV RNase H⁻ (Promega, USA). Water was used to bring the final volume to 10 µl. The reaction was allowed to proceed for 1 hr in the temperature range 28–34° C. The cDNA can then be purified by for example, ethanol precipitation, Centricon-50 filtration or used directly in a PCR reaction as follows.

PCR Amplification

The PCR was carried out in a final volume of 25 µl with final concentration of 15 mM Tris-HCl pH 8.8, 60 mM KCl, 2.5 mM MgCl2, 400 µM each dNTP, 10 pmol of each primer BMV F and BMV R and 1 unit Taq DNA polymerase (Amersham, UK). Generally 2.5 ng (1 µl) of template cDNA generated from the formylated BMV RNA was added per reaction. Cycle parameters were 94° C.×20 sec, 55° C.×20 sec and 72° C.×30 sec for 30 cycles. PCR products were visualised following gel electrophoresis and staining with EtBr.

EXAMPLE 48

Hybridisation with Formylated RNA

Northern Blotting Procedure

Northern blotting was carried out according to Goda and Minton (1995) Nucleic Acid. Res. 16:3357–3358. Briefly, gels were prepared by adding 0.5 ml of 1 M guanidine thiocyanate and 2 µl of EtBr (10 mg/ml) in 100 ml of molten 1.2% agarose containing 1×TBE buffer. Modified RNA (formylated) or RNA (0.24–9.5 kb) ladder (Cat. No. 15620-016, Gibco-BRL, USA); was loaded in an equal volume (3 µl) of glycerol/0.01% bromophenol blue. Following electrophoresis at 100 V for 2 hrs the gel was photographed (see panel A) and then the RNA was transferred to a Hybond N+ (Amersham, UK) membrane according to manufacturers instructions. The membrane was hybridised overnight at 65° C. in 5 ml 'Church buffer' with $10^6$ cpm/ml of a radioactive cDNA probe representing the RNA ladder. The membrane was washed twice in Church buffer at room temperature and an image acquired and analysed using a Phosphorimager and ImageQuant (Molecular Dynamics, USA). The hybridisation signal of all the bands in the formylated RNA lane was 4% greater than for the RNA lane, probably because the formylated RNA was more intact and/or transferred to the membrane more efficiently than RNA. Another advantage was the excellent resolution of the RNA ladder bands, which tended to separate into distinct bands whilst the RNA bands formed an almost continual smear between the 0.24 and 9.4 kb band. This may be because the formylated RNA has lost secondary structure and is therefore separated in the gel on the basis of its molecular weight. Whilst the 7.5 and 9.4 kb RNA bands transferred and/or hybridised poorly, the formylated 7.5 and 9.4 kb bands hybridised strongly so that distinct bands were visible. The ability to detect long RNA is critical for the success of northern blotting as many cellular transcripts are over 5 kb in length and some such as the mammalian Xist transcript substantially more than 10 kb.

Dot Blotting Procedure

In order to establish the optimum temperature for formylated RNA to hybridise in Church buffer, equal quantities of formylated 0.24–9.4 kb RNA ladder or unmodified RNA ladder were dotted onto Hybond N+ and processed as for northern blots. The immobilised samples were hybridised over-night at 55, 60 and 65° C. with $10^6$ cpm/ml radioactive cDNA probe in 200 µl Church buffer, and then washed twice in 1 ml of Church buffer at 22° C. The hybridisation was quantitated using a Phosphorimager. The following table 2 represents the results of the hybridisation represented in arbitrary units.

TABLE 2

| Temp./° C. | RNA | formyl RNA |
|---|---|---|
| 55 | 7.79 | 8.18 |
| 60 | 8.81 | 6.69 |
| 65 | 1.56 | 0.95 |

From these results it can be seen that the optimum temperature for hybridisation of formyl RNA in Church buffer is 55° C. and for RNA 60° C. At 55° C. formyl RNA hybridises 1.05 times better than RNA

EXAMPLE 49

Modification of RNA Using 2-methoxyethoxymethyl (MEM) Chloride

To 120 µl of an EDPA and THF mixture (1:7 v/v) was added 3 µl of MEM chloride and 10–100 ng of RNA in 1 µl of water. The reaction was briefly vortexed and incubated at 22° C. for 5–30 minutes. The reaction was stopped and the modified RNA recovered from the reaction components by the addition of three volumes of ethanol containing 300 mM sodium acetate followed by centrifugation at 10,000 g for 5 minutes. The pellet was washed with 100 µl of 70% ethanol and resuspended in water prior to analysis or use as a RT-PCR template. Under these conditions it was found by gel electrophoresis in a urea-4% acrylamide sequencing gel with appropriate molecular size markers that the RNA appeared to be modified to 100%.

EXAMPLE 50

Reverse Transcription of MEM Modified RNA 20 ng of MEM modified BMV RNA was added to a 10 µl reaction mixture containing the following final component concentrations: 200 mM Tris-HCl (pH 8.4 at 24° C.), 75 mM KCl, 1.3 mM MnCl₂, 10 mM DTT, 1 mM dNTP's, 110 ng of oligonucleotide primer and 100 units of MULV Point Mutant (Promega, USA). Water was used to bring the final volume to 10 µl. Note that the 1.3 mM MnCl₂ can be substituted in the reaction by 2.5 mM MgCl₂. The reaction was allowed to proceed for 1 hr at 42° C. The cDNA can then be used directly in a PCR reaction as follows.

The PCR was carried out in a final volume of 50 µl with final concentration of 15 mM Tris-HCl pH 8.8, 60 mM KCl, 2.5 mM MgCl₂, 400 µM each dNTP, 10 pmol of each primer BMV F and BMV R and 1 unit Taq DNA polymerase (Amersham Pharmacia Biotech, UK). 4 µl of template cDNA was added per reaction. Cycle parameters were 94° C.×8 sec, 55° C.×8 sec and 72° C.×10 sec for 30 cycles. PCR products were visualised following agarose gel electrophoresis and staining with EtBr.

EXAMPLE 51

Hybridisation of MEM Modified RNA

A comparison of the ability of MEM modified RNA versus RNA to hybridise was tested using a simple dot blot hybridisation. The immobilised target was 100 ng of alkali denatured pGEMEX plasmid (Promega, USA) that had been cross-linked on Hybond N+ (Amersham Pharmacia Biotech, UK) using standard dot-blot protocols (Sambrook et al., CSH). To 100 µl of Church hybridisation buffer (0.5M NaPi pH7.2, 7% SDS and 1 mM EDTA) containing the membrane was added approximately 5000 cpm of ³²P UTP labelled riboprobe prepared by in-vitro transcription from pGEMEX using RNA polymerase T3 (Promega, US). The hybridisation was allowed to proceed for 2 hrs at 55° C., and then the membrane was washed under increasingly stringent wash conditions. These were; 10 min at 22° C. in 500 µl of Church buffer, 10 min at 65° C. in 500 μl of 100 mM NaCl/10 mM Tris-HCl (pH7.5) and 10 minutes at 65° C. in 0.1% SDS. The amount of radioactivity remaining hybridised to the target was quantitated using an InstantImager (Hewlett Packard, US). The results demonstrated that 20% more MEM modified RNA hybridises to the target than a RNA probe and both probes are washed off the target under similar conditions.

EXAMPLE 52
Modification of RNA with Triisopropylchlorosilane Chloride (TIPSCl)

10 ng of $^{32}$P UTP radiolabelled RNA in 1 μl of THF was added to a 45 μl silylation reaction containing 5 μl of EDPA and 35 μl of THF, 200 μg of either imidazole or DMAP catalyst and 3 μl of triisopropylchlorosilane chloride (TIPSCl) (tert-butyldimethylchlorosilane imidazole (TBDMS imidazole), trimethylsilyl imidazole (TMS imidazole) or other suitable silylation reagents may also be used) and allowed to react for 30 min–3 hrs at 22° C. Purification was carried out by ethanol precipitation and analysis in a urea-acrylamide sequencing gel electrophoresis using suitable molecular weight markers to measure the degree of modification. It was found that the addition of imidazole to a reaction containing EDPA/THF and TIPSCl led to a significantly reduced extent of degradation of a 1500 nucleotide RNA.

EXAMPLE 53
Stability Studies of Acylated RNA

In order to test the relative stability of acetylated RNA and RNA under conditions commonly encountered during storage or transport, the breakdown of a radiolabelled 1500 nucleotide acetylated RNA compared with RNA was quantitated in water at 37° C. To 100 ng of $^{32}$P UTP radiolabelled acetylated RNA (acetylated and purified using standard conditions) or RNA (Rioprobe, Promega, USA) was added 10 μl of water and incubated at 37° C. for either 1 day or 4 days. The samples were then loaded onto a urea-4% acrylamide sequencing gel. Following electrophoresis, drying and exposing of a phosphor screen, the 1500 nucleotide band intensity was quantitated using a PhosphorImager and ImageQuant software (Molecular Dynamics, USA). Whilst over 80% of the RNA was degraded after 4 days at 37° C., no acetylated RNA degradation could be detected.

EXAMPLE 54
Acyl Cyanide RNA Modification

The use of acyl cyanides for acylation have been reviewed (Angew. Chem. Int. Ed. (1982) 21:36; Tetrahedron Lett. (1971) 185; J. Chem. Soc., Perkin 1 (1976) 1351). To 0.1–1 μg of mRNA in 1 μl of water was added 20 μl of triethylamine and then 10 μmoles of either acetyl cyanide or benzoyl cyanide was added. The solution was mixed vigorously using a vortex for 5 seconds and the reaction allowed to proceed for 30 minutes at room temperature (22° C.). The reaction was then terminated by addition of three reaction volumes of ethanol or methanol followed by mixing with a vortex for 5 seconds. Modified RNA was removed from the reactants and solvent using one of several methods. The preferred method was to dilute the mixture into a final volume of 400 μl of water which was then added to a Centricon-50 spin-column (Amicon, USA) and centrifuged for 15 minutes at 3000 g or until the filter was dry. The filter was then washed by addition of 400 μl of water and again spun for 15 minutes at 3000 g. The modified RNA was recovered by inverting the cup containing the filter in a fresh centrifuge tube and spinning it for 60 seconds at 3000 g. Recovery volumes were typically 5–15 μl and recovery yields >95%.

EXAMPLE 55
Acetyl Bromide RNA Modification

The use of acetyl bromide for acetylation has been reviewed (Synthesis (1975) 249; J. Med. Chem. (1973) 16:630; ibid (1974) 17:427). To 0.1–1 μg of mRNA in 1 μl of water was added 20 μl of triethylamine and then 10 μmoles of acetyl bromide was added. The solution was mixed vigorously using a vortex for 5 seconds and the reaction allowed to proceed for 30 minutes at room temperature (22° C.).

Preferably, the reaction is carried out in the presence of trifluoroacetic acid to direct acylation to the 2'-OH groups. To 0.1–1 μg of mRNA in 1 μl of water was added 20 μl of tetrahydrofuran containing 1–10 mM trifluoroacetic acid and then 10 μmoles of acetyl bromide was added. The solution was mixed vigorously using a vortex for 5 seconds and the reaction allowed to proceed for 30 minutes at room temperature (22° C.). The reaction was then terminated by addition of three reaction volumes of ethanol or methanol followed by mixing with a vortex for 5 seconds. Modified RNA was removed from the reactants and solvent using one of several methods. The preferred method was to dilute the mixture into a final volume of 400 μl of water which was then added to a Centricon-50 spin-column (Amicon, USA) and centrifuged for 15 minutes at 3000 g or until the filter was dry. The filter was then washed by addition of 400 μl of water and again spun for 15 minutes at 3000 g. The modified RNA was recovered by inverting the cup containing the filter in a fresh centrifuge tube and spinning it for 60 seconds at 3000 g. Recovery volumes were typically 5–15 μl and recovery yields >95%.

EXAMPLE 56
Dialysis to Remove Reaction Components

A standard 20 μl modification reaction containing 19 μl triethylamine, 100 μg of DMAP, 2 μl of acetic anhydride and 500 ng of 0.24–9.4 kb RNA ladder (Life Technologies) was incubated for 10 min at 22° C. and transferred to a Mini-Slide-A-Lyzer (MWCO 3,500) and the unit capped. The dialysis unit was then transferred into 800 ml of water which was slowly stirred. After 90 min, one quarter (5 μl) of the dialysed reaction was loaded in a 1% agarose, 0.5×TBE gel and following electrophoresis the modified RNA visualised by ethidium bromide staining. It was apparent that the acetylated RNA was largely free of the contaminants because it readily entered the gel: unpurified RNA fails to enter the gel due to the contaminants present. Dialysis therefore offers a simple and suitable means for post-reaction clean-up.

EXAMPLE 57
Bromination of RNA with Phosphorous Tribromide

To 30 μl of a 1:1 mixture of triethylamine and dimethyl formamide (DMF) was added 0.1 μl (1 μmol) of PBr$_3$ and 1 μl of RNA (100 ng) dissolved in DMF. The reaction was allowed to proceed for 10 min at 22° C. with mixing. The halogenated RNA can then be purified by any number of means such as ethanol precipitation. It is important to dilute the PBr$_3$ in a non-reactive solvent such as DMF, otherwise a dense precipitate is formed. Other solvents for the reaction that can be used are pyridine, ether and less preferably DMF. Increasing the amount of PBr$_3$ leads to the formation of a precipitate which is difficult to separate from the RNA. However, washing the pellet twice with 500 μl of 70% ethanol dissolves the precipitate allowing the RNA sample to be retrieved.

EXAMPLE 58
Chlorination of RNA with Phosphorous Trichloride

To 30 µl of pyridine was added 0.1 or 1 µl (11.5 µmol) of $PCl_3$ and 1 µl of RNA (100 ng) dissolved in DMF. The reaction was allowed to proceed for 10 min at 22° C. with mixing. The halogenated RNA can then be purified by any number of means such as ethanol precipitation. It is important to dilute the $PCl_3$ in a non-reactive solvent such as DMF. Other solvents for the reaction that can be used are ether, DMF and less preferably triethylamine.

EXAMPLE 59
Chlorination of RNA with Thionyl Chloride

To 30 µl of ether was added 0.01, 0.1 or 1 µl (11.5 µmol) of thionyl chloride ($SOCl_2$) and 1 µl of RNA (100 ng) dissolved in DMF. The reaction was allowed to proceed for 10 min at 22° C. with mixing. The halogenated RNA can then be purified by any number of means such as ethanol precipitation. It is important to dilute the $PCl_3$ in a non-reactive solvent such as DMF. Other solvents for the reaction that can be used are pyridine or DMF. Other solvents that can be used are DMF and less preferably triethylamine.

EXAMPLE 60
Reverse Transcription of Halogenated RNA 30 ng of brominated BMV RNA was added to 100 ng of oligonucleotide primer (GAGCCCCAGCGCACTCGGTC) in 3 µl total volume and heated at 72° C. for 10 min before chilling on ice. Then 7 µl of a reaction mixture was added containing the following final component concentrations: 50 mM Tris-HCl (pH 8.4 at 24° C.), 75 mM KCl, 1.3 mM $MgCl_2$, 10 mM DTT, 1 mM dNTP's, and 100 units of Superscript II™ (Life Technologies, USA). The reaction was allowed to proceed for 1 hr at 37° C. 5 µl of the cDNA reaction was loaded on a 1% agarose gel and, following electrophoresis stained with ethidium bromide. A broad band of cDNA was observed representing the reverse transcription product. The cDNA was then used directly in a PCR reaction as follows.

PCR Amplification

The PCR was carried out in a final volume of 25 µl with final concentration of 15 mM Tris-HCl pH 8.8, 60 mM KCl, 2.5 mM $MgCl_{2, 400}$ µM each dNTP, 10 pmol of each primer BMV F (CTATCACCAAGATGTCTTCG) and BMV R (GAGCCCCAGCGCACTCGGTC) and 1 unit Taq DNA polymerase (Amersham, UK). 1 µl of template cDNA was added per reaction. Cycle parameters were 94° C.×10 sec, 55° C.×10 sec and 72° C.×15 sec for 30 cycles. PCR products were visualised following gel electrophoresis and staining with ethidium bromide. A large amount of PCR product resulted from this amplification, equal or greater to the amount generated by an identical procedure using BMV RNA as a template.

EXAMPLE 61
Nuclease Resistance of Halogenated RNA

RNA was brominated as follows. 500 µl of triethylamine/DMF (1:1) was added to 5 µl of phosphorus tribromide and 1 µg of (0.24–9.5 kb)RNA ladder (Cat. No. 15620-016, Life Technologies) dissolved in 10 µl of DMF added and mixed briefly. The reaction was stopped after 10 min at 22° C. by the addition of three volumes of ethanol, 0.3 M NaOAc and the brominated RNA precipitated. The sample was resuspended in 20 µl of water.

2 µl (100 ng) was of brominated RNA or RNA was added to a 10 µl reaction containing 1 µl of RNase ONE™ (Promega, USA) in 1×Promega reaction buffer and incubated for 6 min at 22° C. Alternatively, 50 ng of sample was added to a reaction containing 10 ng of RNase A and incubated for 9 min at 22° C. The extent of RNA degradation was analyses by agarose gel electrophoresis. Whereas all the RNA ladder was degraded so that no ethidium bromide staining material was apparent, approximately half of the brominated sample was visible although it had been partly degraded. These nuclease experiments demonstrate the enhanced resistance endowed by the replacement of the 2'-OH group by a bromine atom.

EXAMPLE 62
Reverse Transcription of RNA Templates Modified with Small Amounts of Acetic Anhydride Although acetic anhydride modified RNA is not generally a good template for reverse transcriptases, using reduced amounts of acetic anhydride provides a modified template with good template qualities. 1 µl of diluted acetic anhydride was used in a 20 µl reaction containing 19 µl THF, 3.2 mg (39 µmol) 1-methylimidazole and 60 µg DMAP and 10 ng BMV RNA and the reaction incubated at 22° C. for 10 min before purification by ethanol precipitation. The BMV RNA was used as a template for Superscript II reverse transcriptase and the cDNA used as a template for PCR using BMV specific primers. PCR products were detected with 0.0001 and 0.001 but not 0.01 or 0.1 µl of acetic anhydride.

EXAMPLE 63
Enzymatic Acylation

To 1 µg of RNA is added 2.5 nmol vinyl acetate and 1 µg of *Candida albicans* or porcine spleen lipase in 100 µl of pyridine or THF under nitrogen. The reaction is allowed to proceed at 30–60° C. over-night and the acetylated RNA purified by filtration or phenol extraction followed by ethanol precipitation. There are many potentially useful esterases that could be exploited to transfer an acyl group to RNA. Those from fungal or mammalian sources are preferred because many are commercially available. Specificity of each enzyme for the acylation reaction may have to be tested empirically.

EXAMPLE 64
Enzymatic Deacylation

To 1 µg of acylated RNA such as acetylated, butanoylated or propanoylated RNA in 100 µl of 100 mM phosphate buffer (pH 7) was added 1 unit of esterase or lipase such as porcine liver esterase, porcine spleen esterase, rabbit liver esterase, *Candida rugosa* lipase, *Chromobacterium viscosum* lipase, *Mucor javanicus* lipase, *Mucor meihei* lipase, *Rhizopus arrhizus* lipase, wheat germ lipase or from *Pseudomonas* species (Sigma). Alternatively, enzymes may be selected from other sources such as from the esterase/lipase Clonezyme library (Recombinant BioCatalysis™, USA). The reaction was incubated for 1 hr at 37° C.–70° C., depending on the source of the enzyme, until the pH no longer dropped indicating deacylation was complete. Alternatively, organic solvents such as tetrahydrofuran or dimethyl sulphoxide can be used in concentrations ranging from 5 to 100% when mixed into the aqueous solution. In certain reactions, it may be preferable to protect RNA using the benzoyl group because, the product of the cleavage reaction benzoic acid can be sublimed. Such removal of the product would be expected to drive the reaction to completion.

Comparative Example
(OVODOV)

An attempt was made to reproduce the work of OVODOV and ALAKHOV (1990) FEBS 270: 111 who report acetylation of 70–75% of the 2'-OH groups of a mRNA from a cell-free transcription system using the acetylation method of KNORRE et al (1967) Molekul.Biol 1: 837. The results of the Knorre method were compared with the results from the methods according to the present invention.

FIG. 9 shows a comparison of the efficacy of the two acetylation methods. Radiolabelled RNA ladders derived from an in vitro transcription reaction (Promega, USA) were treated with acetic anhydride either in an aqueous-DMF solvent system according to Knorre et al (Lanes 1–11) or in a 19:1 TEA:aqueous with a DMAP catalyst (lane 12) according to example 6 of the present application. For clarity, only one labelled RNA marker is shown. A decrease in mobility indicates modification occurring to the RNA indicating a successful modification reaction. The Lanes are as follows:Lane 1, Ribomark RNA treated for 2 hrs at 37° C. and then 46 hrs at room temperature, lane 2, Ribomark RNA treated for 48 hrs at room temperature, unmodified Ribomark RNA (lanes 3 and 130, Ribomark RNA treated for 1 hr at 4° C. with 0.01 µl (lane 4), 0.1 µl (lane 6) or 10 µl (lane 7) of acetic anhydride. Ribomark RNA treated for 1 hr at 37° C. with 0.01 µl (lane 8), 0.1 µl (lane 9), 1 µl (lane 11) of acetic anhydride. Lane 12, Ribomark RNA treated according to example 6.

It was found that the conditions according to Knorre were quite unable to modify the RNA even when reaction times were extended from the 1 hour specified to 48 hours (lanes 1 and 2) or acetic anhydride concentrations were increased 1000 times from the 98 nmol specified (lanes 4 and 8) to 98 µmol per 1 µg of RNA or reaction temperatures were increased from 4° C. (lanes 407) to 37° C. (lanes 8–11). In every case for the Knorre method, the RNA migrated at the same position as the unmodified controls (lanes 3 and 13). Only the TEA/DMAP/aqueous solvent system as described in present example 6 resulted in modification (lane 12). This and further attempts to repeat the work of Ovodov and Alakhov failed, leading to the conclusion that the publication by Ovodov and Alakhov does not enable modification of RNA in the manner they describe. This finding is consistent with the results presented by Ovodov and Alakhov in their publication where the molecular weight of the reported modified material is unchanged as compared with unmodified material.

Comparative Example
(Wang)

The methods employed by Wang et al., (in the references referred to below) to modify RNA oligonucleotides involve the use of either fluorodintrobenzene (FDNP) or dinitrophenol (DNP) in an aqueous buffered solution. It was predicted that the alkalinity (pH8.8) and extended reaction times (>18 hrs) would lead to polynucleotide cleavage with or without FDNP or DNP added. In order to ascertain whether these reaction conditions were capable of modifying longer RNA polymers, the following comparative reaction examples were carried out.

Lane 1, positive control RNA ladder (no treatment) containing 240, 1350, 2370, 4400, 7460 and 9490 nucleotide long RNA chains, lane 2 (DNP) and lane 3 (DFDNP) reaction according to Ru, Taub and Wang (1998) Oncology Res. 10:389, lane 4 (DFDNP) and lane 5 (DNP) reaction according to Wang WO 94/19012, lane 6, as reaction 1 and 2 without reactant (only buffer, RNA and acetone added and incubated 18 hrs) and lane 7, as reaction 3 and 4 without reactant added (only buffer, RNA and acetone added and incubated 18 hrs).

Results

The results are shown in FIG. 10. Following an 18 hr incubation in the Wang reaction system, all RNA samples (lanes 2–7) were significantly degraded leaving only traces of the double-stranded DNA template present as a contaminant in the RNA ladder. RNA incubated in the buffer alone are also degraded probably due to the alkalinity of the reaction. Only in lane 2 and 3 can a little of the 240 nucleotide RNA marker be seen. RNA alone in the buffer/acetone mixture led to total degradation of sample, whilst when the reactant is added, slightly less degradation occurs. The Wang reaction system is therefore not suitable for the modification of RNA polynucleotides. This may be in part due to the complex tertiary structure that RNA adopts in solution. It is necessary that the 2'-OH groups are modified and therefore protected before base catalysed cleavage can occur. With a complex tertiary structure as adopted by polynucleotides, it would be expected that the innermost 2'-OH groups are inaccessible to the solvent containing the reactant and cannot therefore be modified before RNA degradation occurs. This may explain why the 240 nucleotide RNA is less degraded than the 9490 nucleotide RNA which is completely degraded.

In conclusion, neither of the reaction conditions employed by Wang et al. are suitable for the modification of polynucleotides.

Regarding the Wang methods, naturally occurring RNA chains such as mRNA and viral RNA are on average 2000–10,000 nucleotides in length. Naturally occurring RNA, unlike DNA exists with a great deal of secondary structure, indeed the biological activity of RNA is often dependent on such structure. The biological activity of RNA is dependent on sequence specific secondary structure. RNA chains of a certain length and complementary sequence will spontaneously adopt a kinetically favoured conformation that resembles a globular protein. This will include regions of stem and loop, anti-parallel double strands and single stranded regions. Although the biological activity of RNA is frequently dependent on such secondary structure for example for control of protein translation or viral duplication, from the point of view of modifying the 2'-OH groups this introduces many uncertainties and potential problems as compared with either homopolymers or oligonucleotides.

The secondary and tertiary structure of RNA is referred to in many standard textbooks. In "RNA Isolation and Analysis" (1994, page 2, Bios Scientific Publishers, Oxford) it is stated that "antiparallel double helixes can be naturally formed between two separate RNA chains but more usually they occur between two segments of the same chain folded back on itself. These short double-helical regions are connected by single stranded stretches, adopting a globular shape" and in the section entitled Basic principles is stated "RNA is a linear molecule . . . with often high levels of secondary and tertiary structure" and ". . . RNA molecules are also prone to aggregation, . . . ", "However, the same problems of RNA aggregation . . . are also encountered. It is therefore necessary to use denaturing gels to determine the actual size in the absence of any conformational factors, aggregation and nicks in the RNA" and "a tertiary structure normally folds a buried catalytic core not in contact with surrounding solvent."

In "Molecular Biology of the Cell" ($3^{rd}$ edition (1994) page 7, Garland Publishing, Inc, N.Y.) it is stated "Such associations produce complex three dimensional patterns of folding, and the molecule as a whole takes on a specific shape that depends entirely on the sequence of its nucleotides" and "An RNA molecule therefore has two special characteristics: it carries information encoded in its nucleotide sequence . . . and it has a specific folded structure that enables it to interact selectively with other molecules and determines how it will respond to the ambient conditions."

In "Nucleic Acids in Chemistry and Biology" ($2^{nd}$ edition, (1996) Oxford University Press) it is stated "Different natural RNAs can either form long, double stranded structures or adopt a globular shape composed of short duplex domains connected by single-stranded segments". Unlike single stranded oligonucleotides which have interactions only with the solvent, longer RNA chains have to take into account the contributions of interactions between bases, sugars, phosphates, ions and solvent within and between RNA chains.

In "Biorganic Chemistry: Nucleic Acids" (1996, Oxford University Press) it is stated "RNA molecules can be likened to those of globular proteins and do not easily fit into categories like the DNA conformations, the tertiary structure . . . is distinctly globular in appearance.", "whilst this extensive stacking renders the tRNA interior inaccessible to solvent" and "Overall, RNA structures are quite distinct and differ substantially from the predominately linear, repeating polymers formed by DNA".

1. The tertiary structure of RNA can be investigated with chemical reagents such as Fe(II)EDTA that cleave all solvent exposed regions of RNA. Following such cleavage, it is clear that not all the RNA chain is cleaved because most of the RNA is buried and therefore hidden from the solvent bearing the cleavage reagent. This clearly demonstrates that a great deal of RNA is not normally available to solvent.
2. Whilst the thermodynamic properties of oligonucleotides (up to a maximum of 30 nucleotides) can be measured by a simple equation (Tm=(2×A/T)+(4×C/G) the Tm of longer chains (>30 nucleotides) cannot be measured by this equation because the biophysical rules of long chains are substantially different. Empirical measurements demonstrate that the Tm of the octamer poly(rA).poly(rU) is 9° C. whilst longer poly(rA).poly(rU) oligomers is 49° C.
3. Oligonucleotides or homopolymers are incapable of carrying meaningful genetic information or encoding protein sequence, whilst this is the primary function of mRNA and viral RNA.

From the above, it is therefore clear that longer RNA chains do not behave in the same chemical manner (1), physical manner (2) or biological manner (3) as oligonucleotides or homopolymers.

Wang Solvent and Salt System

Wang uses 210 mM potassium buffer with 40% acetone solvent present. It would be expected that such high concentrations of metal ion (the optimum sodium concentration for aggregation and precipitation of RNA is 300 mM) in the presence of acetone (which is used as a solvent to precipitate proteins out of solution) would lead not only to the stabilisation of tertiary structure of individual RNA chains but also aggregation of entire RNA chains together leading to the formation of a precipitate.

It has been found empirically that the stability of double stranded nucleic acids is increased markedly in the presence of potassium ions; the Tm increased from 70° C. at 10 mM potassium to 98° C. in 1M potassium. This confirms that the effect of the Wang buffer system would be to stabilise secondary and tertiary structure of the RNA and therefore the availability of the 2'-OH groups would be expected to be diminished because they are buried from the solvent bearing the Wang reactant. Oligonucleotides as Wang used would be expected to aggregate far less because aggregation is driven by sequence length. Unlike mRNA, rRNA and viral RNA, it is very difficult to precipitate oligonucleotides efficiently from solution.

What is claimed is:

1. A method for producing a composition comprising a modified poly-ribonucleotide, wherein said modified poly-ribonucleotide is an mRNA, rRNA, or viral RNA, said method comprising the steps of: (i) contacting a poly-ribonucleotide in a reaction medium comprising at least 80% v/v organic solvent with a reactant capable of covalently modifying the 2'-OH position of the ribose rings of said poly-ribonucleotide; and (ii) reacting said poly-ribonucleotide to produce a modified poly-ribonucleotide comprising greater than 25% of ribose rings bearing a C1–C10 alkanoyl at their 2'-OH position.

2. The method of claim 1, wherein said method comprises the step of separating the modified poly-ribonucleotide from said reaction medium.

3. The method of claim 1, wherein said reaction medium further comprises a catalyst.

4. The method of claim 1, wherein said covalent modification is achieved in one hour or less.

5. The method of claim 1, wherein said poly-ribonucleotide is a full length mRNA.

6. The method of claim 1, wherein said poly-ribonucleotide is a full length rRNA.

7. The method of claim 1, wherein said poly-ribonucleotide is a full length viral RNA.

8. The method of claim 1, wherein said poly-ribonucleotide is at least 1000 bases in length.

9. The method of claim 1, wherein at least 50% of said ribose rings are covalently modified at said 2'-OH position with a C1–C10 alkanoyl.

10. The method of claim 1, wherein at least 75% of said ribose rings are covalently modified at said 2'-OH position with a C1–C10 alkanoyl.

11. The method of claim 1, wherein at least 80% of said ribose rings are covalently modified at said 2'-OH position with a C1–C10 alkanoyl.

12. The method of claim 1, wherein at least 85% of said ribose rings are covalently modified at said 2'-OH position with a C1–C10 alkanoyl.

13. The method of claim 1, wherein at least 90% of said ribose rings are covalently modified at said 2'-OH position with a C1–C10 alkanoyl.

14. The method of claim 1, wherein at least 95% of said ribose rings are covalently modified at said 2'-OH position with a C1–C10 alkanoyl.

15. The method of claim 1, wherein at least 99% of said ribose rings are covalently modified at said 2'-OH position with a C1–C10 alkanoyl.

16. The method of claim 1, wherein said C1–C10 is acetyl.

17. The method of claim 1, wherein said 2'-OH position of the ribose rings is covalently modified so that a single strand of the poly-ribonucleotide is replicable by a nucleic acid polymerase to generate a second strand of a polynucleotide complementary to the single strand.

18. The method of claim 3, wherein said catalyst is an acylation catalyst.

19. The method of claim 18, wherein said acylation catalyst is an aminopyridine.

20. The method of claim 18, wherein said acylation catalyst is 1-methylimidazole.

21. The method of claim 1, wherein said poly-ribonucleotide is reacted with an acid anhydride.

22. The method of claim 1, wherein said poly-ribonucleotide is reacted with an acid chloride.

23. The method of claim 1, wherein said poly-ribonucleotide is reacted with N-acylimidazole.

24. The method of claim 1, wherein said reaction medium comprises water.

25. The method of claim 24, wherein said water and organic solvent are in a water:organic solvent weight ratio in a range from 1:50 to 1:10.

26. The method of clain 1, wherein said organic solvent comprises an organic base.

27. The method of claim 1, wherein said reaction conditions are such that the covalent modification of the 2'-OH positions of the ribose rings is substantially regiospeifiec.

28. The method of claim 1, wherein said poly-ribonucleotide is attached to a solid phase.

29. The method of claim 1, wherein said poly-ribonucleotide is from a cell or blood extract.

30. The method of claim 1, further comprising the step of reacting said modified poly-ribonucleotide with areactant capable of removing said C1–C10 alkanoyl under conditions to reinstate an —OH group at said 2'-OH position.

31. The method of claim 16, further comprising the step of reacting said modified polyribonucleotide with a reactant capable of removing said acetyl under conditions to reinstate an —OH group at said 2'-OH position.

32. A method for producing a composition comprising a modified poly-ribonucleotide at least 1000 bases in length, said method comprising the steps of: (i) contacting a poly-ribonucleotide in a reaction medium comprising at least 80% v/v organic solvent with a reactant capable of covalently modifying the 2'-OH position of the ribose rings of said poly-ribonucleotide; and (ii) reacting said poly-ribonucleotide to produce a modified poly-ribonucleotide comprising greater than 25% of ribose rings bearing a C1–C10 alkanoyl at their 2'-OH position.

33. The method of claim 32, wherein said method comprises the step of separating the modified poly-ribonucleotide from said reaction medium.

34. The method of claim 32, wherein said reaction medium further comprises a catalyst.

35. The method of claim 32, wherein said covalent modification is achieved in one hour or less.

36. The method of claim 32, wherein at least 50% of said ribose rings are covalently modified at said 2'-OH position with a C1–C10 alkanoyl.

37. The method of claim 32, wherein at least 75% of said ribose rings are covalently modified at said 2'-OH position with a C1–C10 alkanoyl.

38. The method of claim 32, wherein at least 80% of said ribose rings are covalently modified at said 2'-OH position with a C1–C10 alkanoyl.

39. The method of claim 32, wherein at least 85% of said ribose rings are covalently modified at said 2'-OH position with a C1–C10 alkanoyl.

40. The method of claim 32, wherein at least 90% of said ribose rings are covalently modified at said 2'-OH position with a C1–C10 alkanoyl.

41. The method of claim 32, wherein at least 95% of said ribose rings are covalently modified at said 2'-OH position with a C1–C10 alkanoyl.

42. The method of claim 32, wherein at least 99% of said ribose rings are covalently modified at said 2'-OH position with a C1–C10 alkanoyl.

43. The method of claim 32, wherein said C1–C10 is acetyl.

44. The method of claim 32, wherein said 2'-OH position of the ribose rings is covalently modified so that a single strand of the poly-ribonucleotide is replicable by a nucleic acid polymerase to generate a second strand of a polynucleotide complementary to the single strand.

45. The method of claim 34, wherein said catalyst is an acylation catalyst.

46. The method of claim 45, wherein said acylation catalyst is an aminopyridine.

47. The method of claim 45, wherein said acylation catalyst is 1-methylimidazole.

48. The method of claim 32, wherein said poly-ribonucleotide is reacted with an acid anhydride.

49. The method of claim 32, wherein said poly-ribonucleotide is reacted with an acid chloride.

50. The method of claim 32, wherein said poly-ribonucleotide is reacted with N-acylimidazole.

51. The method of claim 32, wherein said reaction medium comprises water.

52. The method of claim 51, wherein said water and organic solvent are in a water:organic solvent weight ratio in a range from 1:50 to 1:10.

53. The method of claim 32, wherein said organic solvent comprises an organic base.

54. The method of claim 32, wherein said reaction conditions are such that the covalent modification of the 2'-OH positions of the ribose rings is substantially regiospecific.

55. The method of claim 32, wherein said poly-ribonucleotide is attached to a solid phase.

56. The method of claim 32, wherein said poly-ribonucleotide is from a cell or blood extract.

57. The method of claim 32, further comprising the step of reacting said modified poly-ribonucleotide with a reactant capable of removing said C1–C10 alkanoyl under conditions to reinstate an —OH group at said 2'-OH position.

58. The method of claim 43, further comprising the step of reacting said modified polyribonucleotide with a reactant capable of removing said acetyl under conditions to reinstate an —OH group at said 2'-OH position.

* * * * *

UNITED STATES PATENT AND TRADEMARK OFFICE
CERTIFICATE OF CORRECTION

PATENT NO. : 6,867,290 B2
DATED : March 15, 2005
INVENTOR(S) : Andrew Simon Goldsborough It is certified that error appears in the above-identified patent and that said Letters Patent is hereby corrected as shown below:

Column 25,
Line 34, "recj" should read -- recJ --.

Column 41,
Line 16, "6, $\mu$g" should read -- 6, 1 $\mu$g --.

Column 43,
Line 33, "1 $\mu$g of water" should read -- 1 $\mu$l of water --.

Column 48,
Line 6, "(100 $\mu$g" should read -- (100 pg --.

Column 59,
Line 43, "MgCl$_2$, $_{400}\mu$M" should read -- MgCl$_2$, 400 $\mu$M --.

Column 60,
Line 51, "Clonezyme" should read -- CloneZyme --.

Signed and Sealed this

Seventh Day of June, 2005

JON W. DUDAS
*Director of the United States Patent and Trademark Office*